(12) United States Patent (10) Patent No.: US 8,446,275 B2
Utter, II (45) Date of Patent: May 21, 2013

(54) GENERAL HEALTH AND WELLNESS MANAGEMENT METHOD AND APPARATUS FOR A WELLNESS APPLICATION USING DATA FROM A DATA-CAPABLE BAND

(75) Inventor: Max Everett Utter, II, San Francisco, CA (US)

(73) Assignee: AliphCom, San Francisco, CA (US)

( * ) Notice: Subject to any disclaimer, the term of this patent is extended or adjusted under 35 U.S.C. 154(b) by 0 days.

(21) Appl. No.: 13/454,040

(22) Filed: Apr. 23, 2012

(65) Prior Publication Data

US 2012/0313776 A1 Dec. 13, 2012

Related U.S. Application Data

(63) Continuation-in-part of application No. 13/433,204, filed on Mar. 28, 2012, which is a continuation-in-part of application No. 13/181,495, filed on Jul. 12, 2011, which is a continuation-in-part of application No. 13/180,000, filed on Jul. 11, 2011, said application No. 13/433,204 is a continuation-in-part of application No. 13/158,416, filed on Jun. 11, 2011, which is a continuation-in-part of application No. 13/158,372, filed on Jun. 10, 2011, said application No. 13/181,495 is a continuation-in-part of application No.
(Continued)

(51) Int. Cl.
*G08B 1/08* (2006.01)

(52) U.S. Cl.
USPC .............. 340/539.12; 340/573.1; 600/300; 600/301; 482/9

(58) Field of Classification Search
USPC ............. 340/539.12, 573.1, 691.6, 693.5, 340/3.1, 3.31; 600/509, 300, 301; 482/8, 482/9, 900; 128/905, 920
See application file for complete search history.

(56) References Cited

U.S. PATENT DOCUMENTS 4,788,627 A 11/1988 Ehlert et al.
4,819,860 A 4/1989 Hargrove et al.
(Continued)

FOREIGN PATENT DOCUMENTS

EP 1639939 3/2006
EP 1702560 9/2006
(Continued)

OTHER PUBLICATIONS

U.S. Appl. No. 61/516,479, Fish et al.
(Continued)

*Primary Examiner* — Toan N Pham
(74) *Attorney, Agent, or Firm* — Kokka & Backus, PC

(57) ABSTRACT

General health and wellness management techniques and devices are configured for use with a data-capable personal worn or carried device. In one embodiment, a method receiving data representing a profile upon which a target score is established based on one or more health-related activities, and acquiring data representing one or more subsets of acquired parameters based on, for example, one or more sensors disposed in a wearable computing device. The method can include determining data representing values for the one or more subsets of the acquired parameters based on reference values for the parameters set forth in the profile and calculating at a first processor a score based on data representing the values. The score represents an attained portion of the one or more health-related activities. In some cases, the method includes causing presentation of a representation of the score relative to the target score.

19 Claims, 32 Drawing Sheets

Related U.S. Application Data

13/180,320, filed on Jul. 11, 2011, said application No. 13/433,204 is a continuation-in-part of application No. 13/158,416, which is a continuation-in-part of application No. 13/158,372, said application No. 13/181,495 is a continuation-in-part of application No. 13/158,416, which is a continuation-in-part of application No. 13/158,372, said application No. 13/181,495 is a continuation-in-part of application No. 13/158,372, said application No. 13/433,204 is a continuation-in-part of application No. 13/180,320, said application No. 13/433,204 is a continuation-in-part of application No. 13/158,416, which is a continuation-in-part of application No. 13/158,372, said application No. 13/433,204 is a continuation-in-part of application No. 13/158,416, which is a continuation-in-part of application No. 13/158,372, said application No. 13/433,204 is a continuation-in-part of application No. 13/158,372, and a continuation-in-part of application No. 13/361,919, filed on Jan. 30, 2012, which is a continuation of application No. 13/181,495, said application No. 13/433,204 is a continuation-in-part of application No. 13/180,000, said application No. 13/433,204 is a continuation-in-part of application No. 13/158,416, which is a continuation-in-part of application No. 13/158,372, said application No. 13/181,495 is a continuation-in-part of application No. 13/180,320, said application No. 13/433,204 is a continuation-in-part of application No. 13/158,416, which is a continuation-in-part of application No. 13/158,372, said application No. 13/361,919 is a continuation of application No. 13/181,511, filed on Jul. 12, 2011, said application No. 13/433,204 is a continuation-in-part of application No. 13/180,000, said application No. 13/433,204 is a continuation-in-part of application No. 13/158,416, which is a continuation-in-part of application No. 13/158,372, said application No. 13/181,511 is a continuation-in-part of application No. 13/180,320, said application No. 13/433,204 is a continuation-in-part of application No. 13/158,416, which is a continuation-in-part of application No. 13/158,372, and a continuation-in-part of application No. 13/181,511, which is a continuation-in-part of application No. 13/180,000, which is a continuation-in-part of application No. 13/158,416, which is a continuation-in-part of application No. 13/158,372, said application No. 13/181,511 is a continuation-in-part of application No. 13/180,320, said application No. 13/433,204 is a continuation-in-part of application No. 13/158,416, which is a continuation-in-part of application No. 13/158,372, and a continuation-in-part of application No. 13/433,208, filed on Mar. 28, 2012, which is a continuation-in-part of application No. 13/181,495, which is a continuation-in-part of application No. 13/180,000, and a continuation-in-part of application No. 13/158,416, which is a continuation-in-part of application No. 13/158,372, and a continuation-in-part of application No. 13/180,320, and a continuation-in-part of application No. 13/158,416, which is a continuation-in-part of application No. 13/158,372, and a continuation-in-part of application No. 13/158,416, which is a continuation-in-part of application No. 13/158,372, and a continuation-in-part of application No. 13/158,372, and a continuation-in-part of application No. 13/180,320, and a continuation-in-part of application No. 13/158,416, which is a continuation-in-part of application No. 13/158,372, and a continuation-in-part of application No. 13/158,416, which is a continuation-in-part of application No. 13/158,372, and a continuation-in-part of application No. 13/361,919, which is a continuation of application No. 13/181,495, and a continuation-in-part of application No. 13/180,000, and a continuation-in-part of application No. 13/158,416, which is a continuation-in-part of application No. 13/158,372, and a continuation-in-part of application No. 13/158,372, and a continuation of application No. 13/181,511, and a continuation-in-part of application No. 13/180,000, and a continuation-in-part of application No. 13/158,416, which is a continuation-in-part of application No. 13/158,372, and a continuation-in-part of application No. 13/180,320, and a continuation-in-part of application No. 13/158,416, which is a continuation-in-part of application No. 13/158,372, and a continuation-in-part of application No. 13/181,511, and a continuation-in-part of application No. 13/180,000, and a continuation-in-part of application No. 13/158,416, which is a continuation-in-part of application No. 13/158,372, and a continuation-in-part of application No. 13/180,320, and a continuation-in-part of application No. 13/158,416, which is a continuation-in-part of application No. 13/158,372, and a continuation-in-part of application No. 13/433,213, filed on Mar. 28, 2012, which is a continuation-in-part of application No. 13/181,495, which is a continuation-in-part of application No. 13/180,000, and a continuation-in-part of application No. 13/158,416, which is a continuation-in-part of application No. 13/158,372, and a continuation-in-part of application No. 13/180,320, and a continuation-in-part of application No. 13/158,416, which is a continuation-in-part of application No. 13/158,372, and a continuation-in-part of application No. 13/158,416, which is a continuation-in-part of application No. 13/158,372, and a continuation-in-part of application No. 13/158,372, and a continuation-in-part of application No. 13/180,320, and a continuation-in-part of application No. 13/158,416, which is a continuation-in-part of application No. 13/158,372, and a continuation-in-part of application No. 13/158,416, which is a continuation-in-part of application No. 13/158,372, and a continuation-in-part of application No. 13/158,372, and a continuation-in-part of application No. 13/361,919, which is a continuation of application No. 13/181,495, and a continuation-in-part of application No. 13/180,000, and a continuation-in-part of application No. 13/158,416, which is a continuation-in-part of application No. 13/158,372, and a continuation-in-part of application No. 13/158,372, and a continuation-in-part of application No. 13/180,320, and a continuation-in-part of application No. 13/158,416, which is a continuation-in-part of application No. 13/158,372, and a continuation of application No. 13/181,511, and a continuation-in-part of application No. 13/180,000, and a continuation-in-part of application No. 13/158,416, which is a continuation-in-part of application No. 13/158,372, and a continuation-in-part of application No. 13/180,320, and a continuation-in-part of application No. 13/158,416, which is a continuation-in-part of application No. 13/158,372, and a continuation-in-part of application No. 13/181,511, and a continuation-in-part of application No. 13/180,000, and a continuation-in-part of application No. 13/158,416, which is a continuation-in-part of application No. 13/158,372, and a continuation-in-part of application No. 13/180,320, and a continuation-in-part of application No. 13/158,416, which is a continuation-in-part of application No. 13/158,372, and a continuation-in-part of application No. 13/361,919, which is a continuation of application No. 13/181,495, and a continuation-in-part of application No. 13/180,000, and a continuation-in-part of application No. 13/158,416, which is a continuation-in-part of application No. 13/158,372, and a continuation-in-part of application No. 13/180,320, and a continuation-in-part of application No. 13/158,416, which is a continuation-in-part of application No. 13/158,372, and a continuation of application No. 13/181,511, and a continuation-in-part of application No. 13/180,000, and a continuation-in-part of application No. 13/158,416, which is a continuation-in-part of application No. 13/158,372, and a continuation-in-part of application No. 13/180,320, which is a continuation-in-part of application No. 13/158,416, which is a continuation-in-part of application No. 13/158,372, and a continuation-in-part of application No. 13/181,511, and a continuation-in-part of application No. 13/180,000, and a continuation-in-part of application No. 13/158,416, which is a continuation-in-part of application No. 13/158,372, and a continuation-in-part of application No. 13/180,320, and a continuation-in-part of application No. 13/158,416, which is a continuation-in-part of application No. 13/158,372.

(60) Provisional application No. 61/495,995, filed on Jun. 11, 2011, provisional application No. 61/495,994, filed on Jun. 11, 2011, provisional application No. 61/495,997, filed on Jun. 11, 2011, provisional application No. 61/495,996, filed on Jun. 11, 2011.

(56) References Cited

U.S. PATENT DOCUMENTS

| | | |
|---|---|---|
| 5,019,673 A | 5/1991 | Juskey et al. |
| 5,246,643 A | 9/1993 | Inaba et al. |
| 5,426,130 A | 6/1995 | Thurber et al. |
| 5,692,501 A | 12/1997 | Minturn |
| 5,924,979 A | 7/1999 | Swedlow et al. |
| 5,974,262 A | 10/1999 | Fuller et al. |
| 6,013,007 A * | 1/2000 | Root et al. ................. 482/8 |
| 6,139,494 A | 10/2000 | Cairnes |
| 6,156,461 A | 12/2000 | Grenon et al. |
| D439,981 S | 4/2001 | Kasabach et al. |
| 6,246,900 B1 | 6/2001 | Cosman et al. |
| 6,254,815 B1 | 7/2001 | Cheperak |
| D451,604 S | 12/2001 | Kasabach et al. |
| 6,356,940 B1 | 3/2002 | Short |
| D460,971 S | 7/2002 | Sica et al. |
| 6,486,801 B1 | 11/2002 | Jones |
| 6,527,711 B1 | 3/2003 | Stivoric et al. |
| 6,595,929 B2 | 7/2003 | Stivoric et al. |
| 6,605,038 B1 | 8/2003 | Teller et al. |
| 6,665,174 B1 | 12/2003 | Derr et al. |
| 6,714,859 B2 | 3/2004 | Jones |
| 6,904,359 B2 | 6/2005 | Jones |
| 6,952,645 B1 | 10/2005 | Jones |
| 6,984,886 B2 | 1/2006 | Ahn et al. |
| 7,020,508 B2 | 3/2006 | Stivoric et al. |
| 7,030,781 B2 | 4/2006 | Jones |
| 7,060,216 B2 | 6/2006 | Schuumans |
| 7,101,752 B2 | 9/2006 | Park et al. |
| 7,153,262 B2 | 12/2006 | Stivoric et al. |
| 7,196,972 B2 | 3/2007 | Pitocco et al. |
| 7,261,690 B2 | 8/2007 | Teller et al. |
| 7,276,802 B2 | 10/2007 | Hall et al. |
| 7,285,090 B2 | 10/2007 | Stivoric et al. |
| 7,306,567 B2 | 12/2007 | Loree, IV |
| 7,336,187 B2 | 2/2008 | Hubbard et al. |
| 7,343,260 B1 | 3/2008 | Kahn et al. |
| 7,364,445 B1 | 4/2008 | Ni et al. |
| 7,400,970 B2 | 7/2008 | Jones |
| 7,457,719 B1 | 11/2008 | Kahn et al. |
| 7,502,643 B2 | 3/2009 | Farringdon et al. |
| 7,647,195 B1 | 1/2010 | Kahn et al. |
| 7,647,196 B2 | 1/2010 | Kahn et al. |
| 7,653,508 B1 | 1/2010 | Kahn et al. |
| 7,655,508 B2 | 2/2010 | Johnson et al. |
| 7,662,065 B1 | 2/2010 | Kahn et al. |
| 7,689,437 B1 | 3/2010 | Teller et al. |
| 7,690,556 B1 | 4/2010 | Kahn et al. |
| 7,705,723 B2 | 4/2010 | Kahn et al. |
| 7,723,162 B2 | 5/2010 | Anderson et al. |
| 7,733,224 B2 | 6/2010 | Tran |
| 7,747,735 B1 | 6/2010 | Kahn et al. |
| 7,753,861 B1 | 7/2010 | Kahn et al. |
| 7,766,794 B2 | 8/2010 | Oliver et al. |
| 7,769,187 B1 | 8/2010 | Farrar et al. |
| 7,788,059 B1 | 8/2010 | Kahn et al. |
| 7,800,044 B1 | 9/2010 | Kahn et al. |
| 7,839,279 B2 | 11/2010 | Kahn et al. |
| 7,841,967 B1 | 11/2010 | Kahn et al. |
| 7,849,184 B1 | 12/2010 | Kahn et al. |
| D631,552 S | 1/2011 | Kasabach et al. |
| D632,396 S | 2/2011 | Kasabach et al. |
| 7,881,902 B1 | 2/2011 | Kahn et al. |
| 7,907,901 B1 | 3/2011 | Kahn et al. |
| 7,917,768 B2 | 3/2011 | Kahn et al. |
| 7,959,567 B2 | 6/2011 | Stivoric et al. |
| 7,970,586 B1 | 6/2011 | Kahn et al. |
| 7,982,770 B1 | 7/2011 | Kahn et al. |
| 7,987,070 B2 | 7/2011 | Kahn et al. |
| 7,993,276 B2 | 8/2011 | Nazarian et al. |
| D645,968 S | 9/2011 | Kasabach et al. |
| 8,040,382 B2 | 10/2011 | Kahn et al. |
| 8,047,966 B2 | 11/2011 | Dorogusker et al. |
| 8,049,614 B2 | 11/2011 | Kahn et al. |
| 8,064,759 B1 | 11/2011 | Kahn et al. |
| 8,073,707 B2 | 12/2011 | Teller et al. |
| 8,083,643 B2 | 12/2011 | Ng et al. |
| 8,096,960 B2 | 1/2012 | Loree, IV et al. |
| 2001/0004234 A1 | 6/2001 | Petelenz et al. |
| 2001/0037179 A1 | 11/2001 | Vock et al. |
| 2002/0019584 A1 | 2/2002 | Schulze et al. |
| 2002/0068873 A1 | 6/2002 | Nissila |
| 2002/0074877 A1 | 6/2002 | Lee et al. |
| 2002/0109600 A1* | 8/2002 | Mault et al. ................. 340/573.1 |
| 2002/0143491 A1 | 10/2002 | Scherzinger |
| 2002/0183646 A1 | 12/2002 | Stivoric et al. |
| 2003/0046228 A1 | 3/2003 | Berney |
| 2003/0130595 A1 | 7/2003 | Mault |
| 2003/0236474 A1 | 12/2003 | Singh |
| 2004/0147818 A1 | 7/2004 | Levy et al. |
| 2004/0152957 A1 | 8/2004 | Stivoric et al. |
| 2004/0167409 A1 | 8/2004 | Lo et al. |
| 2005/0113650 A1 | 5/2005 | Pacione et al. |

| | | |
|---|---|---|
| 2005/0140005 A1 | 6/2005 | Huang et al. |
| 2005/0245839 A1 | 11/2005 | Stivoric et al. |
| 2006/0065645 A1 | 3/2006 | Nakasu et al. |
| 2006/0074279 A1 | 4/2006 | Brover |
| 2006/0079740 A1 | 4/2006 | Silver et al. |
| 2006/0122474 A1 | 6/2006 | Teller et al. |
| 2006/0132477 A1 | 6/2006 | Kerr et al. |
| 2006/0224051 A1 | 10/2006 | Teller et al. |
| 2006/0237252 A1 | 10/2006 | Mobley et al. |
| 2007/0027370 A1 | 2/2007 | Brauker et al. |
| 2007/0072156 A1 | 3/2007 | Kaufman et al. |
| 2007/0105404 A1 | 5/2007 | Lee et al. |
| 2007/0173705 A1 | 7/2007 | Teller et al. |
| 2007/0185391 A1 | 8/2007 | Morgan |
| 2007/0186429 A1 | 8/2007 | Bonnet et al. |
| 2007/0197878 A1 | 8/2007 | Shklarski |
| 2007/0253602 A1 | 11/2007 | Amano |
| 2007/0254137 A1 | 11/2007 | Koppe et al. |
| 2007/0296571 A1 | 12/2007 | Kolen |
| 2008/0004904 A1 | 1/2008 | Tran |
| 2008/0032119 A1 | 2/2008 | Feldhahn et al. |
| 2008/0040615 A1 | 2/2008 | Carper et al. |
| 2008/0055074 A1 | 3/2008 | Gao et al. |
| 2008/0091089 A1 | 4/2008 | Guillory et al. |
| 2008/0154098 A1 | 6/2008 | Morris et al. |
| 2008/0167535 A1 | 7/2008 | Stivoric et al. |
| 2008/0176655 A1 | 7/2008 | James et al. |
| 2008/0183388 A1 | 7/2008 | Goodrich |
| 2008/0194928 A1 | 8/2008 | Bandic et al. |
| 2008/0208015 A1 | 8/2008 | Morris et al. |
| 2008/0216171 A1 | 9/2008 | Sano |
| 2008/0255979 A1 | 10/2008 | Slutzky et al. |
| 2008/0275309 A1 | 11/2008 | Stivoric et al. |
| 2009/0006458 A1 | 1/2009 | Stivoric et al. |
| 2009/0019374 A1 | 1/2009 | Logan et al. |
| 2009/0072955 A1 | 3/2009 | Cary |
| 2009/0076343 A1 | 3/2009 | James et al. |
| 2009/0077849 A1 | 3/2009 | Glass, Jr. et al. |
| 2009/0112626 A1 | 4/2009 | Talbot et al. |
| 2009/0118100 A1 | 5/2009 | Oliver et al. |
| 2009/0131759 A1 | 5/2009 | Sims et al. |
| 2009/0146947 A1 | 6/2009 | Ng |
| 2009/0150178 A1 | 6/2009 | Sutton et al. |
| 2009/0163774 A1 | 6/2009 | Thatha et al. |
| 2009/0192362 A1 | 7/2009 | Sweeney |
| 2009/0208756 A1 | 8/2009 | Kimura et al. |
| 2009/0218725 A1 | 9/2009 | Thelemann et al. |
| 2009/0264714 A1 | 10/2009 | Chou |
| 2009/0265183 A1 | 10/2009 | Pollard et al. |
| 2009/0292180 A1 | 11/2009 | Mirow |
| 2009/0319221 A1 | 12/2009 | Kahn et al. |
| 2009/0319347 A1 | 12/2009 | Albrecht |
| 2010/0004947 A1 | 1/2010 | Nadeau et al. |
| 2010/0030578 A1 | 2/2010 | Siddique et al. |
| 2010/0041772 A1 | 2/2010 | Liversage et al. |
| 2010/0056878 A1 | 3/2010 | Partin et al. |
| 2010/0070867 A1 | 3/2010 | Lemmers |
| 2010/0119461 A1 | 5/2010 | Bicard-Benhamou et al. |
| 2010/0137106 A1 | 6/2010 | Oshima et al. |
| 2010/0156007 A1 | 6/2010 | Huang et al. |
| 2010/0217099 A1 | 8/2010 | LeBoeuf et al. |
| 2010/0221188 A1 | 9/2010 | Clark et al. |
| 2010/0240962 A1 | 9/2010 | Contant |
| 2010/0241465 A1 | 9/2010 | Amigo et al. |
| 2010/0268056 A1 | 10/2010 | Picard et al. |
| 2010/0279554 A1 | 11/2010 | Steijner |
| 2010/0284552 A1 | 11/2010 | Lasarov et al. |
| 2010/0305642 A1 | 12/2010 | Dong et al. |
| 2010/0315225 A1 | 12/2010 | Teague |
| 2010/0331146 A1 | 12/2010 | Kil |
| 2010/0331682 A1 | 12/2010 | Stein et al. |
| 2011/0004072 A1 | 1/2011 | Fletcher et al. |
| 2011/0010188 A1 | 1/2011 | Yoshikawa et al. |
| 2011/0046519 A1 | 2/2011 | Raheman |
| 2011/0054359 A1 | 3/2011 | Sazonov et al. |
| 2011/0066064 A1 | 3/2011 | Jangle et al. |
| 2011/0071003 A1 | 3/2011 | Watterson et al. |
| 2011/0087115 A1 | 4/2011 | Sackner et al. |
| 2011/0095916 A1 | 4/2011 | Kass et al. |
| 2011/0106627 A1 | 5/2011 | Le Boeuf et al. |
| 2011/0125063 A1 | 5/2011 | Shalon et al. |
| 2011/0160544 A1 | 6/2011 | Hayter |
| 2011/0184247 A1 | 7/2011 | Contant et al. |
| 2011/0230732 A1 | 9/2011 | Edman et al. |
| 2011/0245633 A1 | 10/2011 | Goldberg et al. |
| 2012/0313773 A1 | 12/2012 | Loree, IV |

FOREIGN PATENT DOCUMENTS

| | | |
|---|---|---|
| IL | 153478 | 3/2009 |
| WO | WO/01/96986 | 12/2001 |
| WO | WO/02/00111 | 1/2002 |
| WO | WO/02/078538 | 10/2002 |
| WO | WO/03/015005 | 2/2003 |
| WO | WO/2004/019172 | 3/2004 |
| WO | WO/2005/016124 | 2/2005 |
| WO | WO/2005/092177 | 10/2005 |
| WO | WO/2008/101248 | 8/2008 |
| WO | WO/2010/064162 | 6/2010 |
| WO | WO/2010/065067 | 6/2010 |
| WO | WO/2011/046657 | 4/2011 |

OTHER PUBLICATIONS

U.S. Appl. No. 61/404,379, Fish et al.
U.S. Appl. No. 61/516,480, Fish et al.
U.S. Appl. No. 61/404,381, Ram David Adva Fish.
U.S. Appl. No. 12/684,881, filed Jul. 14, 2011, Kahn et al.
U.S. Appl. No. 12/472,361, filed Dec. 2, 2010, Kahn et al.
U.S. Appl. No. 12/247,950, filed Apr. 8, 2010, Kahn et al.
U.S. Appl. No. 12/202,206, filed Mar. 4, 2010, Kahn et al.
U.S. Appl. No. 12/469,633, filed Nov. 26, 2009, Kahn et al.
U.S. Appl. No. 12/033,753, filed Dec. 25, 2008, Stivoric et al.
U.S. Appl. No. 12/033,760, filed Dec. 25, 2008, Stivoric et al.
U.S. Appl. No. 12/033,766 filed Dec. 25, 2008, Stivoric et al.
U.S. Appl. No. 12/217,299, filed Jul. 9, 2009, Stivoric et al.
U.S. Appl. No. 12/840,109, filed Nov. 11, 2010, Farringdon et al.
U.S. Appl. No. 60/729,663, Donald G. Stein.
U.S. Appl. No. 60/727,357, Pacione et al.
U.S. Appl. No. 60/555,280, Pacione et al.
U.S. Appl. No. 60/502,746, Bucher et al.
U.S. Appl. No. 60/417,163, Andre et al.
U.S. Appl. No. 60/729,683, Stivoric et al.
U.S. Appl. No. 60/958,516, Andre et al.
U.S. Appl. No. 60/510,013, Farringdon et al.
U.S. Appl. No. 60/502,764, Stivoric et al.
U.S. Appl. No. 60/901,952, Stivoric et al.
U.S. Appl. No. 11/925,902, filed May 7, 2009, Teller et al.
U.S. Appl. No. 11/925,903, filed Jul. 31, 2008, Teller et al.
U.S. Appl. No. 11/925,908, filed Jul. 17, 2008, Teller et al.
U.S. Appl. No. 11/876,601, Stivoric et al.
U.S. Appl. No. 11/927,276, filed Nov. 20, 2008, Stivoric et al.
U.S. Appl. No. 13/253,000, Ram David Adva Fish.
U.S. Appl. No. 13/182,352, filed Jan. 5, 2012, Nazarian et al.
U.S. Appl. No. 12/560,069, filed Aug. 26, 2010, Nadkarni et al.
U.S. Appl. No. 12/621,099, filed Sep. 30, 2010, Nadkarni et al.
U.S. Appl. No. 12/823,280, filed Jan. 6, 2011, Bentley et al.
U.S. Appl. No. 12/883,304, filed Mar. 17, 2011, Jangle et al.
U.S. Appl. No. 12/891,108, filed Mar. 17, 2011, Jangle et al.
U.S. Appl. No. 13/204,658, filed Nov. 24, 2011, Jangle et al.
U.S. Appl. No. 61/210,821, Ram David Adva Fish.
U.S. Appl. No. 61/210,862, Ram David Adva Fish.
U.S. Appl. No. 12/730,194, filed Sep. 23, 2010, Ram David Adva Fish.
U.S. Appl. No. 12/730,199, filed Sep. 23, 2010, Ram David Adva Fish.
U.S. Appl. No. 61/630,064, Ram David Adva Fish.
U.S. Appl. No. 61/627,891, Ram David Adva Fish.
U.S. Appl. No. 61/516,478, Fish et al.
U.S. Appl. No. 61/516,477, Ram David Adva Fish.
U.S. Appl. No. 13/405,241, Rahman et al.
U.S. Appl. No. 13/158,416, Drysdale et al.
U.S. Appl. No. 13/135,728, Drysdale et al.
U.S. Appl. No. 61/495,995, Drysdale et al.
U.S. Appl. No. 13/180,320, Rahman et al.

U.S. Appl. No. 61/495,994, Drysdale et al.
U.S. Appl. No. 13/181,512, Rahman et al.
U.S. Appl. No. 61/495,997, Drysdale et al.
U.S. Appl. No. 61/495,996, Drysdale et al.
U.S. Appl. No. 61/511,541, Jeffery Miao.
U.S. Appl. No. 13/247,975, Sashittal et al.
U.S. Appl. No. 13/180,000, Rahman et al.
U.S. Appl. No. 61/507,091, Rahman et al.
U.S. Appl. No. 61/572,204, Rahman et al.
U.S. Appl. No. 61/572,206, Rahman et al.
U.S. Appl. No. 13/181,495, Rahman et al.
U.S. Appl. No. 13/181,511, Rahman et al.
U.S. Appl. No. 13/181,486, Rahman et al.
U.S. Appl. No. 13/181,500, Rahman et al.
U.S. Appl. No. 13/181,498, Rahman et al.
U.S. Appl. No. 13/181,513, Rahman et al.
U.S. Appl. No. 13/361,919, Rahman et al.
U.S. Appl. No. 12/113,110, filed Nov. 5, 2009, Kahn et al.
U.S. Appl. No. 11/871,151, filed Apr. 16, 2009, Kahn et al.
U.S. Appl. No. 12/490,304, filed Dec. 24, 2009, Kahn et al.
U.S. Appl. No. 11/582,896, filed May 3, 2007, Stivoric et al.
U.S. Appl. No. 10/638,588, filed Feb. 19, 2004, Teller et al.
U.S. Appl. No. 10/682,293, filed Jul. 8, 2004, Teller et al.
U.S. Appl. No. 10/940,214, filed May 26, 2005, Pacione et al.
U.S. Appl. No. 11/088,002, filed Nov. 3, 2005, Stivoric et al.
U.S. Appl. No. 11/239,748, filed Nov. 23, 2006, Stivoric et al.
U.S. Appl. No. 11/322,010, filed Jun. 8, 2006, Teller et al.
U.S. Appl. No. 11/434,949, filed Oct. 5, 2006, Teller et al.
U.S. Appl. No. 11/481,147, filed Feb. 15, 2007, Stivoric et al.
U.S. Appl. No. 11/724,373, filed Jul. 26, 2007, Teller et al.
U.S. Appl. No. 11/925,906, filed Jul. 31, 2008, Teller et al.
U.S. Appl. No. 11/925,965, Jul. 17, 2008, Stivoric et al.
U.S. Appl. No. 11/928,039, filed Jul. 10, 2008, Stivoric et al.
U.S. Appl. No. 11/928,302, filed Jul. 31, 2008, Farringdon et al.
U.S. Appl. No. 11/930,036, filed Jul. 10, 2008, Teller et al.
U.S. Appl. No. 11/930,053, filed Jul. 10, 2008, Teller et al.
U.S. Appl. No. 11/930,081, filed Jul. 3, 2008, Teller et al.
U.S. Appl. No. 11/930,091, filed Jul. 3, 2008, Teller et al.
U.S. Appl. No. 11/930,092, filed Jul. 17, 2008, Teller et al.
U.S. Appl. No. 11/930,094, filed Jul. 17, 2008, Teller et al.
U.S. Appl. No. 12/033,728, filed Jan. 1, 2009, Stivoric et al.
U.S. Appl. No. 12/033,722, filed Jan. 1, 2009, Stivoric et al.
U.S. Appl. No. 12/033,731, filed Dec. 25, 2008, Stivoric et al.
U.S. Appl. No. 12/033,737, filed Dec. 25, 2008, Stivoric et al.
U.S. Appl. No. 12/033,741, filed Dec. 25, 2008, Stivoric et al.
U.S. Appl. No. 12/033,746, filed Dec. 25, 2008, Stivoric et al.
U.S. Appl. No. 12/033,751, filed Dec. 25, 2008, Stivoric et al.
U.S. Appl. No. 11/930,405, filed Jul. 24, 2008, Teller et al.
U.S. Appl. No. 11/928,059, filed Sep. 4, 2008, Stivoric et al.
U.S. Appl. No. 11/928,027, filed Jul. 3, 2008, Stivoric et al.
U.S. Appl. No. 11/928,051, filed Jul. 10, 2008, Stivoric et al.
U.S. Appl. No. 11/930,100, filed Jul. 17, 2008, Teller et al.
U.S. Appl. No. 11/930,048, filed Jul. 10, 2008, Teller et al.
U.S. Appl. No. 11/930,101, filed Jul. 10, 2008, Teller et al.
U.S. Appl. No. 11/927,365, filed Nov. 20, 2008, Stivoric et al.
U.S. Appl. No. 13/405,240, filed Feb. 25, 2012, Drysdale et al.
USPTO Office Action in U.S. Appl. No. 13/427,839, mailed Jul. 12, 2012.
USPTO Office Action in U.S. Appl. No. 13/405,240, mailed Nov. 29, 2012.
USPTO Office Action in U.S. Appl. No. 13/181,495, mailed Mar. 28, 2012.
USPTO Office Action in U.S. Appl. No. 13/181,495, mailed Nov. 21, 2012.
USPTO Office Action in U.S. Appl. No. 13/361,919, mailed Mar. 23, 2012.
USPTO Office Action in U.S. Appl. No. 13/361,919, mailed Nov. 6, 2012.
USPTO Office Action in U.S. Appl. No. 13/405,241, mailed Sep. 21, 2012.
Lee W. Young; Notification of Transmittal of the International Search Report and the Written Opinion of the International Searching Authority, or the Declaration; International application No. PCT/US 12/31319; Date of Mailing Jul. 20, 2012.
Lee W. Young; Notification of Transmittal of the International Search Report and the Written Opinion of the International Searching Authority, or the Declaration; International application No. PCT/US 12/41964; Date of Mailing Aug. 28, 2012.
Lee W. Young; Notification of Transmittal of the International Search Report and the Written Opinion of the International Searching Authority, or the Declaration; International application No. PCT/US 12/31322; Date of Mailing Jul. 13, 2012.
Lee W. Young; Notification of Transmittal of the International Search Report and the Written Opinion of the International Searching Authority, or the Declaration; International application No. PCT/US 12/40797; Date of Mailing Aug. 10, 2012.
Lee W. Young; Notification of Transmittal of the International Search Report and the Written Opinion of the International Searching Authority, or the Declaration; International application No. PCT/US 12/38185; Date of Mailing Aug. 17, 2012.
Blaine R. Copenheaver; Notification of Transmittal of the International Search Report and the Written Opinion of the International Searching Authority, or the Declaration; International application No. PCT/US 12/039761; Date of Mailing Sep. 7, 2012.
Lee W. Young; Notification of Transmittal of the International Search Report and the Written Opinion of the International Searching Authority, or the Declaration; International application No. PCT/US 12/38201; Date of Mailing Jul. 20, 2012.
Shane Thomas; Notification of Transmittal of the International Search Report and the Written Opinion of the International Searching Authority, or the Declaration; International application No. PCT/US 12/41710; Date of Mailing Aug. 24, 2012.
Blaine R. Copenheaver; Notification of Transmittal of the International Search Report and the Written Opinion of the International Searching Authority, or the Declaration; International application No. PCT/US 12/41940; Date of Mailing Sep. 13, 2012.
Blaine R. Copenheaver; Notification of Transmittal of the International Search Report and the Written Opinion of the International Searching Authority, or the Declaration; International application No. PCT/US 12/38410; Date of Mailing Sep. 7, 2012.
Blaine R. Copenheaver; Notification of Transmittal of the International Search Report and the Written Opinion of the International Searching Authority, or the Declaration; International application No. PCT/US 12/41959; Date of Mailing Sep. 13, 2012.
Lee W. Young; Notification of Transmittal of the International Search Report and the Written Opinion of the International Searching Authority, or the Declaration; International application No. PCT/US 12/31325; Date of Mailing Jul. 24, 2012.
Lee W. Young; Notification of Transmittal of the International Search Report and the Written Opinion of the International Searching Authority, or the Declaration; International application No. PCT/US 12/41177; Date of Mailing Sep. 14, 2012.
Lee W. Young; Notification of Transmittal of the International Search Report and the Written Opinion of the International Searching Authority, or the Declaration; International application No. PCT/US 12/40965; Date of Mailing Aug. 1, 2012.
Lee W. Young; Notification of Transmittal of the International Search Report and the Written Opinion of the International Searching Authority, or the Declaration; International application No. PCT/US 12/39763; Date of Mailing Aug. 7, 2012.
Lee W. Young; Notification of Transmittal of the International Search Report and the Written Opinion of the International Searching Authority, or the Declaration; International application No. PCT/US 12/40047; Date of Mailing Aug. 16, 2012.
Lee W. Young; Notification of Transmittal of the International Search Report and the Written Opinion of the International Searching Authority, or the Declaration; International application No. PCT/US 12/40328; Date of Mailing Aug. 17, 2012.
Lee W. Young; Notification of Transmittal of the International Search Report and the Written Opinion of the International Searching Authority, or the Declaration; International application No. PCT/US 12/31326; Date of Mailing Aug. 3, 2012.

Lee W. Young; Notification of Transmittal of the International Search Report and the Written Opinion of the International Searching Authority, or the Declaration; International application No. PCT/US 12/40812; Date of Mailing Aug. 22, 2012.

Lee W. Young; Notification of Transmittal of the International Search Report and the Written Opinion of the International Searching Authority, or the Declaration; International application No. PCT/US 12/40590; Date of Mailing Sep. 7, 2012.

Lauren Goode; Sleep-Sensor Maker Lark Takes on Nike+ FuelBand With Larklife, All Things Digital, Oct. 8, 2012, The Wall Street Journal.

Deborah Porterfield; Life Gets Easier with New Tech Accessories, USA Today, Oct. 18, 2012.

* cited by examiner

GENERAL HEALTH AND WELLNESS MANAGEMENT METHOD AND APPARATUS FOR A WELLNESS APPLICATION USING DATA FROM A DATA-CAPABLE BAND

CROSS-REFERENCE TO RELATED APPLICATIONS

THIS application is a continuation-in-part of U.S. non-provisional patent application 13/433,204, filed Mar. 28, 2012, which is a continuation-in-part of U.S. non-provisional patent application Ser. No. of 13/181,495, filed Jul. 12, 2011, which is a continuation-in-part of prior U.S. patent application Ser. No. 13/180,000, filed Jul. 11, 2011, which claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, U.S. Provisional Patent Application No. 61/495,996, filed Jun. 11, 2011, and U.S. patent application Ser. No. 13/180,000 is a continuation-in-part of prior U.S. patent application Ser. No. 13/158,416, filed Jun. 11, 2011, which is a continuation-in-part of prior U.S. patent application Ser. No. 13/158,372, filed Jun. 10, 2011, and U.S. patent application Ser. No. 13/181,495 claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, and U.S. Provisional Patent Application No. 61/495,996, filed Jun. 11, 2011; U.S. patent application Ser. No. 13/181,495 is also a continuation-in-part of prior U.S. patent application Ser. No. 13/180,320, filed Jul. 11, 2011, which claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, U.S. Provisional Patent Application No. 61/495,996, filed Jun. 11, 2011, and U.S. patent application Ser. No. 13/180,320 is a continuation-in-part of prior U.S. patent application Ser. No. 13/158,416, filed Jun. 11, 2011, which is a continuation-in-part of prior U.S. patent application Ser. No. 13/158,372, filed Jun. 10, 2011, which claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, U.S. Provisional Patent Application No. 61/495,996, filed Jun. 11, 2011; U.S. patent application Ser. No. 13/181,495 is also a continuation-in-part of prior U.S. patent application Ser. No. 13/158,416, filed Jun. 11, 2011, which is a continuation-in-part of prior U.S. patent application Ser. No. 13/158,372, filed Jun. 10, 2011; U.S. non-provisional patent application Ser. No. 13/433,204 claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, and U.S. Provisional Patent Application No. 61/495,996, filed Jun. 11, 2011, and is a continuation-in-part of prior U.S. patent application Ser. No. 13/180,320, filed Jul. 11, 2011, which claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, U.S. Provisional Patent Application No. 61/495,996, filed Jun. 11, 2011, and is a continuation-in-part of prior U.S. patent application Ser. No. 13/158,416, filed Jun. 11, 2011, which is a continuation-in-part of prior U.S. patent application Ser. No. 13/158,372, filed Jun. 10, 2011, and also is a continuation-in-part of prior U.S. patent application Ser. No. 13/158,416, filed Jun. 11, 2011, which is a continuation-in-part of prior U.S. patent application Ser. No. 13/158,372, filed Jun. 10, 2011, and is also a continuation-in-part of prior U.S. patent application Ser. No. 13/158,372, filed Jun. 10, 2011; U.S. non-provisional patent application Ser. No. 13/433,204 is also a continuation-in-part of U.S. Nonprovisional patent application Ser. No. 13/361,919, filed Jan. 30, 2012, which is a continuation of U.S. Nonprovisional patent application Ser. No. 13/181,495 filed Jul. 12, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and, U.S. Nonprovisional patent application Ser. No. 13/361,919 is a continuation-in-part of U.S. patent application Ser. No. 13/180,000 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and U.S. Nonprovisional patent application Ser. No. 13/361,919 is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. Nonprovisional patent application Ser. No. 13/181,495 filed Jul. 12, 2011 is also a continuation-in-part of U.S. patent application Ser. No. 13/180,320 filed Jul. 11, 2011, which claims the benefit of U.S. Provisional Patent Application No. 61/495,995 filed Jun. 11, 2011, U.S. Provisional Patent Application No. 61/495,994 filed. Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. Nonprovisional patent application Ser. No. 13/361,919 is also a continuation of U.S. patent application Ser. No. 13/181,511 filed Jul. 12, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/180,000 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. patent application Ser. No. 13/181,511 filed Jul. 12, 2011 is also a continuation-in-part of U.S. patent application Ser. No. 13/180,320 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495, 996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. non-provisional patent application Ser. No. 13/433,204 is also a continuation-in-part of U.S. patent application Ser. No. 13/181,511 filed Jul. 12, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/180,000 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. patent application Ser. No. 13/181,511 filed Jul. 12, 2011 is also a continuation-in-part of U.S. patent application Ser. No. 13/180,320 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; THIS application is a continuation-in-part of U.S. non-provisional patent application Ser. No. 13/433,208, filed Mar. 28, 2012, which is a continuation-in-part of U.S. non-provisional patent application Ser. No. of 13/181,495, filed Jul. 12, 2011, which is a continuation-in-part of prior U.S. patent application Ser. No. 13/180,000, filed Jul. 11, 2011, which claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, U.S. Provisional Patent Application No. 61/495,996, filed Jun. 11, 2011, and U.S. patent application Ser. No. 13/180,000 is a continuation-in-part of prior U.S. patent application Ser. No. 13/158,416, filed Jun. 11, 2011, which is a continuation-in-part of prior U.S. patent application Ser. No. 13/158,372, filed Jun. 10, 2011, and U.S. patent application Ser. No. 13/181,495 claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, and U.S. Provisional Patent Application No. 61/495,996, filed Jun. 11, 2011; U.S. patent application Ser. No. 13/181,495 is also a continuation-in-part of prior U.S. patent application Ser. No. 13/180,320, filed Jul. 11, 2011, which claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, U.S. Provisional Patent Application No. 61/495,996, filed Jun. 11, 2011, and U.S. patent application Ser. No. 13/180,320 is a continuation-in-part of prior U.S. patent application Ser. No. 13/158,416, filed Jun. 11, 2011, which is a continuation-in-part of prior U.S. patent application Ser. No. 13/158,372, filed Jun. 10, 2011, which claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, U.S. Provisional Patent Application No. 61/495,996, filed Jun. 11, 2011; U.S. patent application Ser. No. 13/181,495 is also a continuation-in-part of prior U.S. patent application Ser. No. 13/158,416, filed Jun. 11, 2011, which is a continuation-in-part of prior U.S. patent application Ser. No. 13/158,372, filed Jun. 10, 2011; U.S. patent application Ser. No. 13/181,495 is also a continuation-in-part of prior U.S. patent application Ser. No. 13/158,372, filed Jun. 10, 2011; U.S. non-provisional patent application Ser. No. 13/433,208 claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, and U.S. Provisional Patent Application No. 61/495,996, filed Jun. 11, 2011, and is a continuation-in-part of prior U.S. patent application Ser. No. 13/180,320, filed Jul. 11, 2011, which claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, U.S. Provisional Patent Application No. 61/495,996, filed Jun. 11, 2011, and is a continuation-in-part of prior U.S. patent application Ser. No. 13/158,416, filed Jun. 11, 2011, which is a continuation-in-part of prior U.S. patent application Ser. No. 13/158,372, filed Jun. 10, 2011, and also is a continuation-in-part of prior U.S. patent application Ser. No. 13/158,416, filed Jun. 11, 2011, which is a continuation-in-part of prior U.S. patent application Ser. No. 13/158,372, filed Jun. 10, 2011, and is also a continuation-in-part of prior U.S. patent application Ser. No. 13/158,372, filed Jun. 10, 2011; U.S. non-provisional patent application Ser. No. 13/433,208 is also a continuation-in-part of U.S. Nonprovisional patent application Ser. No. 13/361,919, filed Jan. 30, 2012, which is a continuation of U.S. Nonprovisional patent application Ser. No. 13/181,495 filed Jul. 12, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and, U.S. Nonprovisional patent application Ser. No. 13/361,919 is a continuation-in-part of U.S. patent application Ser. No. 13/180,000 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and U.S. Nonprovisional patent application Ser. No. 13/361,919 is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. Nonprovisional patent application Ser. No. 13/181,495 filed Jul. 12, 2011 is also a continuation-in-part of U.S. patent application Ser. No. 13/180,320 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. Nonprovisional patent application Ser. No. 13/361,919 is also a continuation of U.S. patent application Ser. No. 13/181,511 filed Jul. 12, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/180,000 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. patent application Ser. No. 13/181,511 filed Jul. 12, 2011 is also a continuation-in-part of U.S. patent application Ser. No. 13/180,320 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. non-provisional patent application 13/433,208 is also a continuation-in-part of U.S. patent application Ser. No. 13/181,511 filed Jul. 12, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/180,000 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. patent application Ser. No. 13/181,511 filed Jul. 12, 2011 is also a continuation-in-part of U.S. patent application Ser. No. 13/180,320 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; THIS application is a continuation-in-part of U.S. non-provisional patent application Ser. No. 13/433,213, filed Mar. 28, 2012, which is a continuation-in-part of U.S. non-provisional patent application Ser. No. of 13/181,495, filed Jul. 12, 2011, which is a continuation-in-part of prior U.S. patent application Ser. No. 13/180,000, filed Jul. 11, 2011, which claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, U.S. Provisional Patent Application No. 61/495,996, filed Jun. 11, 2011, and U.S. patent application Ser. No. 13/180,000 is a continuation-in-part of prior U.S. patent application Ser. No. 13/158,416, filed Jun. 11, 2011, which is a continuation-in-part of prior U.S. patent application Ser. No. 13/158,372, filed Jun. 10, 2011, and U.S. patent application Ser. No. 13/181,495 claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, and U.S. Provisional Patent Application No. 61/495,996, filed Jun. 11, 2011; U.S. patent application Ser. No. 13/181,495 is also a continuation-in-part of prior U.S. patent application Ser. No. 13/180,320, filed Jul. 11, 2011, which claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, U.S. Provisional Patent Application No. 61/495,996, filed Jun. 11, 2011, and U.S. patent application Ser. No. 13/180,320 is a continuation-in-part of prior U.S. patent application Ser. No. 13/158,416, filed Jun. 11, 2011, which is a continuation-in-part of prior U.S. patent application Ser. No. 13/158,372, filed Jun. 10, 2011, which claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, U.S. Provisional Patent Application No. 61/495,996, filed Jun. 11, 2011; U.S. patent application Ser. No. 13/181,495 is also a continuation-in-part of prior U.S. patent application Ser. No. 13/158,416, filed Jun. 11, 2011, which is a continuation-in-part of prior U.S. patent application Ser. No. 13/158,372, filed Jun. 10, 2011; U.S. patent application Ser. No. 13/181,495 is also a continuation-in-part of prior U.S. patent application Ser. No. 13/158,372, filed Jun. 10, 2011; U.S. non-provisional patent application Ser. No. 13/433,213 claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, and U.S. Provisional Patent Application No. 61/495,996, filed Jun. 11, 2011, and is a continuation-in-part of prior U.S. patent application Ser. No. 13/180,320, filed Jul. 11, 2011, which claims the benefit of U.S. Provisional Patent Application No. 61/495,995, filed Jun. 11, 2011, U.S. Provisional Patent Application No. 61/495,994, filed Jun. 11, 2011, U.S. Provisional Patent Application No. 61/495,997, filed Jun. 11, 2011, U.S. Provisional Patent Application No. 61/495,996, filed Jun. 11, 2011, and is a continuation-in-part of prior U.S. patent application Ser. No. 13/158,416, filed Jun. 11, 2011, which is a continuation-in-part of prior U.S. patent application Ser. No. 13/158,372, filed Jun. 10, 2011, and also is a continuation-in-part of prior U.S. patent application Ser. No. 13/158,416, filed Jun. 11, 2011, which is a continuation-in-part of prior U.S. patent application Ser. No. 13/158,372, filed Jun. 10, 2011, and is also a continuation-in-part of prior U.S. patent application Ser. No. 13/158,372, filed Jun. 10, 2011; U.S. non-provisional patent application Ser. No. 13/433,213 is also a continuation-in-part of U.S. Nonprovisional patent application Ser. No. 13/361,919, filed Jan. 30, 2012, which is a continuation of U.S. Nonprovisional patent application Ser. No. 13/181,495 filed Jul. 12, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and, U.S. Nonprovisional patent application Ser. No. 13/361,919 is a continuation-in-part of U.S. patent application Ser. No. 13/180,000 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and U.S. Nonprovisional patent application Ser. No. 13/361, 919 is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. Nonprovisional patent application Ser. No. 13/181,495 filed Jul. 12, 2011 is also a continuation-in-part of U.S. patent application Ser. No. 13/180,320 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495, 996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. Nonprovisional patent application Ser. No. 13/361,919 is also a continuation of U.S. patent application Ser. No. 13/181,511 filed Jul. 12, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495, 996 filed Jun. 11, 2011 and is a continuation-in-part of U.S. patent application Ser. No. 13/180,000 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. patent application Ser. No. 13/181,511 filed Jul. 12, 2011 is also a continuation-in-part of U.S. patent application Ser. No. 13/180,320 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495, 996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. non-provisional patent application Ser. No. 13/433,213 is also a continuation-in-part of U.S. patent application Ser. No. 13/181,511 filed Jul. 12, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/180,000 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. patent application Ser. No. 13/181,511 filed Jul. 12, 2011 is also a continuation-in-part of U.S. patent application Ser. No. 13/180,320 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; THIS application claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is also a continuation-in-part of U.S. Nonprovisional patent application Ser. No. 13/361,919, filed Jan. 30, 2012, which is a continuation of U.S. Nonprovisional patent application Ser. No. 13/181,495 filed Jul. 12, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and, is a continuation-in-part of U.S. patent application Ser. No. 13/180,000 filed Jul. 11, 2011, which claims the benefit of U.S. Provisional Patent Application No. 61/495, 995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. Nonprovisional patent application Ser. No. 13/181,495 filed Jul. 12, 2011 is also a continuation-in-part of U.S. patent application Ser. No. 13/180,320 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495, 996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. Nonprovisional patent application Ser. No. 13/361,919 is also a continuation of U.S. patent application Ser. No. 13/181,511 filed Jul. 12, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495, 996 filed Jun. 11, 2011 and is a continuation-in-part of U.S. patent application Ser. No. 13/180,000 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. patent application Ser. No. 13/181,511 filed Jul. 12, 2011 is also a continuation-in-part of U.S. patent application Ser. No. 13/180,320 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; THIS application is also a continuation-in-part of U.S. patent application Ser. No. 13/181,511 filed Jul. 12, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/180,000 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011; U.S. patent application Ser. No. 13/181,511 filed Jul. 12, 2011 is also a continuation-in-part of U.S. patent application Ser. No. 13/180,320 filed Jul. 11, 2011, which claims the benefit of U.S. Provisional Patent Application No. 61/495,995 filed Jun. 11, 2011, U.S. Provisional Patent Application No. 61/495,994 filed Jun. 11, 2011, U.S. Provisional Patent Application No. 61/495,997 filed Jun. 11, 2011, U.S. Provisional Patent Application No. 61/495,996 filed Jun. 11, 2011 and is a continuation-in-part of U.S. patent application Ser. No. 13/158,416 filed Jun. 11, 2011, which is a continuation-in-part of U.S. patent application Ser. No. 13/158,372 filed Jun. 10, 2011, ALL of which are herein incorporated by reference for all purposes.

FIELD

The present invention relates generally to electrical and electronic hardware, computer software, wired and wireless network communications, and computing devices. More specifically, general health and wellness management techniques and devices for use with a data-capable personal worn or carried device are described.

BACKGROUND

With the advent of greater computing capabilities in smaller personal and/or portable form factors and an increasing number of applications (i.e., computer and Internet software or programs) for different uses, consumers (i.e., users) have access to large amounts of personal data. Information and data are often readily available, but poorly captured using conventional data capture devices. Conventional devices typically lack capabilities that can capture, analyze, communicate, or use data in a contextually-meaningful, comprehensive, and efficient manner. Further, conventional solutions are often limited to specific individual purposes or uses, demanding that users invest in multiple devices in order to perform different activities (e.g., a sports watch for tracking time and distance, a GPS receiver for monitoring a hike or run, a cyclometer for gathering cycling data, and others). Although a wide range of data and information is available, conventional devices and applications fail to provide effective solutions that comprehensively capture data for a given user across numerous disparate activities.

Some conventional solutions combine a small number of discrete functions. Functionality for data capture, processing, storage, or communication in conventional devices such as a watch or timer with a heart rate monitor or global positioning system ("GPS") receiver are available conventionally, but are expensive to manufacture and purchase. Other conventional solutions for combining personal data capture facilities often present numerous design and manufacturing problems such as size restrictions, specialized materials requirements, lowered tolerances for defects such as pits or holes in coverings for water-resistant or waterproof devices, unreliability, higher failure rates, increased manufacturing time, and expense. Subsequently, conventional devices such as fitness watches, heart rate monitors, GPS-enabled fitness monitors, health monitors (e.g., diabetic blood sugar testing units), digital voice recorders, pedometers, altimeters, and other conventional personal data capture devices are generally manufactured for conditions that occur in a single or small groupings of activities. Problematically, though, conventional devices do not provide effective solutions to users in terms of providing a comprehensive view of one's overall health or wellness as a result of a combined analysis of data gathered. This is a limiting aspect of the commercial attraction of the various types of conventional devices listed above.

Generally, if the number of activities performed by conventional personal data capture devices increases, there is a corresponding rise in design and manufacturing requirements that results in significant consumer expense, which eventually becomes prohibitive to both investment and commercialization. Further, conventional manufacturing techniques are often limited and ineffective at meeting increased requirements to protect sensitive hardware, circuitry, and other components that are susceptible to damage, but which are required to perform various personal data capture activities. As a conventional example, sensitive electronic components such as printed circuit board assemblies ("PCBA"), sensors, and computer memory (hereafter "memory") can be significantly damaged or destroyed during manufacturing processes where overmoldings or layering of protective material occurs using techniques such as injection molding, cold molding, and others. Damaged or destroyed items subsequently raises the cost of goods sold and can deter not only investment and commercialization, but also innovation in data capture and analysis technologies, which are highly compelling fields of opportunity.

Thus, what is needed is a solution for data capture devices without the limitations of conventional techniques.

BRIEF DESCRIPTION OF THE DRAWINGS

Various embodiments or examples ("examples") of the invention are disclosed in the following detailed description and the accompanying drawings.

DETAILED DESCRIPTION

Various embodiments or examples may be implemented in numerous ways, including as a system, a process, an apparatus, a user interface, or a series of program instructions on a computer readable medium such as a computer readable storage medium or a computer network where the program instructions are sent over optical, electronic, or wireless communication links. In general, operations of disclosed processes may be performed in an arbitrary order, unless otherwise provided in the claims.

A detailed description of one or more examples is provided below along with accompanying figures. The detailed description is provided in connection with such examples, but is not limited to any particular example. The scope is limited only by the claims and numerous alternatives, modifications, and equivalents are encompassed. Numerous specific details are set forth in the following description in order to provide a thorough understanding. These details are provided for the purpose of example and the described techniques may be practiced according to the claims without some or all of these specific details. For clarity, technical material that is known in the technical fields related to the examples has not been described in detail to avoid unnecessarily obscuring the description.

Figure 1:
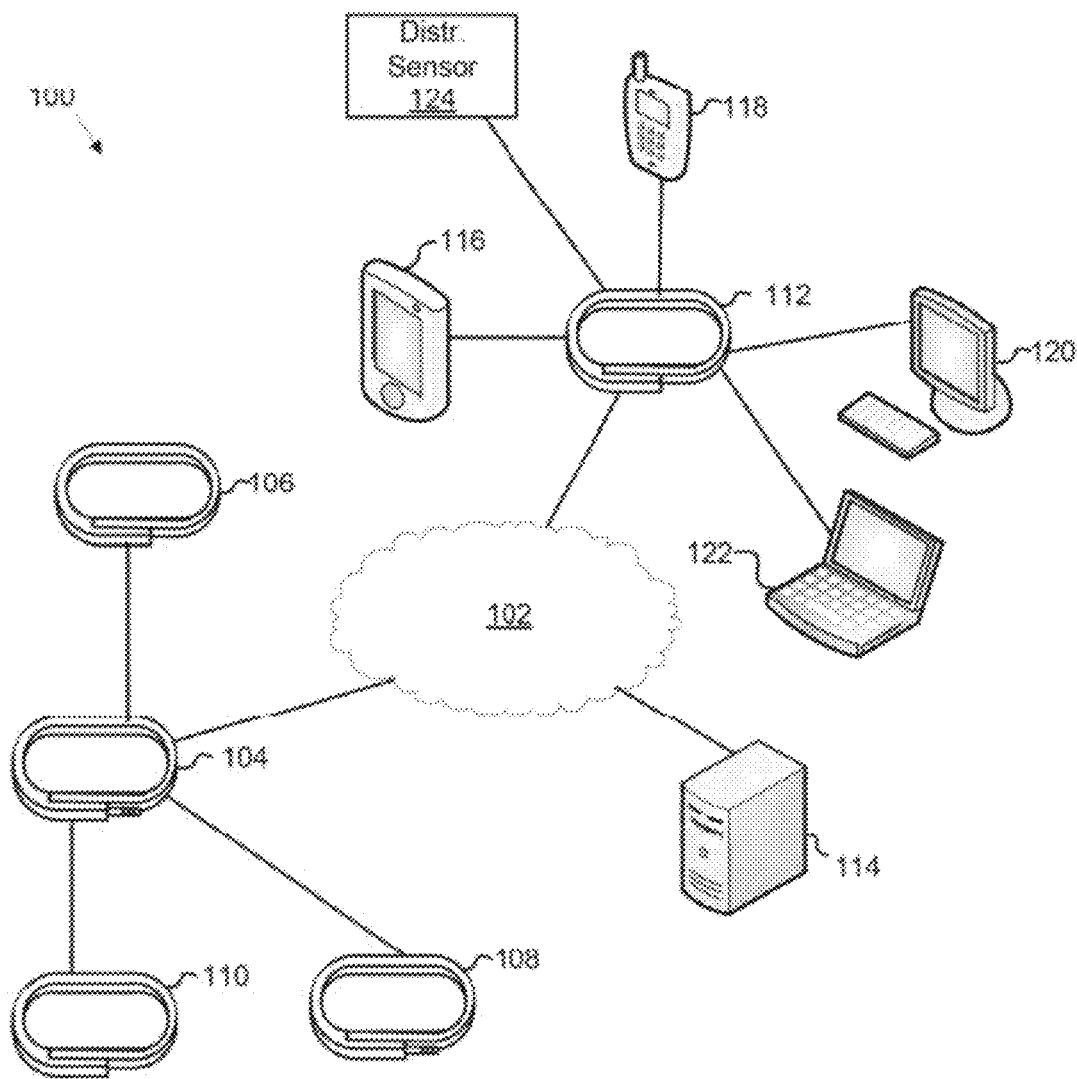
FIG. 1 illustrates an exemplary data-capable band system.

FIG. 1 illustrates an exemplary data-capable band system. Here, system 100 includes network 102, bands 104-112, server 114, mobile computing device 116, mobile communications device 118, computer 120, laptop 122, and distributed sensor 124. Bands 104-112 may be implemented as data-capable device that may be worn as a strap or band around an arm, leg, ankle, or other bodily appendage or feature. In other examples, bands 104-112 may be attached directly or indirectly to other items, organic or inorganic, animate, or static. In still other examples, bands 104-112 may be used differently.

As described above, bands 104-112 may be implemented as wearable personal data or data capture devices (e.g., data-capable devices) that are worn by a user around a wrist, ankle, arm, ear, or other appendage, or attached to the body or affixed to clothing. One or more facilities, sensing elements, or sensors, both active and passive, may be implemented as part of bands 104-112 in order to capture various types of data from different sources. Temperature, environmental, temporal, motion, electronic, electrical, chemical, or other types of sensors (including those described below in connection with FIG. 3) may be used in order to gather varying amounts of data, which may be configurable by a user, locally (e.g., using user interface facilities such as buttons, switches, motion-activated/detected command structures (e.g., accelerometer-gathered data from user-initiated motion of bands 104-112), and others) or remotely (e.g., entering rules or parameters in a website or graphical user interface ("GUI") that may be used to modify control systems or signals in firmware, circuitry, hardware, and software implemented (i.e., installed) on bands 104-112). Bands 104-112 may also be implemented as data-capable devices that are configured for data communication using various types of communications infrastructure and media, as described in greater detail below. Bands 104-112 may also be wearable, personal, non-intrusive, lightweight devices that are configured to gather large amounts of personally relevant data that can be used to improve user health, fitness levels, medical conditions, athletic performance, sleeping physiology, and physiological conditions, or used as a sensory-based user interface ("UI") to signal social-related notifications specifying the state of the user through vibration, heat, lights or other sensory based notifications. For example, a social-related notification signal indicating a user is on-line can be transmitted to a recipient, who in turn, receives the notification as, for instance, a vibration.

Using data gathered by bands 104-112, applications may be used to perform various analyses and evaluations that can generate information as to a person's physical (e.g., healthy, sick, weakened, or other states, or activity level), emotional, or mental state (e.g., an elevated body temperature or heart rate may indicate stress, a lowered heart rate and skin temperature, or reduced movement (e.g., excessive sleeping), may indicate physiological depression caused by exertion or other factors, chemical data gathered from evaluating outgassing from the skin's surface may be analyzed to determine whether a person's diet is balanced or if various nutrients are lacking, salinity detectors may be evaluated to determine if high, lower, or proper blood sugar levels are present for diabetes management, and others). Generally, bands 104-112 may be configured to gather from sensors locally and remotely.

As an example, band 104 may capture (i.e., record, store, communicate (i.e., send or receive), process, or the like) data from various sources (i.e., sensors that are organic (i.e., installed, integrated, or otherwise implemented with band 104) or distributed (e.g., microphones on mobile computing device 116, mobile communications device 118, computer 120, laptop 122, distributed sensor 124, global positioning system ("GPS") satellites, or others, without limitation)) and exchange data with one or more of bands 106-112, server 114, mobile computing device 116, mobile communications device 118, computer 120, laptop 122, and distributed sensor 124. As shown here, a local sensor may be one that is incorporated, integrated, or otherwise implemented with bands 104-112. A remote or distributed sensor (e.g., mobile computing device 116, mobile communications device 118, computer 120, laptop 122, or, generally, distributed sensor 124) may be sensors that can be accessed, controlled, or otherwise used by bands 104-112. For example, band 112 may be configured to control devices that are also controlled by a given user (e.g., mobile computing device 116, mobile communications device 118, computer 120, laptop 122, and distributed sensor 124). For example, a microphone in mobile communications device 118 may be used to detect, for example, ambient audio data that is used to help identify a person's location, or an ear clip (e.g., a headset as described below) affixed to an ear may be used to record pulse or blood oxygen saturation levels. Additionally, a sensor implemented with a screen on mobile computing device 116 may be used to read a user's temperature or obtain a biometric signature while a user is interacting with data. A further example may include using data that is observed on computer 120 or laptop 122 that provides information as to a user's online behavior and the type of content that she is viewing, which may be used by bands 104-112. Regardless of the type or location of sensor used, data may be transferred to bands 104-112 by using, for example, an analog audio jack, digital adapter (e.g., USB, mini-USB), or other, without limitation, plug, or other type of connector that may be used to physically couple bands 104-112 to another device or system for transferring data and, in some examples, to provide power to recharge a battery (not shown). Alternatively, a wireless data communication interface or facility (e.g., a wireless radio that is configured to communicate data from bands 104-112 using one or more data communication protocols (e.g., IEEE 802.11a/b/g/n (WiFi), WiMax, ANT™, ZigBee®, Bluetooth®, Near Field Communications ("NFC"), and others)) may be used to receive or transfer data. Further, bands 104-112 may be configured to analyze, evaluate, modify, or otherwise use data gathered, either directly or indirectly.

In some examples, bands 104-112 may be configured to share data with each other or with an intermediary facility, such as a database, website, web service, or the like, which may be implemented by server 114. In some embodiments, server 114 can be operated by a third party providing, for example, social media-related services. Bands 104-112 and other related devices may exchange data with each other directly, or bands 104-112 may exchange data via a third party server, such as a third party like Facebook®, to provide social-media related services. Examples of other third party servers include those implemented by social networking services, including, but not limited to, services such as Yahoo! IM™, GTalk™, MSN Messenger™, Twitter® and other private or public social networks. The exchanged data may include personal physiological data and data derived from sensory-based user interfaces ("UI"). Server 114, in some examples, may be implemented using one or more processor-based computing devices or networks, including computing clouds, storage area networks ("SAN"), or the like. As shown, bands 104-112 may be used as a personal data or area network (e.g., "PDN" or "PAN") in which data relevant to a given user or band (e.g., one or more of bands 104-112) may be shared. As shown here, bands 104 and 112 may be configured to exchange data with each other over network 102 or indirectly using server 114. Users of bands 104 and 112 may direct a web browser hosted on a computer (e.g., computer 120, laptop 122, or the like) in order to access, view, modify, or perform other operations with data captured by bands 104 and 112. For example, two runners using bands 104 and 112 may be geographically remote (e.g., users are not geographically in close proximity locally such that bands being used by each user are in direct data communication), but wish to share data regarding their race times (pre, post, or in-race), personal records (i.e., "PR"), target split times, results, performance characteristics (e.g., target heart rate, target VO2 max, and others), and other information. If both runners (i.e., bands 104 and 112) are engaged in a race on the same day, data can be gathered for comparative analysis and other uses. Further, data can be shared in substantially real-time (taking into account any latencies incurred by data transfer rates, network topologies, or other data network factors) as well as uploaded after a given activity or event has been performed. In other words, data can be captured by the user as it is worn and configured to transfer data using, for example, a wireless network connection (e.g., a wireless network interface card, wireless local area network ("LAN") card, cell phone, or the like). Data may also be shared in a temporally asynchronous manner in which a wired data connection (e.g., an analog audio plug (and associated software or firmware) configured to transfer digitally encoded data to encoded audio data that may be transferred between bands 104-112 and a plug configured to receive, encode/decode, and process data exchanged) may be used to transfer data from one or more bands 104-112 to various destinations (e.g., another of bands 104-112, server 114, mobile computing device 116, mobile communications device 118, computer 120, laptop 122, and distributed sensor 124). Bands 104-112 may be implemented with various types of wired and/or wireless communication facilities and are not intended to be limited to any specific technology. For example, data may be transferred from bands 104-112 using an analog audio plug (e.g., TRRS, TRS, or others). In other examples, wireless communication facilities using various types of data communication protocols (e.g., WiFi, Bluetooth®, ZigBee®, ANT™, and others) may be implemented as part of bands 104-112, which may include circuitry, firmware, hardware, radios, antennas, processors, microprocessors, memories, or other electrical, electronic, mechanical, or physical elements configured to enable data communication capabilities of various types and characteristics.

As data-capable devices, bands 104-112 may be configured to collect data from a wide range of sources, including onboard (not shown) and distributed sensors (e.g., server 114, mobile computing device 116, mobile communications device 118, computer 120, laptop 122, and distributed sensor 124) or other bands. Some or all data captured may be personal, sensitive, or confidential and various techniques for providing secure storage and access may be implemented. For example, various types of security protocols and algorithms may be used to encode data stored or accessed by bands 104-112. Examples of security protocols and algorithms include authentication, encryption, encoding, private and public key infrastructure, passwords, checksums, hash codes and hash functions (e.g., SHA, SHA-1, MD-5, and the like), or others may be used to prevent undesired access to data captured by bands 104-112. In other examples, data security for bands 104-112 may be implemented differently.

Bands 104-112 may be used as personal wearable, data capture devices that, when worn, are configured to identify a specific, individual user. By evaluating captured data such as motion data from an accelerometer, biometric data such as heart rate, skin galvanic response, and other biometric data, and using long-term analysis techniques (e.g., software packages or modules of any type, without limitation), a user may have a unique pattern of behavior or motion and/or biometric responses that can be used as a signature for identification. For example, bands 104-112 may gather data regarding an individual person's gait or other unique biometric, physiological or behavioral characteristics. Using, for example, distributed sensor 124, a biometric signature (e.g., fingerprint, retinal or iris vascular pattern, or others) may be gathered and transmitted to bands 104-112 that, when combined with other data, determines that a given user has been properly identified and, as such, authenticated. When bands 104-112 are worn, a user may be identified and authenticated to enable a variety of other functions such as accessing or modifying data, enabling wired or wireless data transmission facilities (i.e., allowing the transfer of data from bands 104-112), modifying functionality or functions of bands 104-112, authenticating financial transactions using stored data and information (e.g., credit card, PIN, card security numbers, and the like), running applications that allow for various operations to be performed (e.g., controlling physical security and access by transmitting a security code to a reader that, when authenticated, unlocks a door by turning off current to an electromagnetic lock, and others), and others. Different functions and operations beyond those described may be performed using bands 104-112, which can act as secure, personal, wearable, data-capable devices. The number, type, function, configuration, specifications, structure, or other features of system 100 and the above-described elements may be varied and are not limited to the examples provided.

Figure 2:
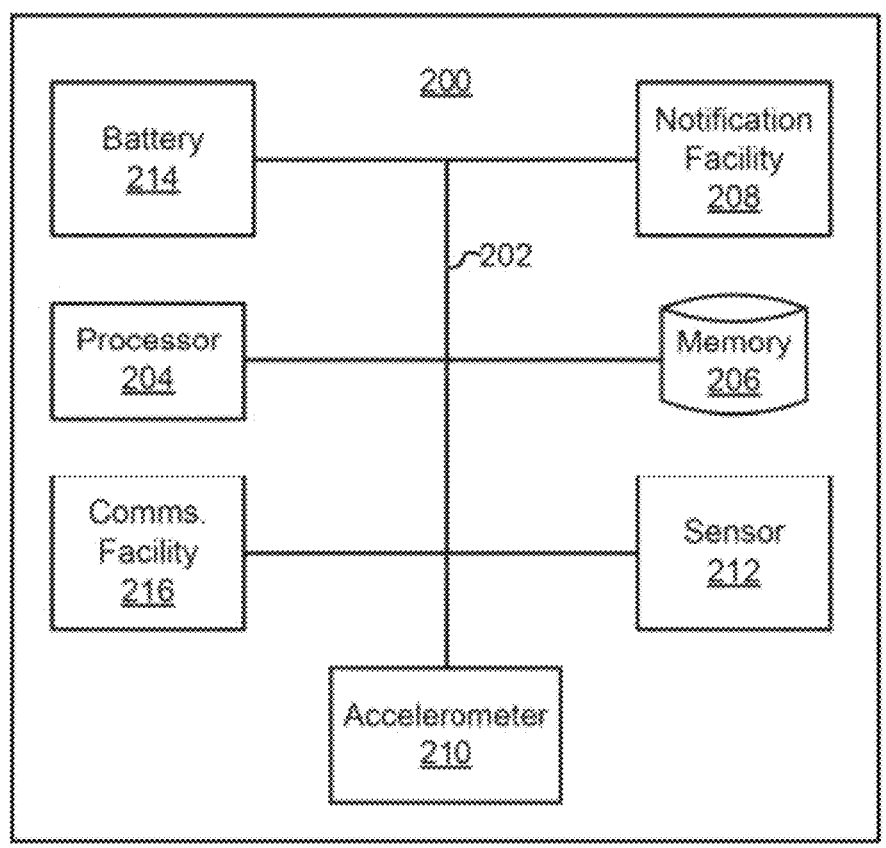
FIG. 2 illustrates a block diagram of an exemplary data-capable band.

FIG. 2 illustrates a block diagram of an exemplary data-capable band. Here, band 200 includes bus 202, processor 204, memory 206, notification facility 208, accelerometer 210, sensor 212, battery 214, and communications facility 216. In some examples, the quantity, type, function, structure, and configuration of band 200 and the elements (e.g., bus 202, processor 204, memory 206, notification facility 208, accelerometer 210, sensor 212, battery 214, and communications facility 216) shown may be varied and are not limited to the examples provided. As shown, processor 204 may be implemented as logic to provide control functions and signals to memory 206, notification facility 208, accelerometer 210, sensor 212, battery 214, and communications facility 216. Processor 204 may be implemented using any type of processor or microprocessor suitable for packaging within bands 104-112 (FIG. 1). Various types of microprocessors may be used to provide data processing capabilities for band 200 and are not limited to any specific type or capability. For example, a MSP430F5528-type microprocessor manufactured by Texas Instruments of Dallas, Tex. may be configured for data communication using audio tones and enabling the use of an audio plug-and-jack system (e.g., TRRS, TRS, or others) for transferring data captured by band 200. Further, different processors may be desired if other functionality (e.g., the type and number of sensors (e.g., sensor 212)) are varied. Data processed by processor 204 may be stored using, for example, memory 206.

In some examples, memory 206 may be implemented using various types of data storage technologies and standards, including, without limitation, read-only memory ("ROM"), random access memory ("RAM"), dynamic random access memory ("DRAM"), static random access memory ("SRAM"), static/dynamic random access memory ("SDRAM"), magnetic random access memory ("MRAM"), solid state, two and three-dimensional memories, Flash®, and others. Memory 206 may also be implemented using one or more partitions that are configured for multiple types of data storage technologies to allow for non-modifiable (i.e., by a user) software to be installed (e.g., firmware installed on ROM) while also providing for storage of captured data and applications using, for example, RAM. Once captured and/or stored in memory 206, data may be subjected to various operations performed by other elements of band 200.

Notification facility 208, in some examples, may be implemented to provide vibratory energy, audio or visual signals, communicated through band 200. As used herein, "facility" refers to any, some, or all of the features and structures that are used to implement a given set of functions. In some examples, the vibratory energy may be implemented using a motor or other mechanical structure. In some examples, the audio signal may be a tone or other audio cue, or it may be implemented using different sounds for different purposes. The audio signals may be emitted directly using notification facility 208, or indirectly by transmission via communications facility 216 to other audio-capable devices (e.g., headphones (not shown), a headset (as described below with regard to FIG. 12), mobile computing device 116, mobile communications device 118, computer 120, laptop 122, distributed sensor 124, etc.). In some examples, the visual signal may be implemented using any available display technology, such as lights, light-emitting diodes (LEDs), interferometric modulator display (IMOD), electrophoretic ink (E Ink), organic light-emitting diode (OLED), or other display technologies. As an example, an application stored on memory 206 may be configured to monitor a clock signal from processor 204 in order to provide timekeeping functions to band 200. For example, if an alarm is set for a desired time, notification facility 208 may be used to provide a vibration or an audio tone, or a series of vibrations or audio tones, when the desired time occurs. As another example, notification facility 208 may be coupled to a framework (not shown) or other structure that is used to translate or communicate vibratory energy throughout the physical structure of band 200. In other examples, notification facility 208 may be implemented differently.

Power may be stored in battery 214, which may be implemented as a battery, battery module, power management module, or the like. Power may also be gathered from local power sources such as solar panels, thermo-electric generators, and kinetic energy generators, among others that are alternatives power sources to external power for a battery. These additional sources can either power the system directly or can charge a battery, which, in turn, is used to power the system (e.g., of a band). In other words, battery 214 may include a rechargeable, expendable, replaceable, or other type of battery, but also circuitry, hardware, or software that may be used in connection with in lieu of processor 204 in order to provide power management, charge/recharging, sleep, or other functions. Further, battery 214 may be implemented using various types of battery technologies, including Lithium Ion ("LI"), Nickel Metal Hydride ("NiMH"), or others, without limitation. Power drawn as electrical current may be distributed from battery via bus 202, the latter of which may be implemented as deposited or formed circuitry or using other forms of circuits or cabling, including flexible circuitry. Electrical current distributed from battery 204 and managed by processor 204 may be used by one or more of memory 206, notification facility 208, accelerometer 210, sensor 212, or communications facility 216.

As shown, various sensors may be used as input sources for data captured by band 200. For example, accelerometer 210 may be used to gather data measured across one, two, or three axes of motion. In addition to accelerometer 210, other sensors (i.e., sensor 212) may be implemented to provide temperature, environmental, physical, chemical, electrical, or other types of sensed inputs. As presented here, sensor 212 may include one or multiple sensors and is not intended to be limiting as to the quantity or type of sensor implemented. Data captured by band 200 using accelerometer 210 and sensor 212 or data requested from another source (i.e., outside of band 200) may also be exchanged, transferred, or otherwise communicated using communications facility 216. For example, communications facility 216 may include a wireless radio, control circuit or logic, antenna, transceiver, receiver, transmitter, resistors, diodes, transistors, or other elements that are used to transmit and receive data from band 200. In some examples, communications facility 216 may be implemented to provide a "wired" data communication capability such as an analog or digital attachment, plug, jack, or the like to allow for data to be transferred. In other examples, communications facility 216 may be implemented to provide a wireless data communication capability to transmit digitally encoded data across one or more frequencies using various types of data communication protocols, without limitation. In still other examples, band 200 and the above-described elements may be varied in function, structure, configuration, or implementation and are not limited to those shown and described.

Figure 3:
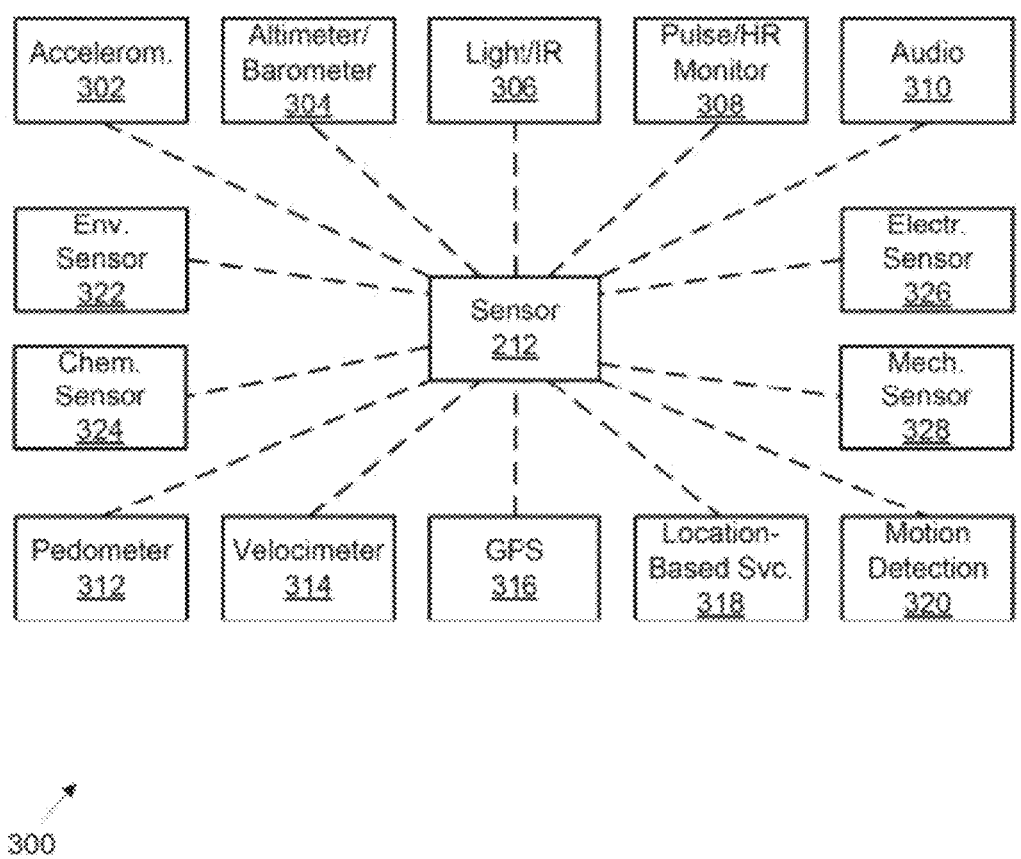
FIG. 3 illustrates sensors for use with an exemplary data-capable band.

FIG. 3 illustrates sensors for use with an exemplary data-capable band. Sensor 212 may be implemented using various types of sensors, some of which are shown. Like-numbered and named elements may describe the same or substantially similar element as those shown in other descriptions. Here, sensor 212 (FIG. 2) may be implemented as accelerometer 302, altimeter/barometer 304, light/infrared ("IR") sensor 306, pulse/heart rate ("HR") monitor 308, audio sensor (e.g., microphone, transducer, or others) 310, pedometer 312, velocimeter 314, GPS receiver 316, location-based service sensor (e.g., sensor for determining location within a cellular or micro-cellular network, which may or may not use GPS or other satellite constellations for fixing a position) 318, motion detection sensor 320, environmental sensor 322, chemical sensor 324, electrical sensor 326, or mechanical sensor 328.

As shown, accelerometer 302 may be used to capture data associated with motion detection along 1, 2, or 3-axes of measurement, without limitation to any specific type of specification of sensor. Accelerometer 302 may also be implemented to measure various types of user motion and may be configured based on the type of sensor, firmware, software, hardware, or circuitry used. As another example, altimeter/barometer 304 may be used to measure environment pressure, atmospheric or otherwise, and is not limited to any specification or type of pressure-reading device. In some examples, altimeter/barometer 304 may be an altimeter, a barometer, or a combination thereof. For example, altimeter/barometer 304 may be implemented as an altimeter for measuring above ground level ("AGL") pressure in band 200, which has been configured for use by naval or military aviators. As another example, altimeter/barometer 304 may be implemented as a barometer for reading atmospheric pressure for marine-based applications. In other examples, altimeter/barometer 304 may be implemented differently.

Other types of sensors that may be used to measure light or photonic conditions include light/IR sensor 306, motion detection sensor 320, and environmental sensor 322, the latter of which may include any type of sensor for capturing data associated with environmental conditions beyond light. Further, motion detection sensor 320 may be configured to detect motion using a variety of techniques and technologies, including, but not limited to comparative or differential light analysis (e.g., comparing foreground and background lighting), sound monitoring, or others. Audio sensor 310 may be implemented using any type of device configured to record or capture sound.

In some examples, pedometer 312 may be implemented using devices to measure various types of data associated with pedestrian-oriented activities such as running or walking. Footstrikes, stride length, stride length or interval, time, and other data may be measured. Velocimeter 314 may be implemented, in some examples, to measure velocity (e.g., speed and directional vectors) without limitation to any particular activity. Further, additional sensors that may be used as sensor 212 include those configured to identify or obtain location-based data. For example, GPS receiver 316 may be used to obtain coordinates of the geographic location of band 200 using, for example, various types of signals transmitted by civilian and/or military satellite constellations in low, medium, or high earth orbit (e.g., "LEO," "MEO," or "GEO"). In other examples, differential GPS algorithms may also be implemented with GPS receiver 316, which may be used to generate more precise or accurate coordinates. Still further, location-based services sensor 318 may be implemented to obtain location-based data including, but not limited to location, nearby services or items of interest, and the like. As an example, location-based services sensor 318 may be configured to detect an electronic signal, encoded or otherwise, that provides information regarding a physical locale as band 200 passes. The electronic signal may include, in some examples, encoded data regarding the location and information associated therewith. Electrical sensor 326 and mechanical sensor 328 may be configured to include other types (e.g., haptic, kinetic, piezoelectric, piezomechanical, pressure, touch, thermal, and others) of sensors for data input to band 200, without limitation. Other types of sensors apart from those shown may also be used, including magnetic flux sensors such as solid-state compasses and the like, including gyroscopic sensors. While the present illustration provides numerous examples of types of sensors that may be used with band 200 (FIG. 2), others not shown or described may be implemented with or as a substitute for any sensor shown or described.

Figure 4:
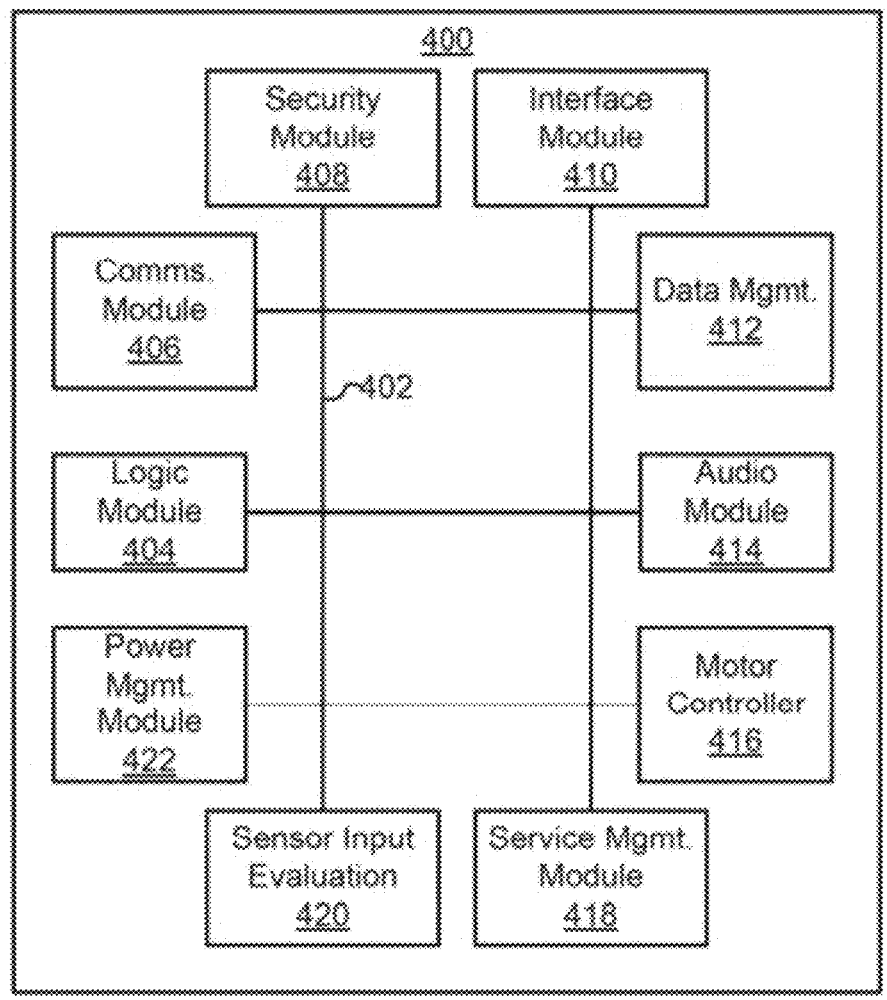
FIG. 4 illustrates an application architecture for an exemplary data-capable band.

FIG. 4 illustrates an application architecture for an exemplary data-capable band. Here, application architecture 400 includes bus 402, logic module 404, communications module 406, security module 408, interface module 410, data management 412, audio module 414, motor controller 416, service management module 418, sensor input evaluation module 420, and power management module 422. In some examples, application architecture 400 and the above-listed elements (e.g., bus 402, logic module 404, communications module 406, security module 408, interface module 410, data management 412, audio module 414, motor controller 416, service management module 418, sensor input evaluation module 420, and power management module 422) may be implemented as software using various computer programming and formatting languages such as Java, C++, C, and others. As shown here, logic module 404 may be firmware or application software that is installed in memory 206 (FIG. 2) and executed by processor 204 (FIG. 2). Included with logic module 404 may be program instructions or code (e.g., source, object, binary executables, or others) that, when initiated, called, or instantiated, perform various functions.

For example, logic module 404 may be configured to send control signals to communications module 406 in order to transfer, transmit, or receive data stored in memory 206, the latter of which may be managed by a database management system ("DBMS") or utility in data management module 412. As another example, security module 408 may be controlled by logic module 404 to provide encoding, decoding, encryption, authentication, or other functions to band 200 (FIG. 2). Alternatively, security module 408 may also be implemented as an application that, using data captured from various sensors and stored in memory 206 (and accessed by data management module 412) may be used to provide identification functions that enable band 200 to passively identify a user or wearer of band 200. Still further, various types of security software and applications may be used and are not limited to those shown and described.

Interface module 410, in some examples, may be used to manage user interface controls such as switches, buttons, or other types of controls that enable a user to manage various functions of band 200. For example, a 4-position switch may be turned to a given position that is interpreted by interface module 410 to determine the proper signal or feedback to send to logic module 404 in order to generate a particular result. In other examples, a button (not shown) may be depressed that allows a user to trigger or initiate certain actions by sending another signal to logic module 404. Still further, interface module 410 may be used to interpret data from, for example, accelerometer 210 (FIG. 2) to identify specific movement or motion that initiates or triggers a given response. In other examples, interface module 410 may be used to manage different types of displays (e.g., LED, IMOD, E Ink, OLED, etc.). In other examples, interface module 410 may be implemented differently in function, structure, or configuration and is not limited to those shown and described.

As shown, audio module 414 may be configured to manage encoded or unencoded data gathered from various types of audio sensors. In some examples, audio module 414 may include one or more codecs that are used to encode or decode various types of audio waveforms. For example, analog audio input may be encoded by audio module 414 and, once encoded, sent as a signal or collection of data packets, messages, segments, frames, or the like to logic module 404 for transmission via communications module 406. In other examples, audio module 414 may be implemented differently in function, structure, configuration, or implementation and is not limited to those shown and described. Other elements that may be used by band 200 include motor controller 416, which may be firmware or an application to control a motor or other vibratory energy source (e.g., notification facility 208 (FIG. 2)). Power used for band 200 may be drawn from battery 214 (FIG. 2) and managed by power management module 422, which may be firmware or an application used to manage, with or without user input, how power is consumer, conserved, or otherwise used by band 200 and the above-described elements, including one or more sensors (e.g., sensor 212 (FIG. 2), sensors 302-328 (FIG. 3)). With regard to data captured, sensor input evaluation module 420 may be a software engine or module that is used to evaluate and analyze data received from one or more inputs (e.g., sensors 302-328) to band 200. When received, data may be analyzed by sensor input evaluation module 420, which may include custom or "off-the-shelf" analytics packages that are configured to provide application-specific analysis of data to determine trends, patterns, and other useful information. In other examples, sensor input module 420 may also include firmware or software that enables the generation of various types and formats of reports for presenting data and any analysis performed thereupon.

Another element of application architecture 400 that may be included is service management module 418. In some examples, service management module 418 may be firmware, software, or an application that is configured to manage various aspects and operations associated with executing software-related instructions for band 200. For example, libraries or classes that are used by software or applications on band 200 may be served from an online or networked source. Service management module 418 may be implemented to manage how and when these services are invoked in order to ensure that desired applications are executed properly within application architecture 400. As discrete sets, collections, or groupings of functions, services used by band 200 for various purposes ranging from communications to operating systems to call or document libraries may be managed by service management module 418. Alternatively, service management module 418 may be implemented differently and is not limited to the examples provided herein. Further, application architecture 400 is an example of a software/system/application-level architecture that may be used to implement various software-related aspects of band 200 and may be varied in the quantity, type, configuration, function, structure, or type of programming or formatting languages used, without limitation to any given example.

Figure 5A:
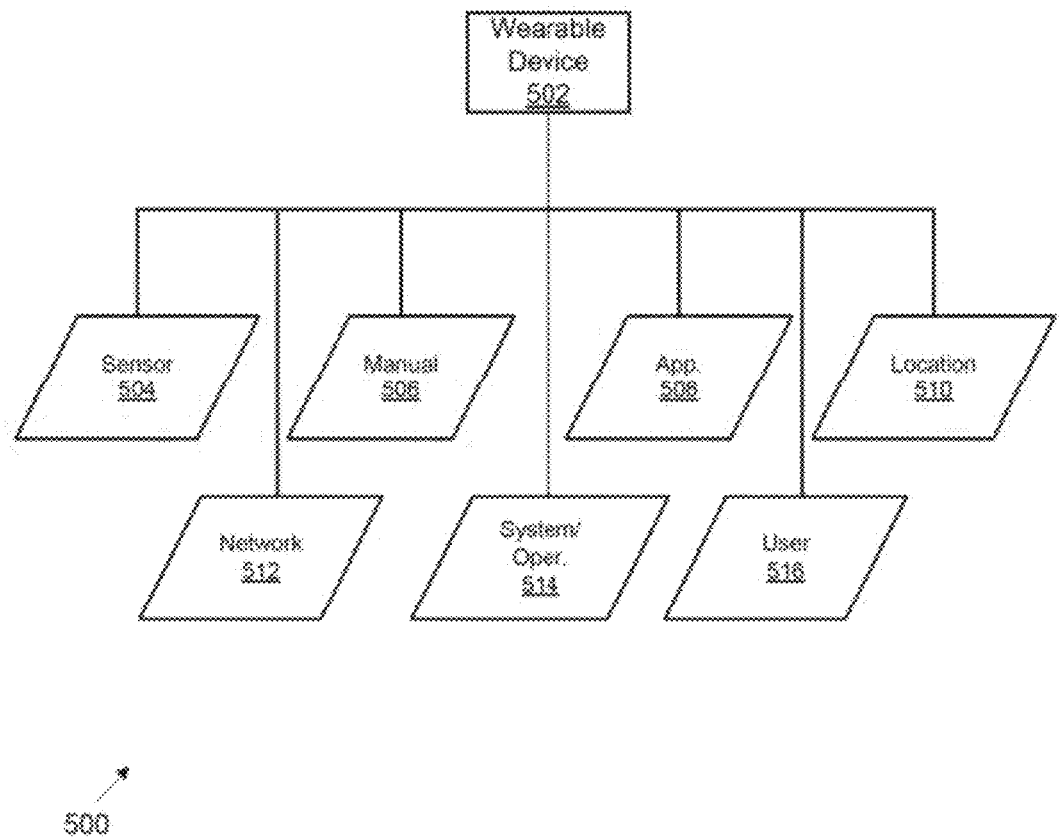
FIG. 5A illustrates representative data types for use with an exemplary data-capable band.

FIG. 5A illustrates representative data types for use with an exemplary data-capable band. Here, wearable device 502 may capture various types of data, including, but not limited to sensor data 504, manually-entered data 506, application data 508, location data 510, network data 512, system/operating data 514, and user data 516. Various types of data may be captured from sensors, such as those described above in connection with FIG. 3. Manually-entered data, in some examples, may be data or inputs received directly and locally by band 200 (FIG. 2). In other examples, manually-entered data may also be provided through a third-party website that stores the data in a database and may be synchronized from server 114 (FIG. 1) with one or more of bands 104-112. Other types of data that may be captured including application data 508 and system/operating data 514, which may be associated with firmware, software, or hardware installed or implemented on band 200. Further, location data 510 may be used by wearable device 502, as described above. User data 516, in some examples, may be data that include profile data, preferences, rules, or other information that has been previously entered by a given user of wearable device 502. Further, network data 512 may be data is captured by wearable device with regard to routing tables, data paths, network or access availability (e.g., wireless network access availability), and the like. Other types of data may be captured by wearable device 502 and are not limited to the examples shown and described. Additional context-specific examples of types of data captured by bands 104-112 (FIG. 1) are provided below.

Figure 5B:
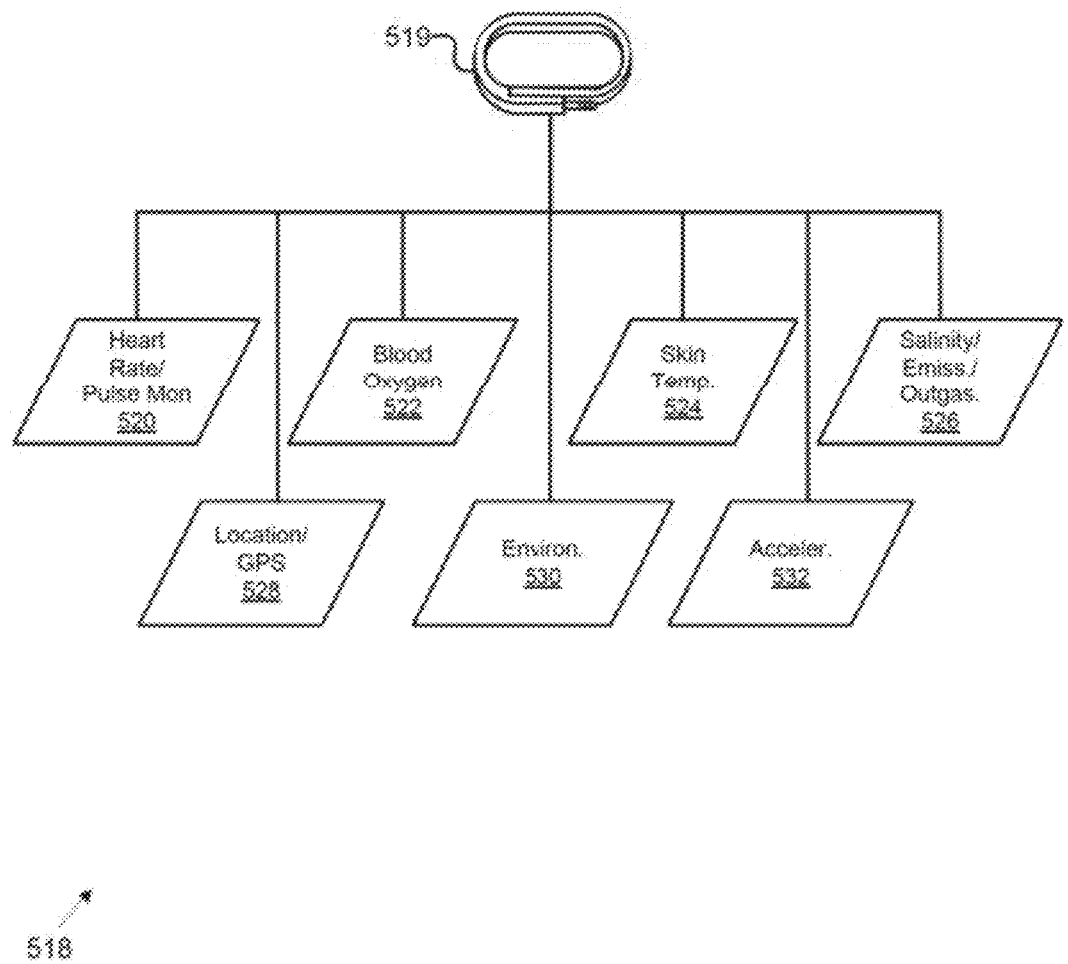
FIG. 5B illustrates representative data types for use with an exemplary data-capable band in fitness-related activities.

FIG. 5B illustrates representative data types for use with an exemplary data-capable band in fitness-related activities. Here, band 519 may be configured to capture types (i.e., categories) of data such as heart rate/pulse monitoring data 520, blood oxygen saturation data 522, skin temperature data 524, salinity/emission/outgassing data 526, location/GPS data 528, environmental data 530, and accelerometer data 532. As an example, a runner may use or wear band 519 to obtain data associated with his physiological condition (i.e., heart rate/pulse monitoring data 520, skin temperature, salinity/emission/outgassing data 526, among others), athletic efficiency (i.e., blood oxygen saturation data 522), and performance (i.e., location/GPS data 528 (e.g., distance or laps run), environmental data 530 (e.g., ambient temperature, humidity, pressure, and the like), accelerometer 532 (e.g., biomechanical information, including gait, stride, stride length, among others)). Other or different types of data may be captured by band 519, but the above-described examples are illustrative of some types of data that may be captured by band 519. Further, data captured may be uploaded to a website or online/networked destination for storage and other uses. For example, fitness-related data may be used by applications that are downloaded from a "fitness marketplace" or "wellness marketplace," where athletes, or other users, may find, purchase, or download applications, products, information, etc., for various uses, as well as share information with other users. Some applications may be activity-specific and thus may be used to modify or alter the data capture capabilities of band 519 accordingly. For example, a fitness marketplace may be a website accessible by various types of mobile and non-mobile clients to locate applications for different exercise or fitness categories such as running, swimming, tennis, golf, baseball, football, fencing, and many others. When downloaded, applications from a fitness marketplace may also be used with user-specific accounts to manage the retrieved applications as well as usage with band 519, or to use the data to provide services such as online personal coaching or targeted advertisements. More, fewer, or different types of data may be captured for fitness-related activities.

In some examples, applications may be developed using various types of schema, including using a software development kit or providing requirements in a proprietary or open source software development regime. Applications may also be developed by using an application programming interface to an application marketplace in order for developers to design and build applications that can be downloaded on wearable devices (e.g., bands 104-106 (FIG. 1)). Alternatively, application can be developed for download and installation on devices that may be in data communication over a shared data link or network connection, wired or wireless. For example, an application may be downloaded onto mobile computing device 116 (FIG. 1) from server 114 (FIG. 1), which may then be installed and executed using data gathered from one or more sensors on band 104. Analysis, evaluation, or other operations performed on data gathered by an application downloaded from server 114 may be presented (i.e., displayed) on a graphical user interface (e.g., a micro web browser, WAP web browser, Java/Java-script-based web browser, and others, without limitation) on mobile computing device 116 or any other type of client. Users may, in some examples, search, find, retrieve, download, purchase, or otherwise obtain applications for various types of purposes from an application marketplace. Applications may be configured for various types of purposes and categories, without limitation. Examples of types of purposes include running, swimming, trail running, diabetic management, dietary, weight management, sleep management, caloric burn rate tracking, activity tracking, and others, without limitation. Examples of categories of applications may include fitness, wellness, health, medical, and others, without limitation. In other examples, applications for distribution via a marketplace or other download website or source may be implemented differently and is not limited to those described.

Figure 5C:
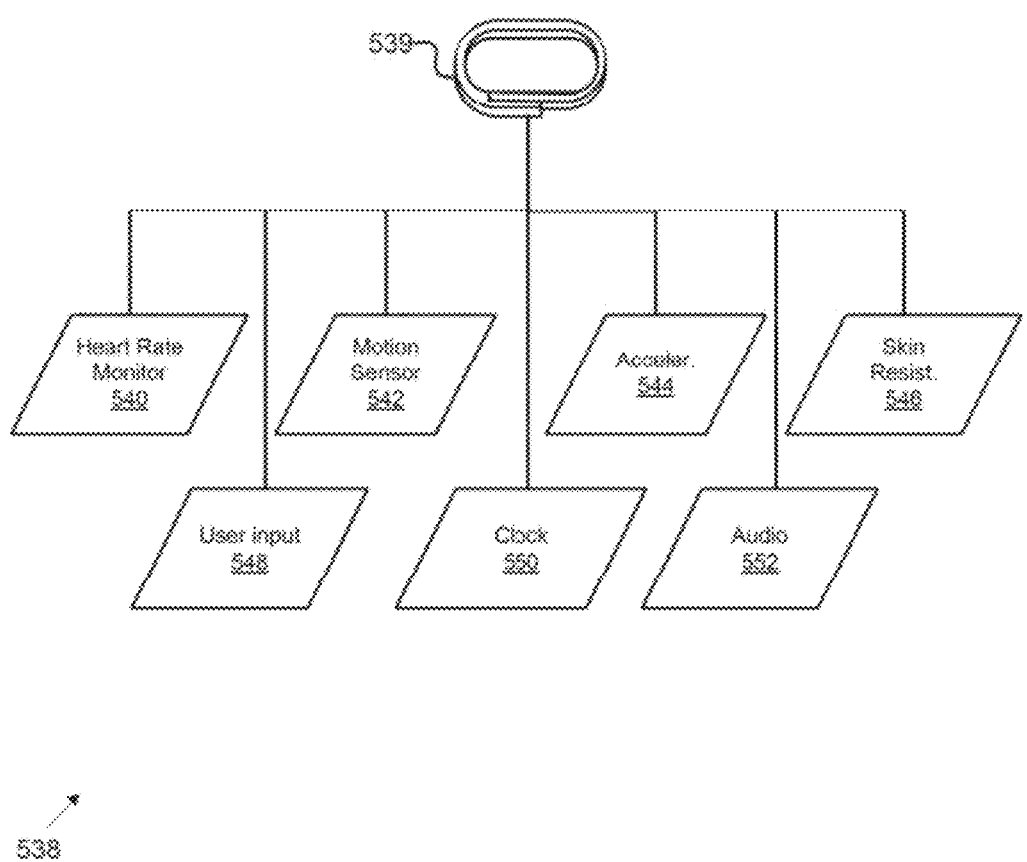
FIG. 5C illustrates representative data types for use with an exemplary data-capable band in sleep management activities.

FIG. 5C illustrates representative data types for use with an exemplary data-capable band in sleep management activities. Here, band 539 may be used for sleep management purposes to track various types of data, including heart rate monitoring data 540, motion sensor data 542, accelerometer data 544, skin resistivity data 546, user input data 548, clock data 550, and audio data 552. In some examples, heart rate monitor data 540 may be captured to evaluate rest, waking, or various states of sleep. Motion sensor data 542 and accelerometer data 544 may be used to determine whether a user of band 539 is experiencing a restful or fitful sleep. For example, some motion sensor data 542 may be captured by a light sensor that measures ambient or differential light patterns in order to determine whether a user is sleeping on her front, side, or back. Accelerometer data 544 may also be captured to determine whether a user is experiencing gentle or violent disruptions when sleeping, such as those often found in afflictions of sleep apnea or other sleep disorders. Further, skin resistivity data 546 may be captured to determine whether a user is ill (e.g., running a temperature, sweating, experiencing chills, clammy skin, and others). Still further, user input data may include data input by a user as to how and whether band 539 should trigger notification facility 208 (FIG. 2) to wake a user at a given time or whether to use a series of increasing or decreasing vibrations or audio tones to trigger a waking state. Clock data (550) may be used to measure the duration of sleep or a finite period of time in which a user is at rest. Audio data may also be captured to determine whether a user is snoring and, if so, the frequencies and amplitude therein may suggest physical conditions that a user may be interested in knowing (e.g., snoring, breathing interruptions, talking in one's sleep, and the like). More, fewer, or different types of data may be captured for sleep management-related activities.

Figure 5D:
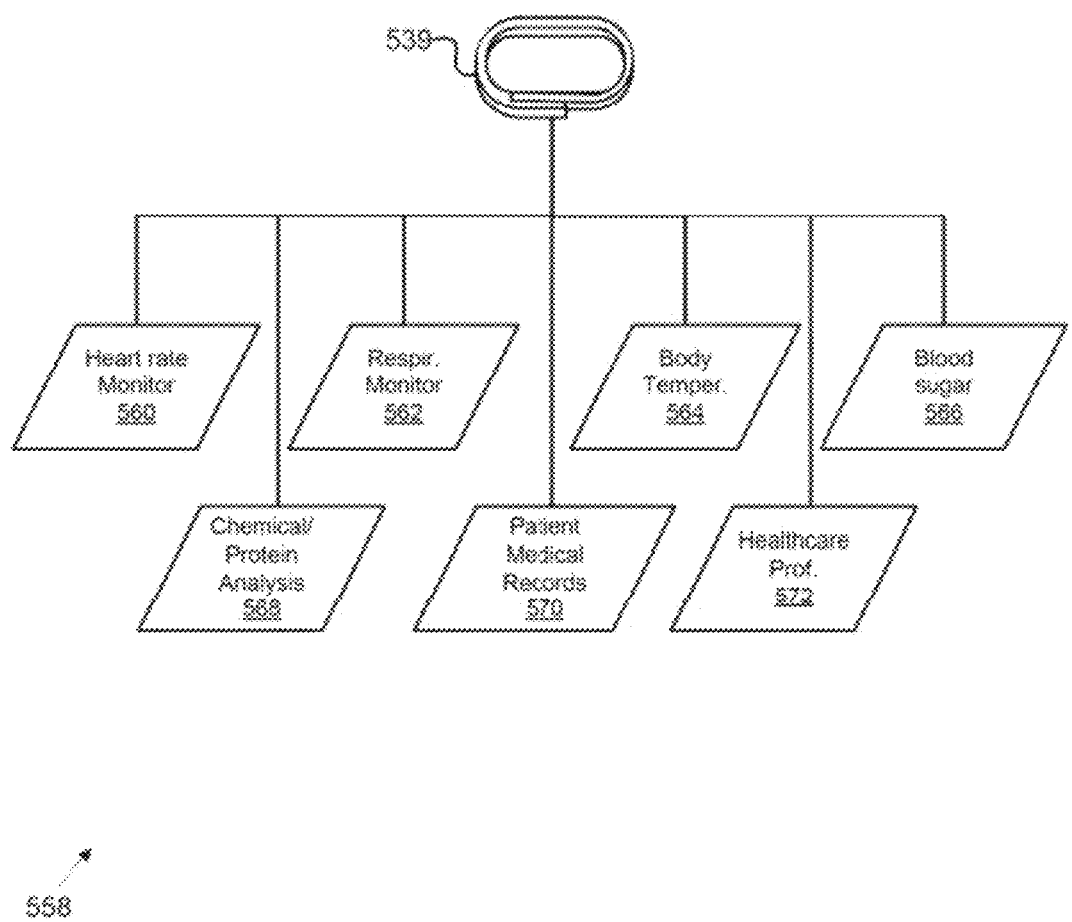
FIG. 5D illustrates representative data types for use with an exemplary data-capable band in medical-related activities.

FIG. 5D illustrates representative data types for use with an exemplary data-capable band in medical-related activities. Here, band 539 may also be configured for medical purposes and related-types of data such as heart rate monitoring data 560, respiratory monitoring data 562, body temperature data 564, blood sugar data 566, chemical protein/analysis data 568, patient medical records data 570, and healthcare professional (e.g., doctor, physician, registered nurse, physician's assistant, dentist, orthopedist, surgeon, and others) data 572. In some examples, data may be captured by band 539 directly from wear by a user. For example, band 539 may be able to sample and analyze sweat through a salinity or moisture detector to identify whether any particular chemicals, proteins, hormones, or other organic or inorganic compounds are present, which can be analyzed by band 539 or communicated to server 114 to perform further analysis. If sent to server 114, further analyses may be performed by a hospital or other medical facility using data captured by band 539. In other examples, more, fewer, or different types of data may be captured for medical-related activities.

Figure 5E:
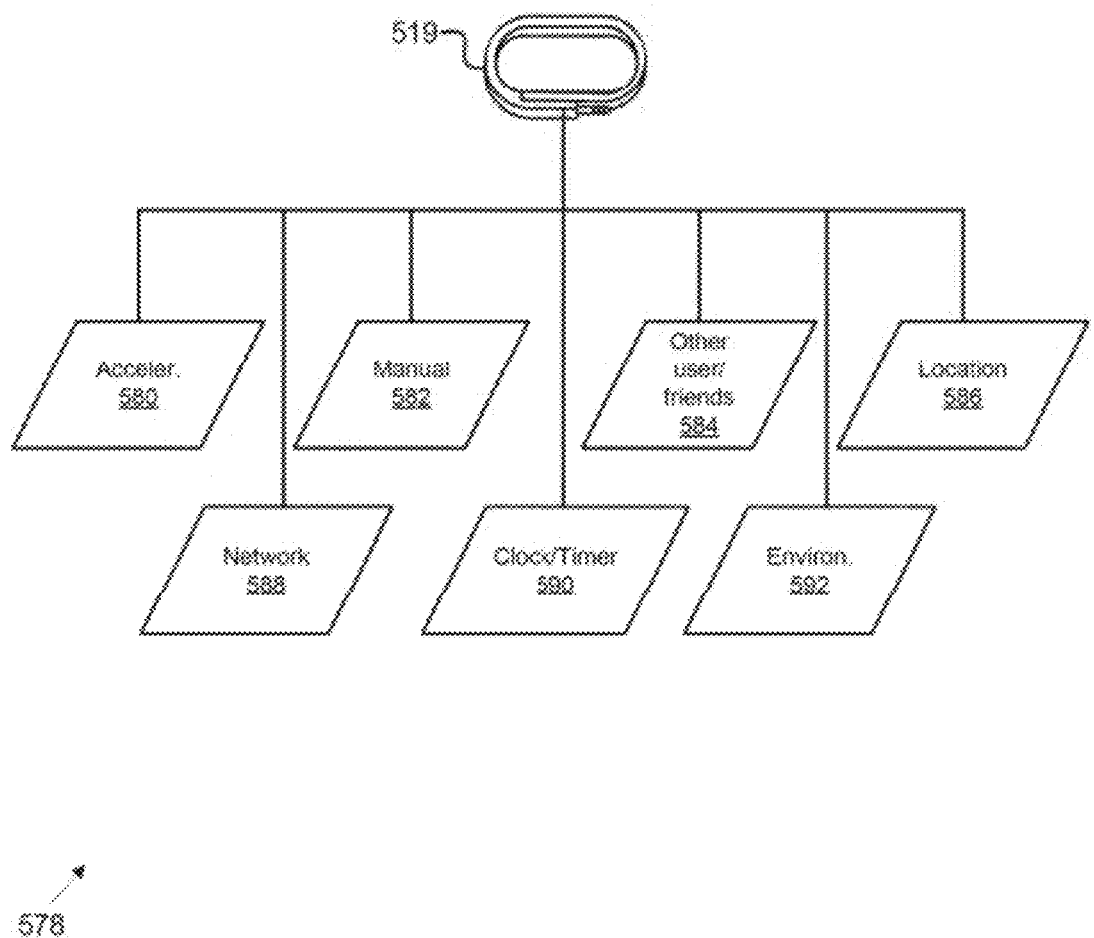
FIG. 5E illustrates representative data types for use with an exemplary data-capable band in social media/networking-related activities.

FIG. 5E illustrates representative data types for use with an exemplary data-capable band in social media/networking-related activities. Examples of social media/networking-related activities include activities related to Internet-based Social Networking Services ("SNS"), such as Facebook®, Twitter®, etc. Here, band 519, shown with an audio data plug, may be configured to capture data for use with various types of social media and networking-related services, websites, and activities. Accelerometer data 580, manual data 582, other user/friends data 584, location data 586, network data 588, clock/timer data 590, and environmental data 592 are examples of data that may be gathered and shared by, for example, uploading data from band 519 using, for example, an audio plug such as those described herein. As another example, accelerometer data 580 may be captured and shared with other users to share motion, activity, or other movement-oriented data. Manual data 582 may be data that a given user also wishes to share with other users. Likewise, other user/friends data 584 may be from other bands (not shown) that can be shared or aggregated with data captured by band 519. Location data 586 for band 519 may also be shared with other users. In other examples, a user may also enter manual data 582 to prevent other users or friends from receiving updated location data from band 519. Additionally, network data 588 and clock/timer data may be captured and shared with other users to indicate, for example, activities or events that a given user (i.e., wearing band 519) was engaged at certain locations. Further, if a user of band 519 has friends who are not geographically located in close or near proximity (e.g., the user of band 519 is located in San Francisco and her friend is located in Rome), environmental data can be captured by band 519 (e.g., weather, temperature, humidity, sunny or overcast (as interpreted from data captured by a light sensor and combined with captured data for humidity and temperature), among others). In other examples, more, fewer, or different types of data may be captured for medical-related activities.

Figure 6:
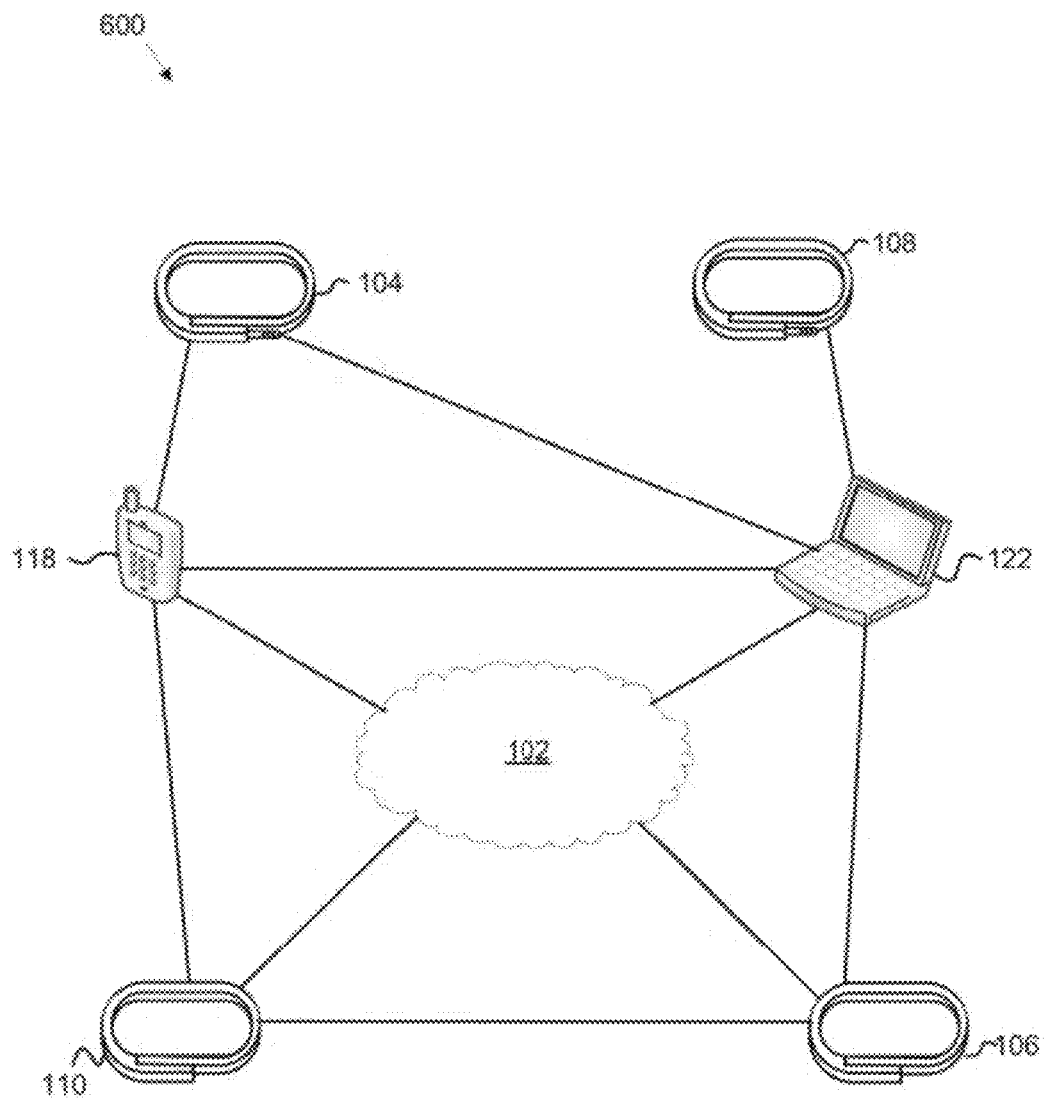
FIG. 6 illustrates an exemplary communications device system implemented with multiple exemplary data-capable bands.

FIG. 6 illustrates an exemplary communications device system implemented with multiple exemplary data-capable bands. The exemplary system 600 shows exemplary lines of communication between some of the devices shown in FIG. 1, including network 102, bands 104-110, mobile communications device 118, and laptop 122. In FIG. 6, examples of both peer-to-peer communication and peer-to-hub communication using bands 104-110 are shown. Using these avenues of communication, bands worn by multiple users or wearers (the term "wearer" is used herein to describe a user that is wearing one or more bands) may monitor and compare physical, emotional, mental states among wearers (e.g., physical competitions, sleep pattern comparisons, resting physical states, etc.).

Peer-to-hub communication may be exemplified by bands 104 and 108, each respectively communicating with mobile communications device 118 or laptop 122, exemplary hub devices. Bands 104 and 108 may communicate with mobile communications device 118 or laptop 122 using any number of known wired communication technologies (e.g., Universal Service Bus (USB) connections, TRS/TRRS connections, telephone networks, fiber-optic networks, cable networks, etc.). In some examples, bands 104 and 108 may be implemented as lower power or lower energy devices, in which case mobile communications device 118, laptop 122 or other hub devices may act as a gateway to route the data from bands 104 and 108 to software applications on the hub device, or to other devices. For example, mobile communications device 118 may comprise both wired and wireless communication capabilities, and thereby act as a hub to further communicate data received from band 104 to band 110, network 102 or laptop 122, among other devices. Mobile communications device 118 also may comprise software applications that interact with social or professional networking services ("SNS") (e.g., Facebook®, Twitter®, LinkedIn®, etc.), for example via network 102, and thereby act also as a hub to further share data received from band 104 with other users of the SNS. Band 104 may communicate with laptop 122, which also may comprise both wired and wireless communication capabilities, and thereby act as a hub to further communicate data received from band 104 to, for example, network 102 or laptop 122, among other devices. Laptop 122 also may comprise software applications that interact with SNS, for example via network 102, and thereby act also as a hub to further share data received from band 104 with other users of the SNS. The software applications on mobile communications device 118 or laptop 122 or other hub devices may further process or analyze the data they receive from bands 104 and 108 in order to present to the wearer, or to other wearers or users of the SNS, useful information associated with the wearer's activities:

In other examples, bands 106 and 110 may also participate in peer-to-hub communications with exemplary hub devices such as mobile communications device 118 and laptop 122. Bands 106 and 110 may communicate with mobile communications device 118 and laptop 122 using any number of wireless communication technologies (e.g., local wireless network, near field communication, Bluetooth®, Bluetooth® low energy, ANT, etc.). Using wireless communication technologies, mobile communications device 118 and laptop 122 may be used as a hub or gateway device to communicate data captured by bands 106 and 110 with other devices, in the same way as described above with respect to bands 104 and 108. Mobile communications device 118 and laptop 122 also may be used as a hub or gateway device to further share data captured by bands 106 and 110 with SNS, in the same way as described above with respect to bands 104 and 108.

Peer-to-peer communication may be exemplified by bands 106 and 110, exemplary peer devices, communicating directly. Band 106 may communicate directly with band 110, and vice versa, using known wireless communication technologies, as described above. Peer-to-peer communication may also be exemplified by communications between bands 104 and 108 and bands 106 and 110 through a hub device, such as mobile communications device 118 or laptop 122.

Alternatively, exemplary system 600 may be implemented with any combination of communication capable devices, such as any of the devices depicted in FIG. 1, communicating with each other using any communication platform, including any of the platforms described above. Persons of ordinary skill in the art will appreciate that the examples of peer-to-hub communication provided herein, and shown in FIG. 6, are only a small subset of the possible implementations of peer-to-hub communications involving the bands described herein.

Figure 7:
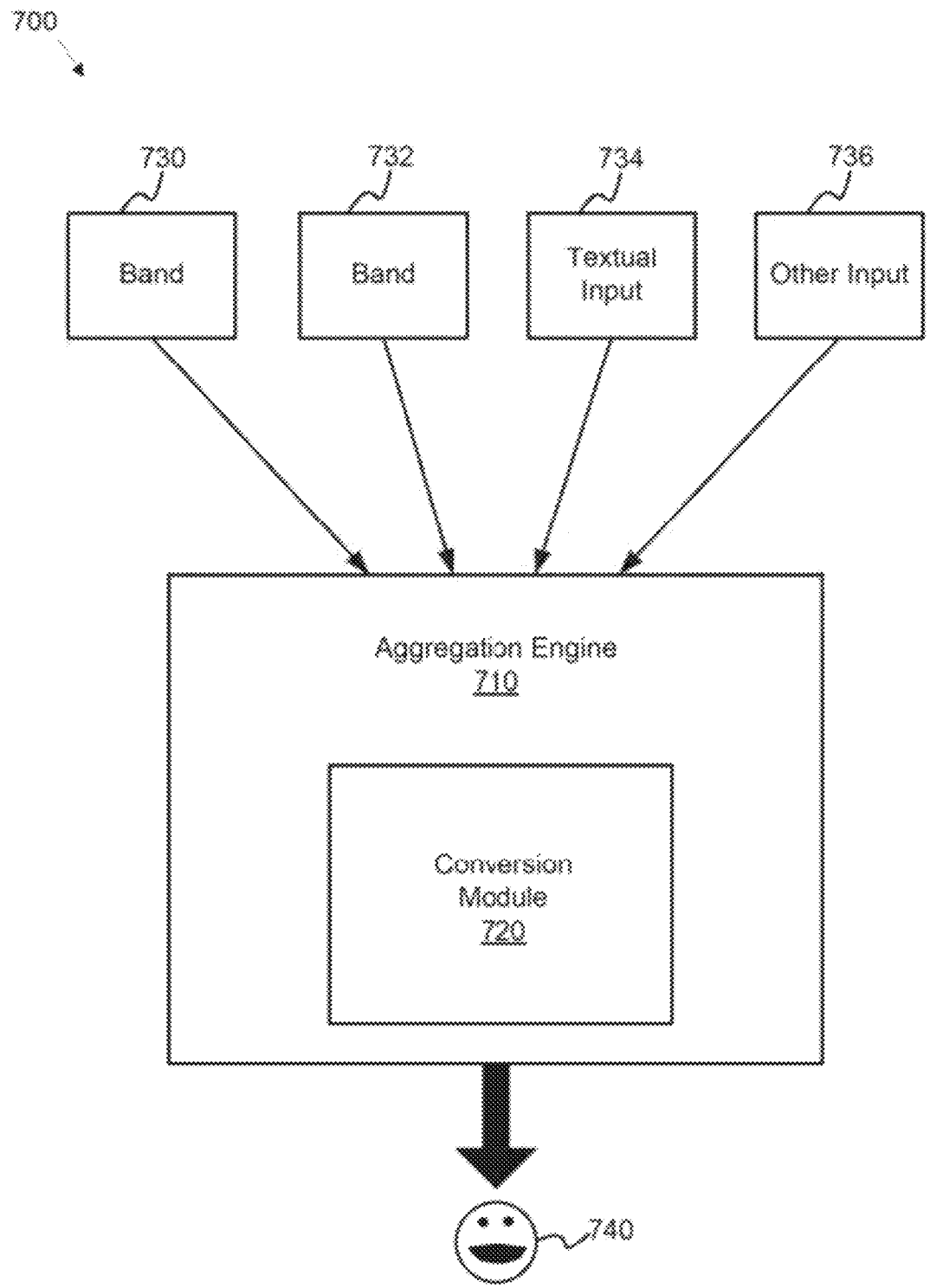
FIG. 7 illustrates an exemplary wellness tracking system for use with or within a distributed wellness application.

FIG. 7 illustrates an exemplary wellness tracking system for use with or within a distributed wellness application. System 700 comprises aggregation engine 710, conversion module 720, band 730, band 732, textual input 734, other input 736, and graphical representation 740. Bands 730 and 732 may be implemented as described above. In some examples, aggregation engine 710 may receive input from various sources. For example, aggregation engine 710 may receive sensory input from band 730, band 732, and/or other data-capable bands. This sensory input may include any of the above-described sensory data that may be gathered by data-capable bands. In other examples, aggregation engine 710 may receive other (e.g., manual) input from textual input 734 or other input 736. Textual input 734 and other input 736 may include information that a user types, uploads, or otherwise inputs into an application (e.g., a web application, an iPhone® application, etc.) implemented on any of the data and communications capable devices referenced herein (e.g., computer, laptop, computer, mobile communications device, mobile computing device, etc.). In some examples, aggregation engine 720 may be configured to process (e.g., interpret) the data and information received from band 730, band 732, textual input 734 and other input 736, to determine an aggregate value from which graphical representation 740 may be generated. In an example, system 700 may comprise a conversion module 720, which may be configured to perform calculations to convert the data received from band 730, band 732, textual input 734 and other input 736 into values (e.g., numeric values). Those values may then be aggregated by aggregation engine 710 to generate graphical representation 740. Conversion module 720 may be implemented as part of aggregation engine 710 (as shown), or it may be implemented separately (not shown). In some examples, aggregation engine 710 may be implemented with more or different modules. In other examples, aggregation engine 710 may be implemented with fewer or more input sources. In some examples, graphical representation 740 may be implemented differently, using different facial expressions, or any image or graphic according to any intuitive or predetermined set of graphics indicating various levels and/or aspects of wellness. As described in more detail below, graphical representation 740 may be a richer display comprising more than a single graphic or image (e.g., FIGS. 10 and 11).

In some examples, aggregation engine 710 may receive or gather inputs from one or more sources over a period of time, or over multiple periods of time, and organize those inputs into a database (not shown) or other type of organized form of information storage. In some examples, graphical representation 740 may be a simple representation of a facial expression, as shown. In other examples, graphical representation 740 may be implemented as a richer graphical display comprising inputs gathered over time (e.g., FIGS. 10 and 11 below).

Figure 8:
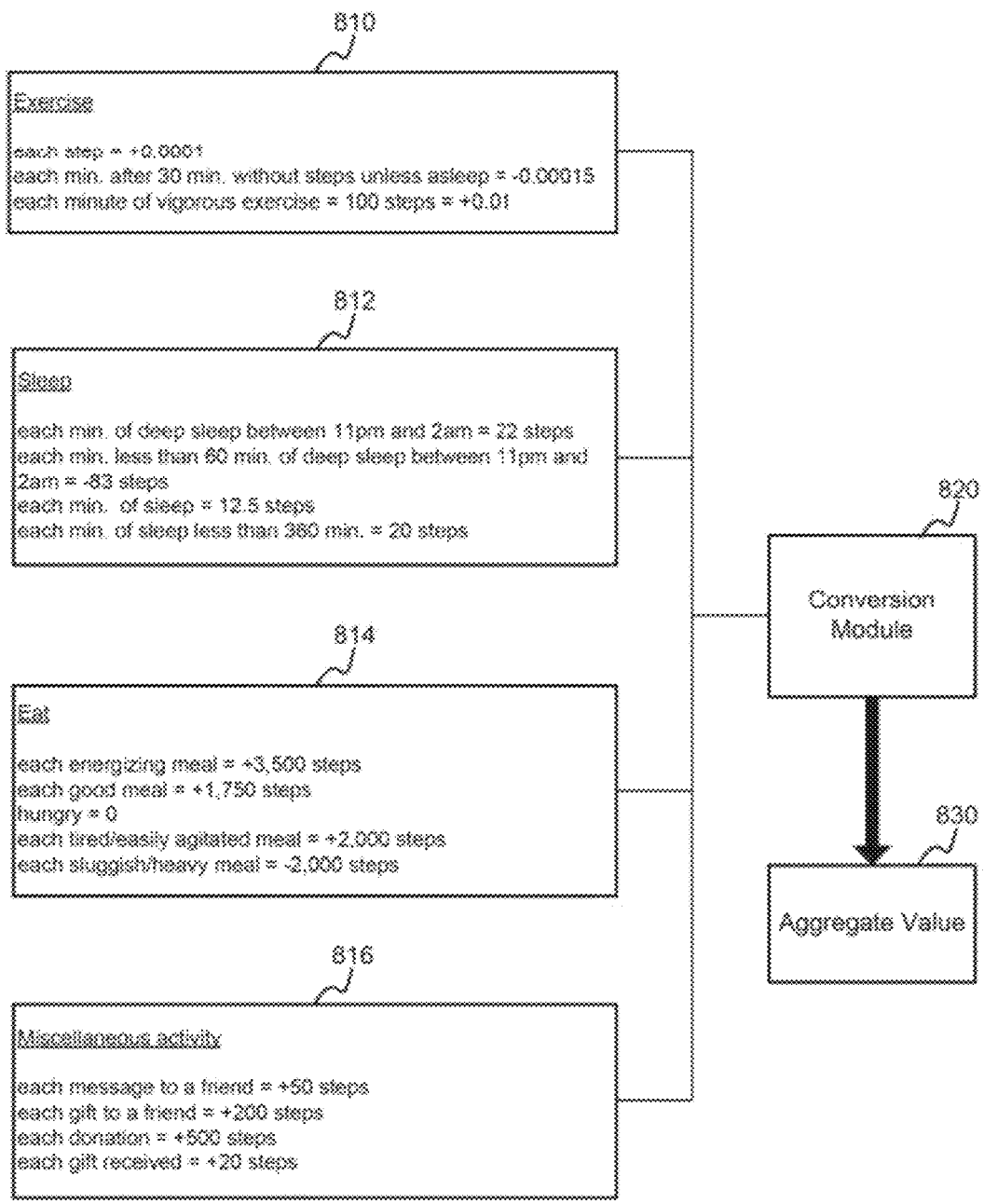
FIG. 8 illustrates representative calculations executed by an exemplary conversion module to determine an aggregate value for producing a graphical representation of a user's wellness.

FIG. 8 illustrates representative calculations executed by an exemplary conversion module to determine an aggregate value for producing a graphical representation of a user's wellness. In some examples, conversion module 820 may be configured to process data associated with exercise, data associated with sleep, data associated with eating or food intake, and data associated with other miscellaneous activity data (e.g., sending a message to a friend, gifting to a friend, donating, receiving gifts, etc.), and generate values from the data. For example, conversion module 820 may perform calculations using data associated with activities ("activity data") to generate values for types of exercise (e.g., walking, vigorous exercise, not enough exercise, etc.) (810), types of sleep (e.g., deep sleep, no sleep, not enough deep sleep, etc.) (812), types of meals (e.g., a sluggish/heavy meal, a good meal, an energizing meal, etc.) (814), or other miscellaneous activities (e.g., sending a message to a friend, gifting to a friend, donating, receiving gifts, etc.) (816). Note that while in this example types of sleep 812, types of meals 814, and miscellaneous activities 816 are expressed in numbers of steps, FIG. 8 is not intended to be limiting is one of numerous ways in which to express types of sleep 812, types of meals 814, and miscellaneous activities 816. For example, types of sleep 812, types of meals 814, and miscellaneous activities 816 can correspond to different point values of which one or more scores can be derived to determine aggregate value 830, which can be expressed in terms of points or a score. In some implementations, these values may include positive values for activities that are beneficial to a user's wellness and negative values for activities that are detrimental to a user's wellness, or for lack of activity (e.g., not enough sleep, too many minutes without exercise, etc.). In one example, the values may be calculated using a reference activity. For example, conversion module 820 may equate a step to the numerical value 0.0001, and then equate various other activities to a number of steps (810, 812, 814, 816). In some examples, these values may be weighted according to the quality of the activity. For example, each minute of deep sleep equals a higher number of steps than each minute of other sleep (812). As described in more detail below (FIGS. 10 and 11), these values may be modulated by time. For example, positive values for exercise may be modulated by negative values for extended time periods without exercise (810). In another example, positive values for sleep or deep sleep may be modulated by time without sleep or not enough time spent in deep sleep (812). In some examples, conversion module 820 is configured to aggregate these values to generate an aggregate value 830. In some examples, aggregate value 830 may be used by an aggregation engine (e.g., aggregation engine 710 described above) to generate a graphical representation of a user's wellness (e.g., graphical representation 740 described above, FIGS. 10 and 11 described below, or others).

Figure 9:
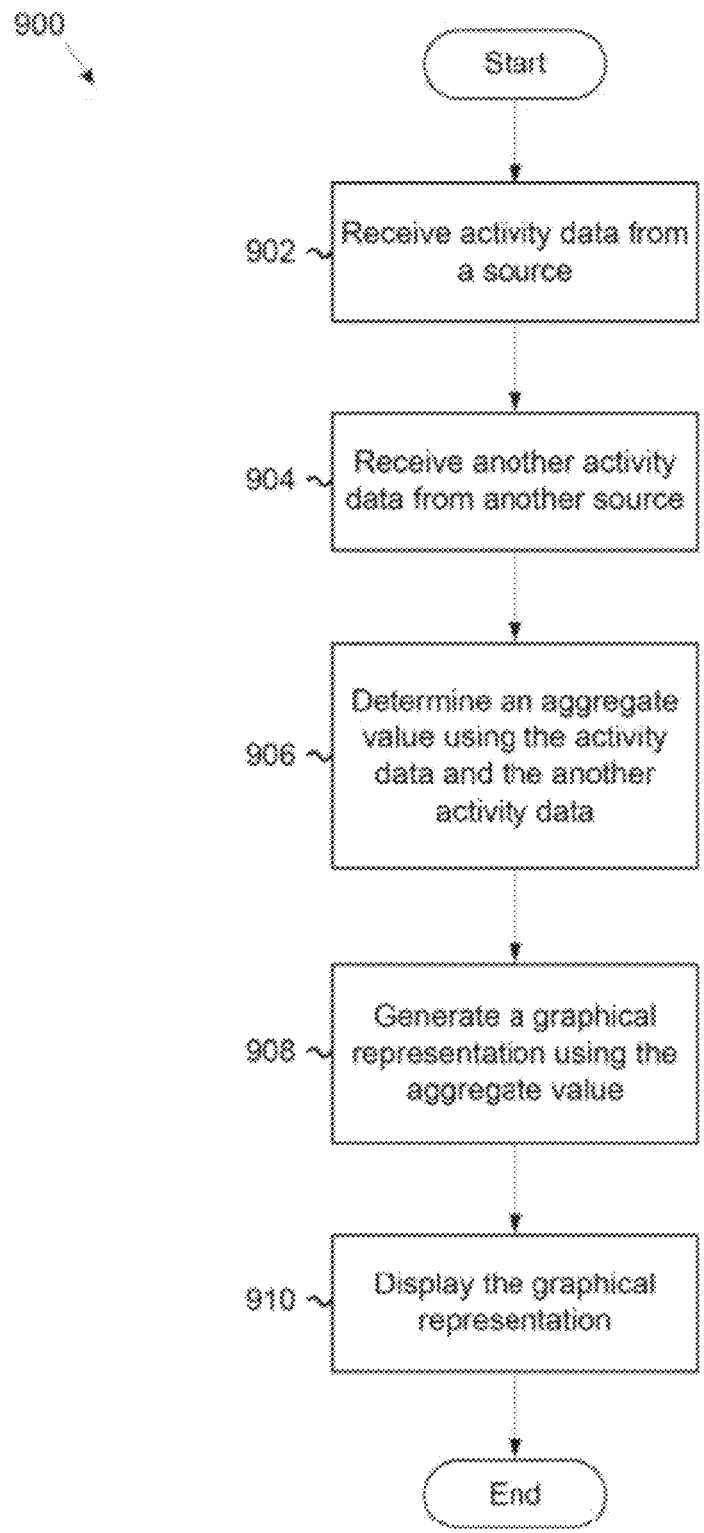
FIG. 9 illustrates an exemplary process for generating and displaying a graphical representation of a user's wellness based upon the user's activities.

FIG. 9 illustrates an exemplary process for generating and displaying a graphical representation of a user's wellness based upon the user's activities. Process 900 may be implemented as an exemplary process for creating and presenting a graphical representation of a user's wellness. In some examples, process 900 may begin with receiving activity data from a source (902). For example, the source may comprise one of the data-capable bands described herein (e.g., band 730, band 732, etc.). In another example, the source may comprise another type of data and communications capable device, such as those described above (e.g., computer, laptop, computer, mobile communications device, mobile computing device, etc.), which may enable a user to provide activity data via various inputs (e.g., textual input 734, other input 736, etc.). For example, activity data may be received from a data-capable band. In another example, activity data may be received from data manually input using an application user interface via a mobile communications device or a laptop. In other examples, activity data may be received from sources or combinations of sources. After receiving the activity data, another activity data is received from another source (904). The another source also may be any of the types of sources described above. Once received, the activity data from the source, and the another activity data from another source, is then used to determine (e.g., by conversion module 720 or 730, etc.) an aggregate value (906). Once determined, the aggregate value is used to generate a graphical representation of a user's present wellness (908) (e.g., graphical representation 740 described above, etc.). The aggregate value also may be combined with other information, of the same type or different, to generate a richer graphical representation (e.g., FIGS. 10 and 11 described below, etc.).

In other examples, activity data may be received from multiple sources. These multiple sources may comprise a combination of sources (e.g., a band and a mobile communications device, two bands and a laptop, etc.) (not shown). Such activity data may be accumulated continuously, periodically, or otherwise, over a time period. As activity data is accumulated, the aggregate value may be updated and/or accumulated, and in turn, the graphical representation may be updated. In some examples, as activity data is accumulated and the aggregate value updated and/or accumulated, additional graphical representations may be generated based on the updated or accumulated aggregate value(s). In other examples, the above-described process may be varied in the implementation, order, function, or structure of each or all steps and is not limited to those provided.

Figure 10:
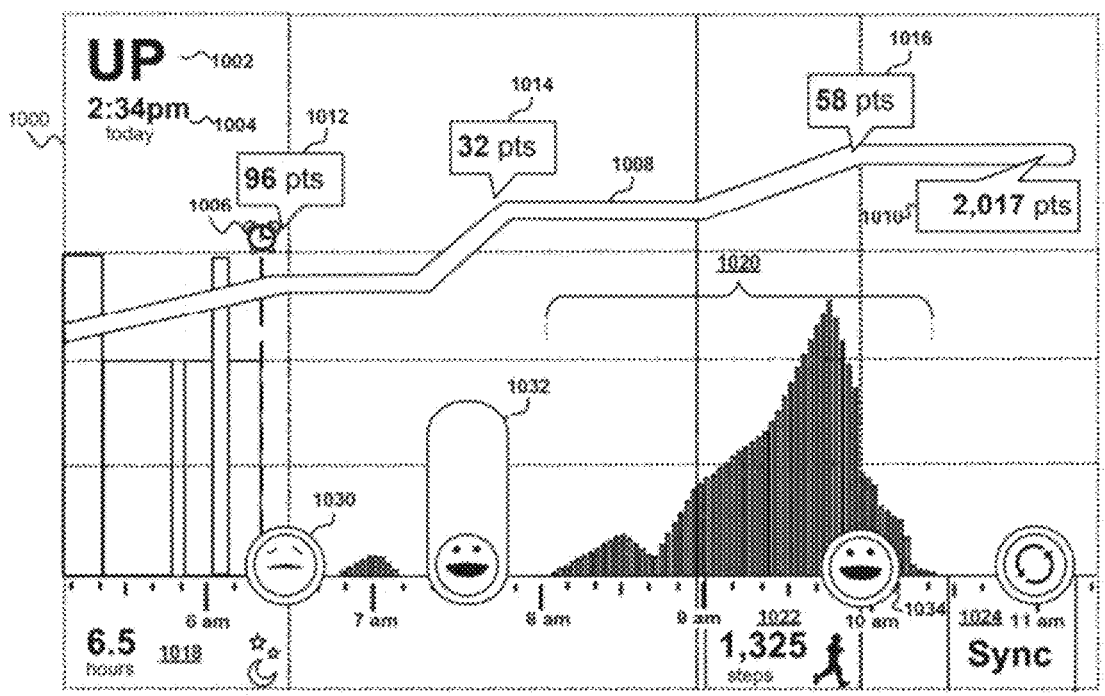
FIG. 10 illustrates an exemplary graphical representation of a user's wellness over a time period.

FIG. 10 illustrates an exemplary graphical representation of a user's wellness over a time period. Here, exemplary graphical representation 1000 shows a user's wellness progress over the course of a partial day. Exemplary graphical representation 1000 may comprise a rich graph displaying multiple vectors of data associated with a user's wellness over time, including a status 1002, a time 1004, alarm graphic 1006, points progress line 1008, points gained for completion of activities 1012-1016, total points accumulated 1010, graphical representations 1030-1034 of a user's wellness at specific times over the time period, activity summary data and analysis over time (1018-1022), and an indication of syncing activity 1024. Here, status 1002 may comprise a brief (e.g., single word) general summary of a user's wellness. In some examples, time 1004 may indicate the current time, or in other examples, it may indicate the time that graphical representation 1000 was generated or last updated. In some other examples, time 1004 may be implemented using different time zones. In still other examples, time 1004 may be implemented differently. In some examples, alarm graphic 1006 may indicate the time that the user's alarm rang, or in other examples, it may indicate the time when a band sensed the user awoke, whether or not an alarm rang. In other examples, alarm graphic 1006 may indicate the time when a user's band began a sequence of notifications to wake up the user (e.g., using notification facility 208, as described above), and in still other examples, alarm graphic 1006 may represent something different. As shown here, graphical representation 1000 may include other graphical representations of the user's wellness at specific times of the day (1030, 1032, 1034), for example, indicating a low level of wellness or low energy level soon after waking up (1030) and a more alert or higher energy or wellness level after some activity (1032, 1034). Graphical representation 1000 may also include displays of various analyses of activity over time. For example, graphical representation may include graphical representations of the user's sleep (1018), including how many total hours slept and the quality of sleep (e.g., bars may represent depth of sleep during periods of time). In another example, graphical representation may include graphical representations of various aspects of a user's exercise level for a particular workout, including the magnitude of the activity level (1020), duration (1020), the number of steps taken (1022), the user's heart rate during the workout (not shown), and still other useful information (e.g., altitude climbed, laps of a pool, number of pitches, etc.). Graphical representation 1000 may further comprise an indication of syncing activity (1024) showing that graphical representation 1000 is being updated to include additional information from a device (e.g., a data-capable band) or application. Graphical representation 1000 may also include indications of a user's total accumulated points 1010, as well as points awarded at certain times for certain activities (1012, 1014, 1016). For example, shown here graphical representation 1000 displays the user has accumulated 2,017 points in total (e.g., over a lifetime, over a set period of time, etc.) (1010).

In some examples, points awarded may be time-dependent or may expire after a period of time. For example, points awarded for eating a good meal may be valid only for a certain period of time. This period of time may be a predetermined period of time, or it may be dynamically determined. In an example where the period of time is dynamically determined, the points may be valid only until the user next feels hunger. In another example where the period of time is dynamically determined, the points may be valid depending on the glycemic load of the meal (e.g., a meal with low glycemic load may have positive effects that meal carry over to subsequent meals, whereas a meal with a higher glycemic load may have a positive effect only until the next meal). In some examples, a user's total accumulated points 1010 may reflect that certain points have expired and are no longer valid.

In some examples, these points may be used for obtaining various types of rewards, or as virtual or actual currency, for example, in an online wellness marketplace, as described herein (e.g., a fitness marketplace). For example, points may be redeemed for virtual prizes (e.g., for games, challenges, etc.), or physical goods (e.g., products associated with a user's goals or activities, higher level bands, which may be distinguished by different colors, looks and/or features, etc.). In some examples, the points may automatically be tracked by a provider of data-capable bands, such that a prize (e.g., higher level band) is automatically sent to the user upon reaching a given points threshold without any affirmative action by the user. In other examples, a user may redeem a prize (e.g., higher level band) from a store. In still other examples, a user may receive deals. These deals or virtual prizes may be received digitally via a data-capable band, a mobile communications device, or otherwise.

Figure 11:
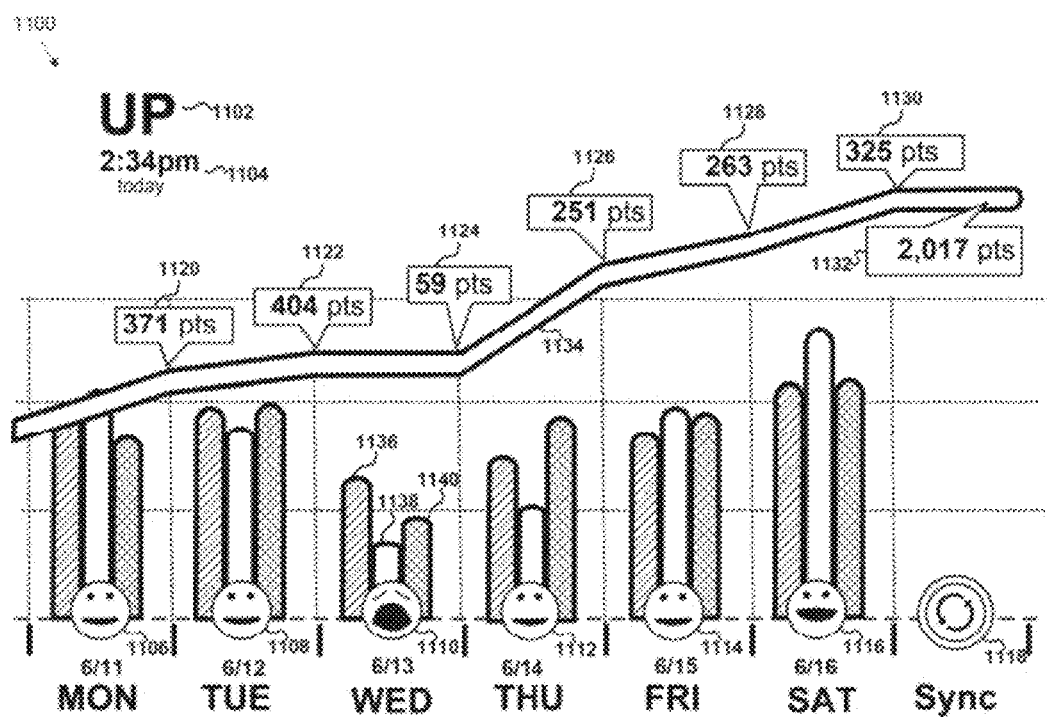
FIG. 11 illustrates another exemplary graphical representation of a user's wellness over a time period.
Figure 12A:
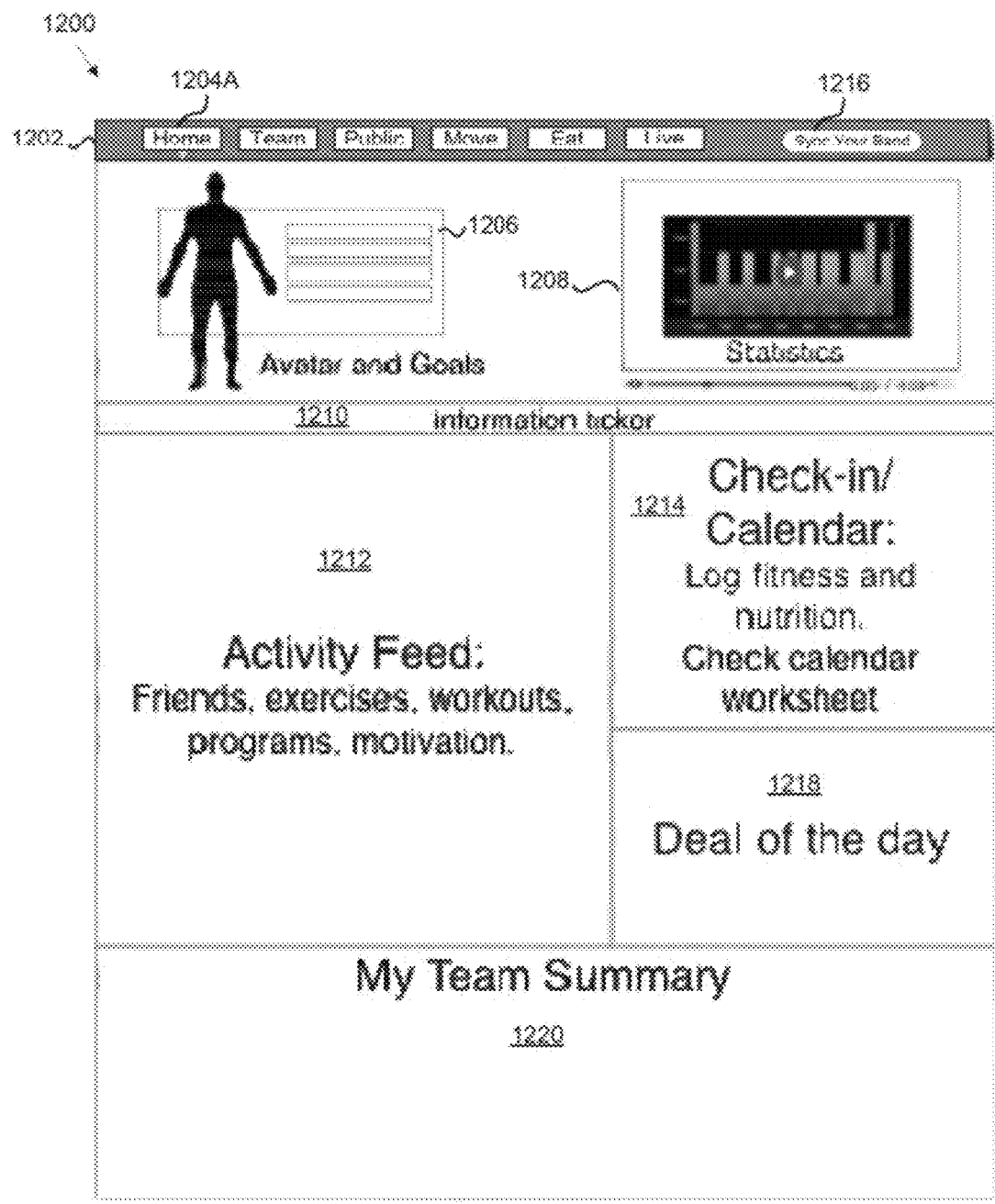
FIGS. 12A-12F illustrate exemplary wireframes of exemplary webpages associated with a wellness marketplace portal.
Figure 12B:
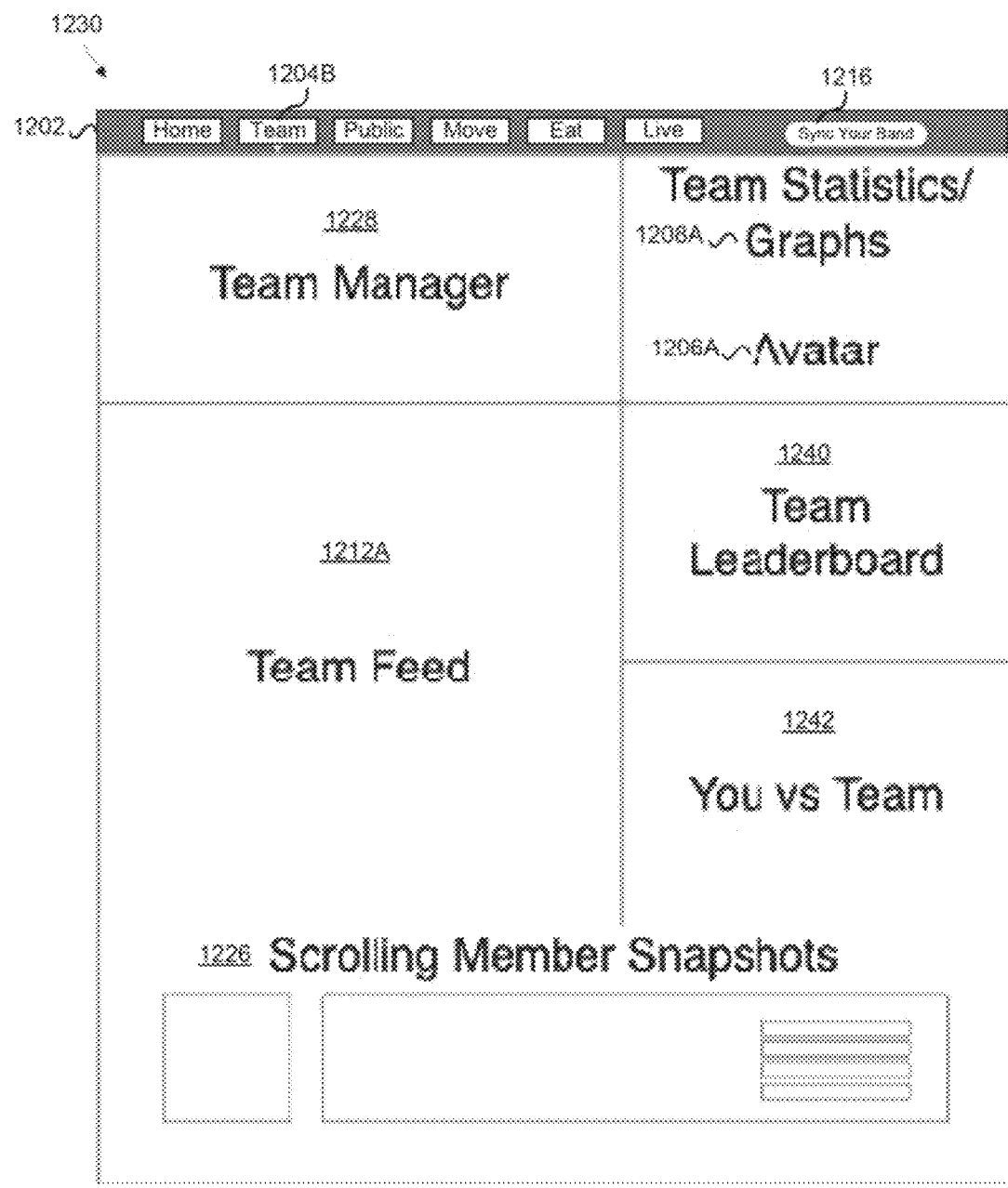
Figure 12C:
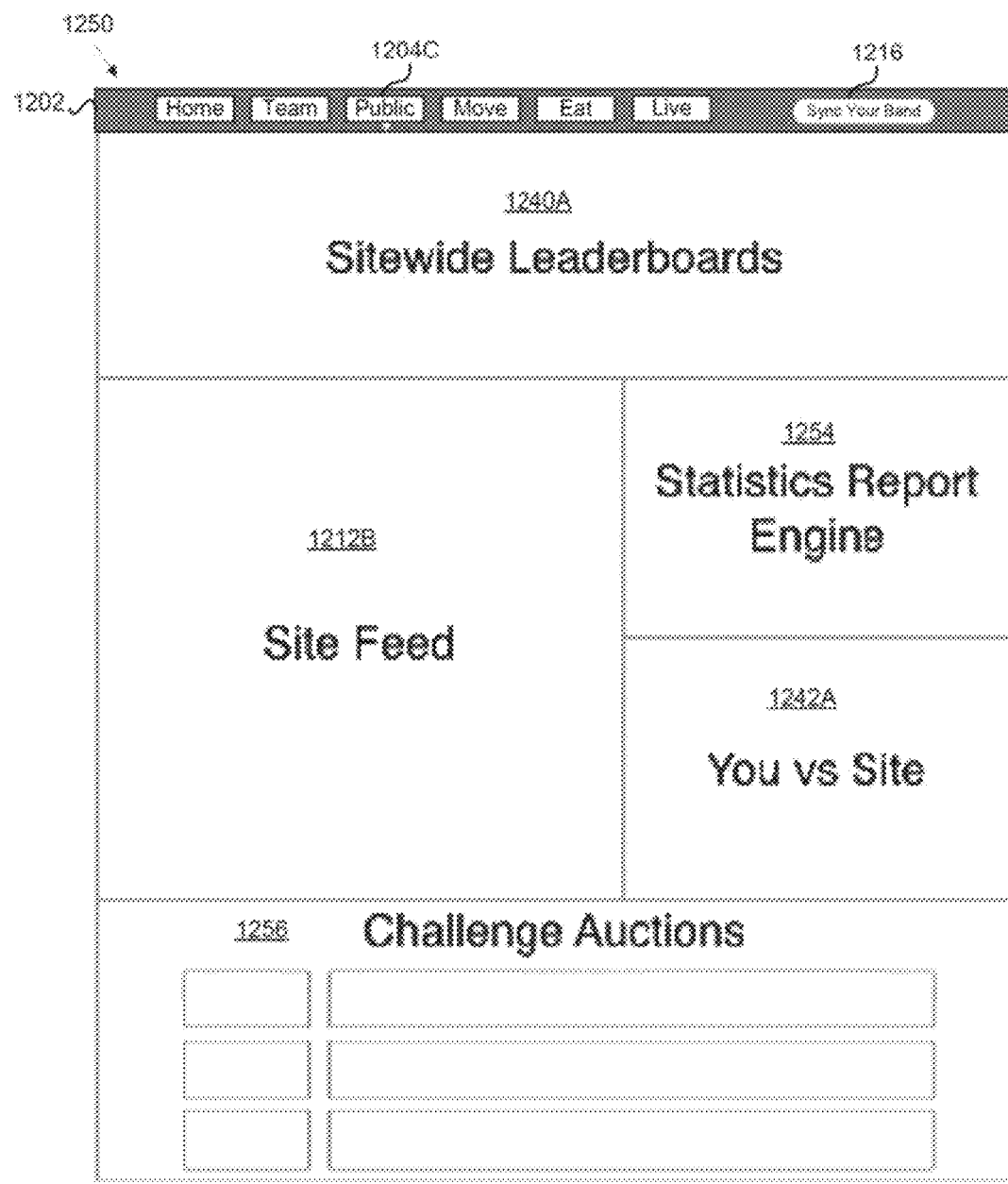
Figure 12D:
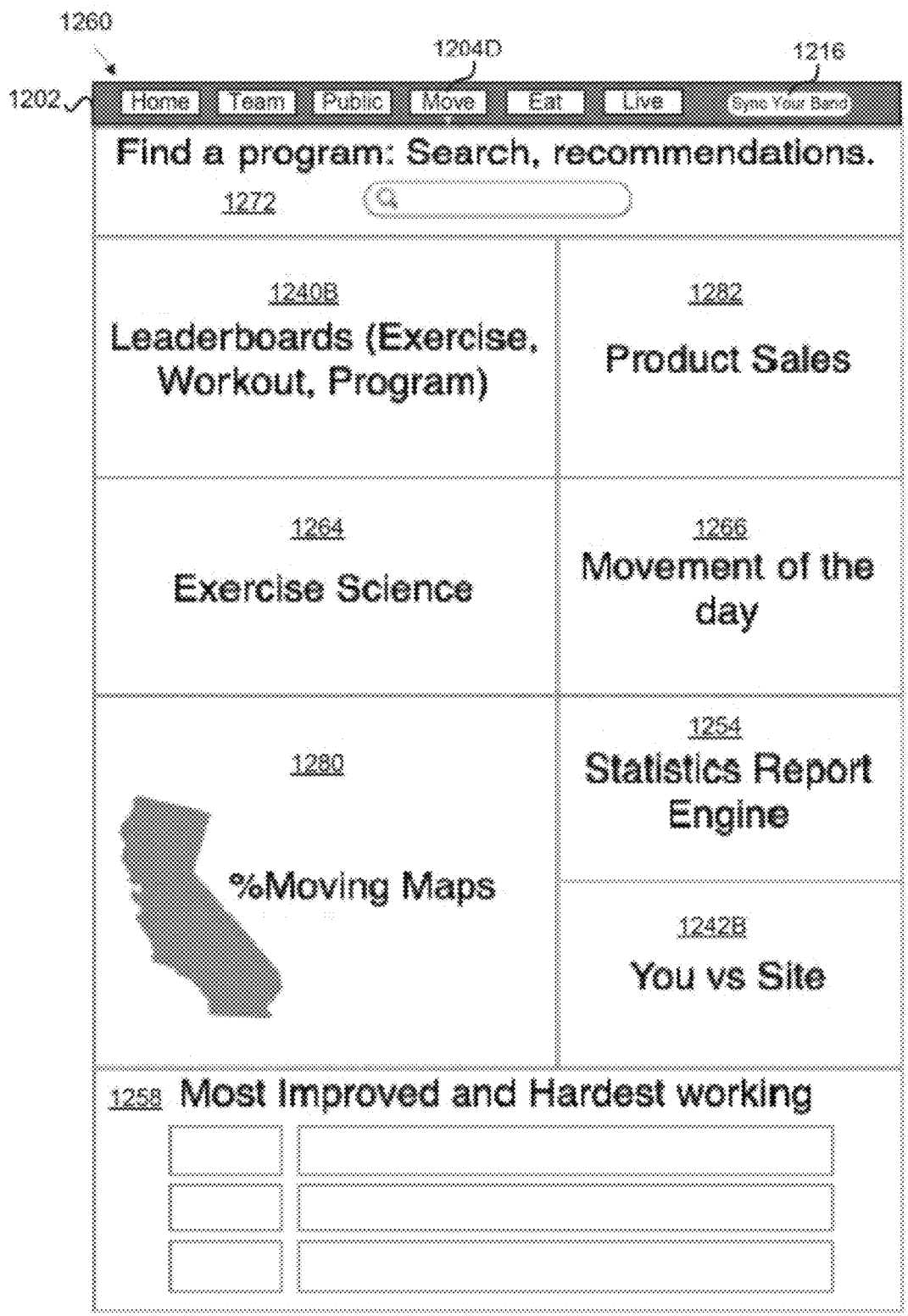
Figure 12E:
Figure 12F:

FIG. 11 illustrates another exemplary graphical representation of a user's wellness over a time period. Here, exemplary graphical representation 1100 shows a summary of a user's wellness progress over the course of a week. Exemplary graphical representation 1100 may comprise a rich graph displaying multiple vectors of data associated with a user's wellness over time, including a status 1102, a time 1104, summary graphical representations 1106-1116 of a user's wellness on each days, points earned each day 1120-1130, total points accumulated 1132, points progress line 1134, an indication of syncing activity 1118, and bars 1136-1140. Here, as with status 1002 in FIG. 10, status 1102 may comprise a brief (e.g., single word) general summary of a user's wellness. In some examples, time 1104 may indicate the current time, or in other examples, it may indicate the time that graphical representation 1100 was generated or last updated. In some other examples, time 1104 may be implemented using different time zones. In still other examples, time 1104 may be implemented differently. As shown here, graphical representation 1100 may include summary graphical representations 1106-1116 of the user's wellness on each day, for example, indicating a distress or tiredness on Wednesday (1110) or a positive spike in wellness on Friday (1116). In some examples, summary graphical representations 1106-1116 may indicate a summary wellness for that particular day. In other examples, summary graphical representations 1106-1116 may indicate a cumulative wellness, e.g., at the end of each day. Graphical representation 1100 may further comprise an indication of syncing activity 1118 showing that graphical representation 1100 is being updated to include additional information from a device (e.g., a data-capable band) or application. Graphical representation 1100 may also include indications of a user's total accumulated points 1132, as well as points earned each day 1120-1130. For example, shown here graphical representation 1100 displays the user has accumulated 2,017 points thus far, which includes 325 points earned on Saturday (1130), 263 points earned on Friday (1128), 251 points earned on Thursday (1126), and so on. As described above, these points may be used for obtaining various types of rewards, or as virtual or actual currency, for example, in an online wellness marketplace (e.g., a fitness marketplace as described above). In some examples, graphical representation 1100 also may comprise bars 1136-1140. Each bar may represent an aspect of a user's wellness (e.g., food, exercise, sleep, etc.). In some examples, the bar may display the user's daily progress toward a personal goal for each aspect (e.g., to sleep eight hours, complete sixty minutes of vigorous exercise, etc.). In other examples, the bar may display the user's daily progress toward a standardized goal (e.g., a health and fitness expert's published guidelines, a government agency's published guidelines, etc.), or other types of goals.

FIGS. 12A-12F illustrate exemplary wireframes of exemplary webpages associated with a wellness marketplace. Here, wireframe 1200 comprises navigation 1202, selected page 1204A, sync widget 1216, avatar and goals element 1206, statistics element 1208, information ticker 1210, social feed 1212, check-in/calendar element 1214, deal element 1218, and team summary element 1220. As described above, a wellness marketplace may be implemented as a portal, website or application where users, may find, purchase, or download applications, products, information, etc., for various uses, as well as share information with other users (e.g., users with like interests). Here, navigation 1202 comprises buttons and widgets for navigating through various pages of the wellness marketplace, including the selected page 1204A-1204F (e.g., the Home page, Team page, Public page, Move page, Eat page, Live page, etc.) and sync widget 1216. In some examples, sync widget 1216 may be implemented to sync a data-capable band to the user's account on the wellness marketplace. In some examples, the Home page may include avatar and goals element 1206, which may be configured to display a user's avatar and goals. Avatar and goals element 1206 also may enable a user to create an avatar, either by selecting from predetermined avatars, by uploading a user's own picture or graphic, or other known methods for creating an avatar. Avatar and goals element 1206 also may enable a user to set goals associated with the user's health, eating/drinking habits, exercise, sleep, socializing, or other aspects of the user's wellness. The Home page may further include statistics element 1208, which may be implemented to display statistics associated with the user's wellness (e.g., the graphical representations described above). As shown here, in some examples, statistics element 1208 may be implemented as a dynamic graphical, and even navigable, element (e.g., a video or interactive graphic), wherein a user may view the user's wellness progress over time. In other examples, the statistics element 1208 may be implemented as described above (e.g., FIGS. 10 and 11). The Home page may further include information ticker 1210, which may stream information associated with a user's activities, or other information relevant to the wellness marketplace. The Home page may further include social feed 1212, which may be implemented as a scrolling list of messages or information (e.g., encouragement, news, feedback, recommendations, comments, etc.) from friends, advisors, coaches, or other users. The messages or information may include auto-generated encouragement, comments, news, recommendations, feedback, achievements, opinions, actions taken by teammates, or other information, by a wellness application in response to data associated with the user's wellness and activities (e.g., gathered by a data-capable band). In some examples, social feed 1212 may be searchable. In some examples, social feed 1212 may enable a user to filter or select the types of messages or information that shows up in the feed (e.g., from the public, only from the team, only from the user, etc.). Social feed 1212 also may be configured to enable a user to select an action associated with each feed message (e.g., cheer, follow, gift, etc.). In some examples, check-in/calendar element 1214 may be configured to allow a user to log their fitness and nutrition. In some examples, check-in/calendar element 1214 also may be configured to enable a user to maintain a calendar. Deal element 1218 may provide a daily deal to the user. The daily deal may be featured for the marketplace, it may be associated with the user's activities, or it may be generated using a variety of known advertising models. Team summary element 1220 may provide summary information about the user's team. As used herein, the term "team" may refer to any group of users that elect to use the wellness marketplace together. In some examples, a user may be part of more than one team. In other examples, a group of users may form different teams for different activities, or they may form a single team that participates in, tracks, and shares information regarding, more than one activity. A Home page may be implemented differently than described here.

Wireframe 1230 comprises an exemplary Team page, which may include a navigation 1202, selected page 1204B, sync widget 1216, team manager element 1228, leaderboard element 1240, comparison element 1242, avatar and goals element 1206A, statistics element 1208A, social feed 1212A, and scrolling member snapshots element 1226. Avatar and goals element 1206A and statistics element 1208A may be implemented as described above with regard to like-numbered or corresponding elements. Navigation 1202, selected page 1204B and sync widget 1216 also may be implemented as described above with regard to like-numbered or corresponding elements. In some examples, team manager element 1228 may be implemented as an area for displaying information, or providing widgets, associated with team management. Access to team manager element 1228 may be restricted, in some examples, or access may be provided to the entire team. Leaderboard element 1240 may be implemented to display leaders in various aspects of an activity in which the team is participating (e.g., various sports, social functions (e.g., clubs), drinking abstinence, etc.). In some examples, leaderboard element 1240 may be implemented to display leaders among various groupings (e.g., site-wide, team only, other users determined to be "like" the user according to certain criteria (e.g., similar activities), etc.). In other examples, leaderboard element 1240 may be organized or filtered by various parameters (e.g., date, demographics, geography, activity level, etc.). Comparison element 1242 may be implemented, in some examples, to provide comparisons regarding a user's performance with respect to an activity, or various aspects of an activity, with the performance of the user's teammates or with the team as a whole (e.g., team average, team median, team favorites, etc.). Scrolling member snapshots element 1226 may be configured to provide brief summary information regarding each of the members of the team in a scrolling fashion. A Team page may be implemented differently than described here.

Wireframe 1250 comprises an exemplary Public page, which may include navigation 1202, selected page 1204C, sync widget 1216, leaderboard element 1240A, social feed 1212B, statistics report engine 1254, comparison element 1242A, and challenge element 1256. Navigation 1202, selected page 1204C and sync widget 1216 may be implemented as described above with regard to like-numbered or corresponding elements. Leaderboard element 1240A also may be implemented as described above with regard to leaderboard element 1240, and in some examples, may display leaders amongst all of the users of the wellness marketplace. Social feed 1212B also may be implemented as described above with regard social feed 1212 and social feed 1212A. Comparison element 1242A may be implemented as described above with regard to comparison element 1242, and in some examples, may display comparisons of a user's performance of an activity against the performance of all of the other users of the wellness marketplace. Statistics report engine 1254 may generate and display statistical reports associated with various activities being monitored by, and discussed in, the wellness marketplace. In some examples, challenge element 1256 may enable a user to participate in marketplace-wide challenges with other users. In other examples, challenge element 1256 may display the status of, or other information associated with, ongoing challenges among users. A Public page may be implemented differently than described here.

Wireframe 1260 comprises an exemplary Move page, which may include navigation 1202, selected page 1204D, sync widget 1216, leaderboard element 1240B, statistics report engine 1254, comparison element 1242B, search and recommendations element 1272, product sales element 1282, exercise science element 1264, daily movement element 1266, maps element 1280 and titles element 1258. Navigation 1202, selected page 1204D, sync widget 1216, leaderboard element 1240B, statistics report engine 1254, and comparison element 1242B may be implemented as described above with regard to like-numbered or corresponding elements. The Move page may be implemented to include a search and recommendations element 1272, which may be implemented to enable searching of the wellness marketplace. In some examples, in addition to results of the search, recommendations associated with the user's search may be provided to the user. In other examples, recommendations may be provided to the user based on any other data associated with the user's activities, as received by, gathered by, or otherwise input into, the wellness marketplace. Product sales element 1282 may be implemented to display products for sale and provide widgets to enable purchases of products by users. The products may be associated with the user's activities or activity level. Daily movement element 1266 may be implemented to suggest an exercise each day. Maps element 1280 may be implemented to display information associated with the activity of users of the wellness marketplace on a map. In some examples, maps element 1280 may display a percentage of users that are physically active in a geographical region. In other examples, maps element 1280 may display a percentage of users that have eaten well over a particular time period (e.g., currently, today, this week, etc.). In still other examples, maps element 1280 may be implemented differently. In some examples, titles element 1258 may display a list of users and the titles they have earned based on their activities and activity levels (e.g., a most improved user, a hardest working user, etc.). A Move page may be implemented differently than described here.

Wireframe 1270 comprises an exemplary Eat page, which may include navigation 1202, selected page 1204E, sync widget 1216, leaderboard elements 1240C and 1240D, statistics report engine 1254, comparison element 1242C, search and recommendations element 1272, product sales element 1282, maps element 1280A, nutrition science element 1276, and daily food/supplement element 1278. Navigation 1202, selected page 1204E, sync widget 1216, leaderboard elements 1240C and 1240D, statistics report engine 1254, comparison element 1242C, search and recommendations element 1272, product sales element 1282, and maps element 1280A may be implemented as described above with regard to like-numbered or corresponding elements. The Eat page may be implemented to include a nutrition science element 1276, which may display, or provide widgets for accessing, information associated with nutrition science. The Eat page also may be implemented with a daily food/supplement element 1278, which may be implemented to suggest an food and/or supplement each day. An Eat page may be implemented differently than described here.

Wireframe 1280 comprises an exemplary Live page, which may include navigation 1202, selected page 1204F, sync widget 1216, leaderboard element 1240E, search and recommendations element 1272, product sales element 1282, maps element 1280B, social feed 1212C, health research element 1286, and product research element 1290. Navigation 1202, selected page 1204F, sync widget 1216, leaderboard element 1240E, search and recommendations element 1272, product sales element 1282, maps element 1280B and social feed 1212C may be implemented as described above with regard to like-numbered or corresponding elements. In some examples, the Live page may include health research element 1286 configured to display, or to enable a user to research, information regarding health topics. In some examples, the Live page may include product research element 1290 configured to display, or to enable a user to research, information regarding products. In some examples, the products may be associated with a user's particular activities or activity level. In other examples, the products may be associated with any of the activities monitored by, or discussed on, the wellness marketplace. A Live page may be implemented differently than described here.

Figure 13:
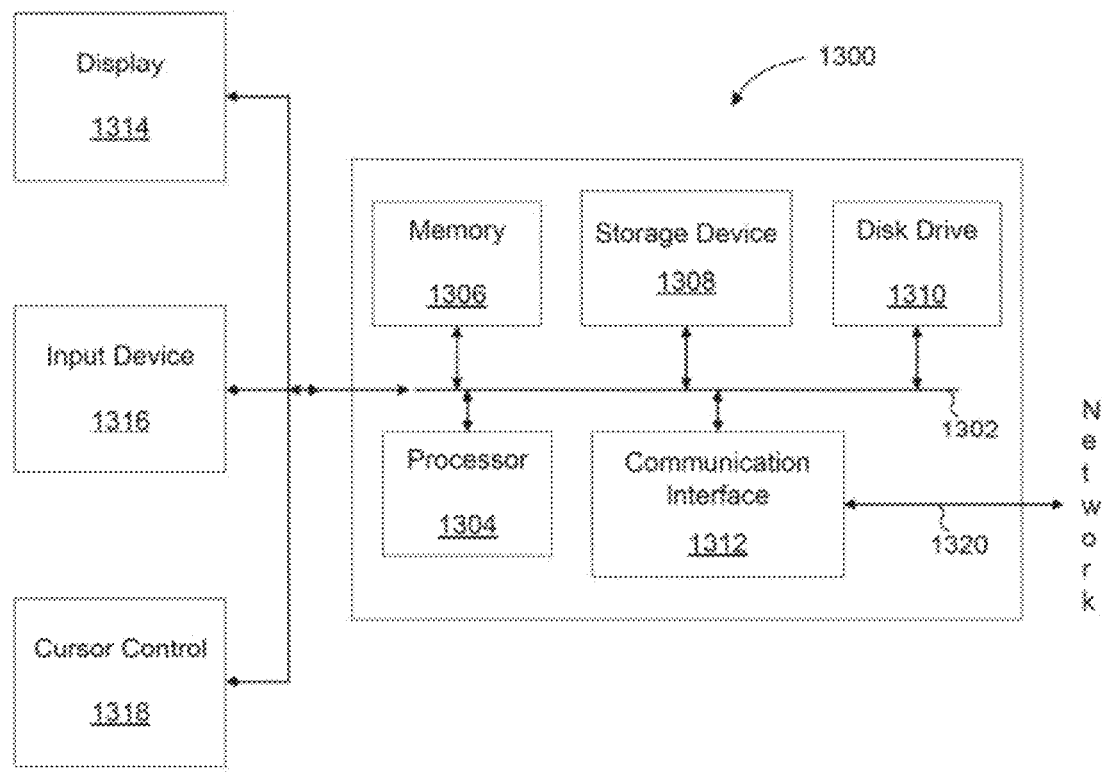
FIG. 13 illustrates an exemplary computer system suitable for implementation of a wellness application and use with a data-capable band.

FIG. 13 illustrates an exemplary computer system suitable for implementation of a wellness application and use with a data-capable band. In some examples, computer system 1300 may be used to implement computer programs, applications, methods, processes, or other software to perform the above-described techniques. Computer system 1300 includes a bus 1302 or other communication mechanism for communicating information, which interconnects subsystems and devices, such as processor 1304, system memory 1306 (e.g., RAM), storage device 1308 (e.g., ROM), disk drive 1310 (e.g., magnetic or optical), communication interface 1312 (e.g., modem or Ethernet card), display 1314 (e.g., CRT or LCD), input device 1316 (e.g., keyboard), and cursor control 1318 (e.g., mouse or trackball).

According to some examples, computer system 1300 performs specific operations by processor 1304 executing one or more sequences of one or more instructions stored in system memory 1306. Such instructions may be read into system memory 1306 from another computer readable medium, such as static storage device 1308 or disk drive 1310. In some examples, hard-wired circuitry may be used in place of or in combination with software instructions for implementation.

The term "computer readable medium" refers to any tangible medium that participates in providing instructions to processor 1304 for execution. Such a medium may take many forms, including but not limited to, non-volatile media and volatile media. Non-volatile media includes, for example, optical or magnetic disks, such as disk drive 1310. Volatile media includes dynamic memory, such as system memory 1306.

Common forms of computer readable media includes, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, or any other medium from which a computer can read.

Instructions may further be transmitted or received using a transmission medium. The term "transmission medium" may include any tangible or intangible medium that is capable of storing, encoding or carrying instructions for execution by the machine, and includes digital or analog communications signals or other intangible medium to facilitate communication of such instructions. Transmission media includes coaxial cables, copper wire, and fiber optics, including wires that comprise bus 1302 for transmitting a computer data signal.

In some examples, execution of the sequences of instructions may be performed by a single computer system 1300. According to some examples, two or more computer systems 1300 coupled by communication link 1320 (e.g., LAN, PSTN, or wireless network) may perform the sequence of instructions in coordination with one another. Computer system 1300 may transmit and receive messages, data, and instructions, including program, i.e., application code, through communication link 1320 and communication interface 1312. Received program code may be executed by processor 1304 as it is received, and/or stored in disk drive 1310, or other non-volatile storage for later execution.

Figure 14:
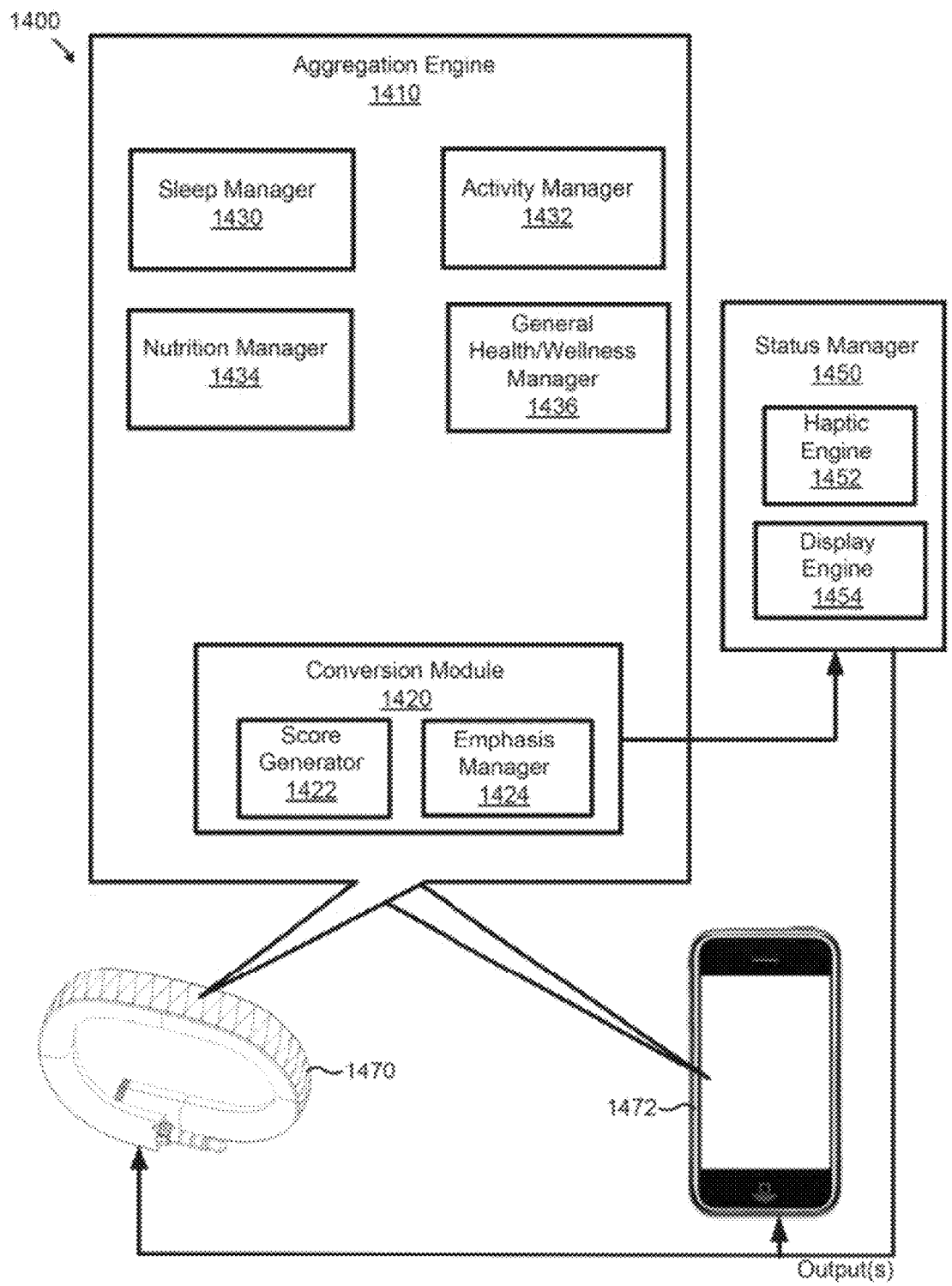
FIG. 14 depicts an example of an aggregation engine, according to some examples.

FIG. 14 depicts an example of an aggregation engine, according to some examples. Diagram 1400 depicts an aggregation engine 1410 including one or more of the following: a sleep manager 1430, an activity manager 1432, a nutrition manager 1434, a general health/wellness manager 1436, and a conversion module 1420. As described herein, aggregation engine 1410 is configured to process data, such as data representing parameters based on sensor measurements or the like, as well as derived parameters that can be derived (e.g., mathematically) based on data generated by one or more sensors. Aggregation engine 1410 also can be configured to determine an aggregate value (or score) from which a graphical representation or any other representation can be generated. Conversion module 1420 is configured to convert data or scores representing parameters into values or scores indicating relative states of sleep, activity, nutrition, or general fitness or health (e.g., based on combined states of sleep, activity, nutrition). Further, values or scores generated by conversion module 1420 can be based on team achievements (e.g., one or more other users' sensor data or parameters).

Sleep manager 1430 is configured to receive data representing parameters relating to sleep activities of a user, and configured to maintain data representing one or more sleep profiles. Parameters describe characteristics, factors or attributes of, for example, sleep, and can be formed from sensor data or derived based on computations. Examples of parameters include a sleep start time (e.g., in terms of Coordinated Universal. Time, "UTC," or Greenwich Mean Time), a sleep end time, and a duration of sleep, which is derived from determining the difference between the sleep end and start times. Sleep manager 1430 cooperates with conversion module 1420 to form a target sleep score to which a user strives to attain. As such, sleep manager 1430 is configured to track a user's progress and to motivate the user to modify sleep patterns to attain an optimal sleep profile. Sleep manager 1430, therefore, is configured to coach a user to improve the user's health and wellness by improving the user's sleep activity. According to various one or more examples, sleep-related parameters can be acquired or derived by any of the sensors or sensor functions described in, for example, FIGS. 3 to 5E. For example, other parameters (e.g., location-related parameters describing a home/bedroom location or social-related parameters describing proximity with family members) can be used to determine whether a user is engaged in a sleep-related activity and a quality or condition thereof.

Activity manager 1432 is configured to receive data representing parameters relating to one or more motion or movement-related activities of a user and to maintain data representing one or more activity profiles. Activity-related parameters describe characteristics, factors or attributes of motion or movements in which a user is engaged, and can be established from sensor data or derived based on computations. Examples of parameters include motion actions, such as a step, stride, swim stroke, rowing stroke, bike pedal stroke, and the like, depending on the activity in which a user is participating. As used herein, a motion action is a unit of motion (e.g., a substantially repetitive motion) indicative of either a single activity or a subset of activities and can be detected, for example, with one or more accelerometers and/or logic configured to determine an activity composed of specific motion actions. Activity manager 1432 cooperates with conversion module 1420 to form a target activity score to which a user strives to attain. As such, activity manager 1432 is configured to track a user's progress and to motivate the user to modify anaerobic and/or aerobic activities to attain or match the activities defined by an optimal activity profile. Activity manager 1432, therefore, is configured to coach a user to improve the user's health and wellness by improving the user's physical activity, including primary activities of exercise and incidental activities (e.g., walking and climbing stairs in the home, work, etc.). According to various one or more examples, activity-related parameters can be acquired or derived by any of the sensors or sensor functions described in, for example, FIGS. 3 to 5E. For example, other parameters (e.g., location-related parameters describing a gym location or social-related parameters describing proximity to other persons working out) can be used to determine whether a user is engaged in a movement-related activity, as well as the aspects thereof.

Nutrition manager 1434 is configured to receive data representing parameters relating to one or more activities relating to nutrition intake of a user and to maintain data representing one or more nutrition profiles. Nutrition-related parameters describe characteristics, factors or attributes of consumable materials (e.g., food and drink), including nutrients, such as vitamins, minerals, etc. that a user consumes. Nutrition-related parameters also include calories. The nutrition-related parameters can be formed from sensor data or derived based on computations. In some cases, a user provides or initiates data retrieval representing the nutrition of food and drink consumed. Nutrition-related parameters also can be derived, such as calories burned or expended. Examples of parameters include an amount (e.g., expressed in international units, "IU") of a nutrient, such as a vitamin, fiber, mineral, fat (various types), or a macro-nutrient, such as water, carbohydrate, and the like. Nutrition manager 1434 cooperates with conversion module 1420 to form a target nutrition score to which a user strives to attain. As such, nutrition manager 1434 is configured to track a user's progress and to motivate the user to modify dietary-related activities and consumption to attain an optimal nutrition profile. Nutrition manager 1434, therefore, is configured to motivate a user to improve the user's health and wellness by improving the user's eating habits and nutrition. According to various one or more examples, nutrition-related parameters can be acquired or derived by any of the sensors or sensor functions described in, for example, FIGS. 3 to 5E. For example, other parameters (e.g., location-related parameters identifying the user is at a restaurant, or social-related parameters describing proximity to others during meal times) can be used to determine whether a user is engaged in a nutrition intake-related activity as well the aspects thereof. In one example, acquired parameters include detected audio converted to text that describes the types of food or drink being consumed. For example, a user in the restaurant may verbally convey an order to a server, such as "I will take the cooked beef, a crab appetizer and an ice tea." Logic can decode the audio to perform voice recognition. Location data received from a sensor can be used to confirm the audio is detected in the context of a restaurant, whereby the logic determines that the utterances likely constitute an order of food. This logic can reside in nutrition manager 1434, which can be disposed in or distributed across any of a wearable computing device, an application, a mobile device, a server, in the cloud, or any other structure.

General health/wellness manager 1436 is configured to manage any aspect of a user's health or wellness in a manner similar to sleep manager 1430, activity manager 1432, and nutrition manager 1434. For example, general health/wellness manager 1436 can be configured to manage electromagnetic radiation exposure (e.g., in microsieverts), such as radiation generated by a mobile phone or any other device, such as an airport body scanner. Also, general health/wellness manager 1436 can be configured to manage amounts or doses of sunlight sufficient for vitamin D production while advising a user against an amount likely to cause damage to the skin. According to various embodiments, general health/wellness manager 1436 can be configured to perform or control any of the above-described managers or any generic managers (not shown) configured to monitor, detect, or characterize, among other things, any one or more acquired parameters for determining a state or condition of any aspect of health and wellness that can be monitored for purposes of determining trend data and/or progress of an aspect of health and wellness of a user against a target value or score. As the user demonstrates consistent improvement (or deficiencies) in meeting one or more scores representing one or more health and wellness scores, the target value or score can be modified dynamically to motivate a user to continue toward a health and wellness goal, which can be custom-designed for a specific user. The dynamic modification of a target goal can also induce a user to overcome slow or deficient performance by recommending various activities or actions in which to engage to improve nutrition, sleep, movement, cardio goals, or any other health and wellness objective. Further, a wearable device or any structure described herein can be configured to provide feedback related to the progress of attaining a goal as well as to induce the user to engage in or refrain from certain activities. The feedback can be graphical or haptic in nature, but is not so limiting. Thus, the feedback can be transmitted to the user in any medium to be perceived by the user by any of the senses of sight, auditory, touch, etc.

Therefore, that general health/wellness manager 1436 is not limited to controlling or facilitating sleep, activity and nutrition as aspects of health and wellness, but can monitor, track and generate recommendations for health and wellness based on other acquired parameters, including those related to the environment, such as location, and social interactions, including proximity to others (e.g., other users wearing similar wearable computing devices) and communications via phone, text or emails that can be analyzed to determine whether a user is scheduling time with other persons for a specific activity (e.g., playing ice hockey, dining at a relative's house for the holidays, or joining colleagues for happy hour). Furthermore, general health/wellness manager 1436 and/or aggregator engine 1410 is not limited to the examples described herein to generate scores, the relative weightings of activities, or by the various instances by which scores can be calculated. The use of points and values, as well as a use of a target score are just a few ways to implement the variety of techniques and/or structures described herein. A target score can be a range of values or can be a function of any number of health and wellness representations. In some examples, specific point values and ways of calculating scores are described herein for purposes of illustration and are not intended to be limiting.

Conversion module 1420 includes a score generator 1422 and an emphasis manager 1424. Score generator 1422 is configured to generate a sub-score, score or target score based on sleep-related parameters, activity-related parameters, and nutrition-related parameters, or a combination thereof. Emphasis manger 1424 is configured emphasize one or more parameters of interest to draw a user's attention to addressing a health-related goal. For example, a nutrition parameter indicating an amount of sodium consumed by a user can be emphasized by weighting the amount of sodium such that it contributes, at least initially, to a relatively larger portion of a target score. As the user succeeds in attaining the goal of reducing sodium, the amount of sodium and its contribution to the target score can be deemphasized.

Status manager 1450 includes a haptic engine 1452 and a display engine 1454. Haptic engine 1452 can be configured to impart vibratory energy, for example, from a wearable device 1470 to a user's body, as a notification, reminder, or alert relating to the progress or fulfillment of user's sleep, activity, nutrition, or other health and wellness goals relative to target scores. Display engine 1454 can be configured to generate a graphical representation on an interface, such as a touch-sensitive screen on a mobile phone 1472. In various embodiments, elements of aggregation engine 1410 and elements of status manager 1450 can be disposed in either wearable device 1470 or mobile phone 1472, or can be distributed among device 1470, phone 1472 or any other device not shown. Elements of aggregation engine 1410 and elements of status manager 1450 can be implemented in either hardware or software, or a combination thereof.

Figure 15A:
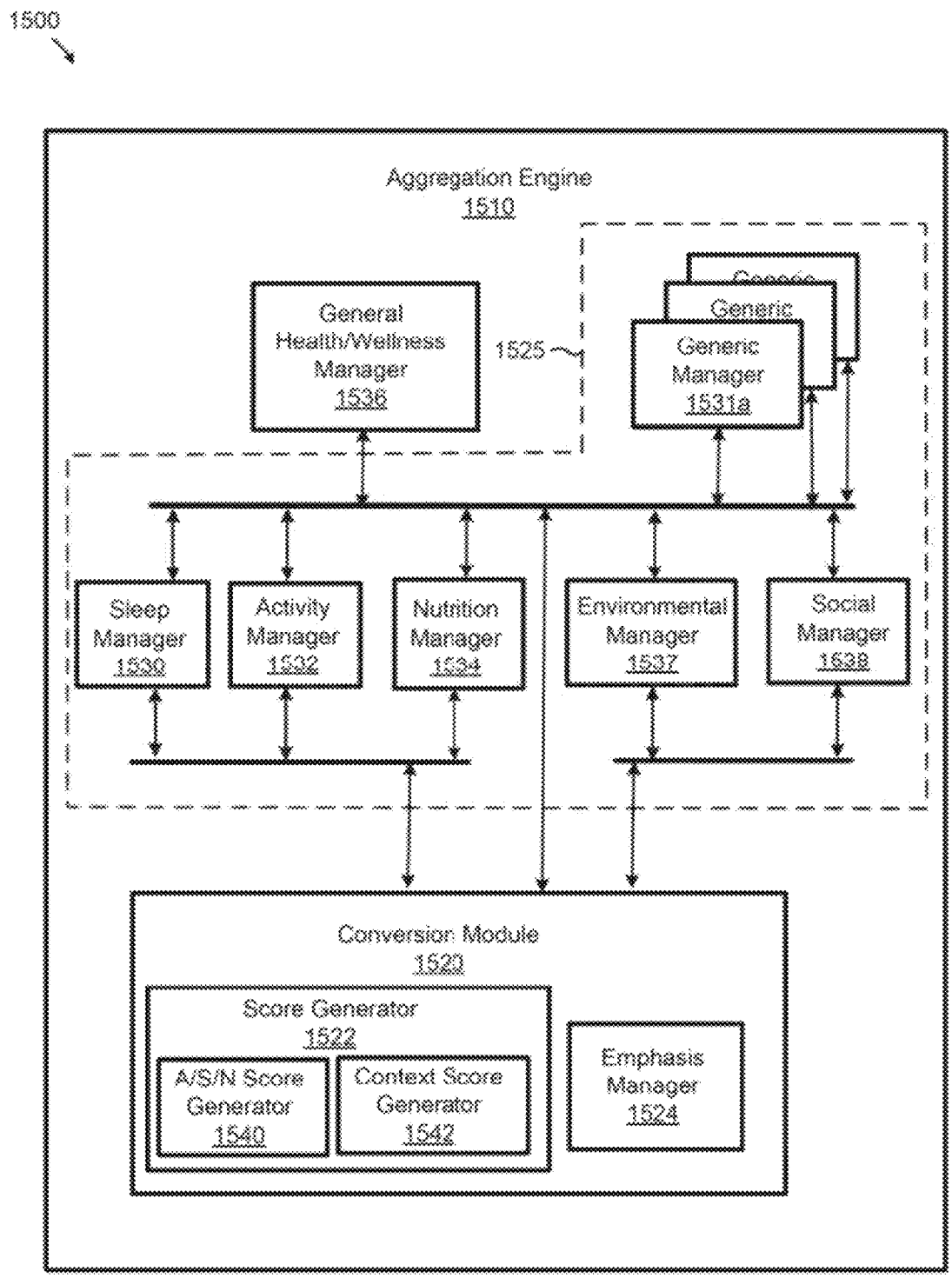
FIG. 15A depicts an example of an aggregation engine including a general health and wellness manager configured to operate with and/or control one or more managers, according to some examples.

FIG. 15A depicts an example of an aggregation engine including a general health and wellness manager configured to operate with and/or control one or more managers, according to some examples. Diagram 1500 depicts a sleep manager 1530, an activity manager 1532, a nutrition manager 1534, a general health/wellness manager 1536, an environmental manager 1537, a social manager 1535, any number of generic managers 1531*a*, and a conversion module 1520. Any of managers 1525, including general health/wellness manager 1536, can be implemented in hardware or software, or a combination thereof. For instance, a manager can be implemented as downloadable executable instructions that can be obtained via a on-line marketplace. In the example shown, general health/wellness manager 1536 is configured to assist, facilitate and/or control operations of managers 1525 to obtain acquired parametric for respective aspects of health and nutrition identified for monitoring, tracking and generating feedback. Any of managers 1525 can communicate data with any other manager 1525 to more readily detect actions, environments and socially-related events in which the use is engaged. For example, an environmental manager 1537 can determine and monitor locations, which can be used to determine whether a user is at a restaurant (e.g., engaged in nutrition intake) or on a running track (e.g., engaged in exercise).

An example of activity manager 1532 is disclosed in U.S. patent application Ser. No. 13/433,204 filed on Mar. 28, 2012, which is hereby incorporated by reference for all purposes. An example of sleep manager 1530 is disclosed in U.S. patent application Ser. 13/433,208 filed on Mar. 28, 2012, which is hereby incorporated by reference for all purposes. An example of nutrition manager 1534 is disclosed in U.S. patent application Ser. No. 13/433,213 filed on Mar. 28, 2012, which is hereby incorporated by reference for all purposes. Generic manager(s) 1531*a* represents any number of hardware and/or software implementations configured to manage the acquisition of acquired parameters for monitoring any aspect of health and wellness for purposes of, for example, tracking a user's progress and improvements toward a goal for an aspect of health and wellness (e.g., limiting amounts of sun light, limiting consumption of fish with known levels of mercury, limiting exposure to electromagnetic radiation, and any other state or conditions that affect one's health). Further, generic manager(s) 1531a facilitate score calculations relating to any specific aspect of health and wellness and can provide recommendations for improving such scores.

Environmental manager 1537 is configured to receive data representing parameters relating to an environment in which a user (or other persons of interest) is disposed, and configured to maintain data representing one or more environmental profiles. Environment-related parameters describe characteristics, factors or attributes of, for example, an environment, and can be formed from sensor data or derived based on computations. In some examples, environment-related parameters can be acquired or derived by any of the sensors or sensor functions described in, for example, FIGS. 3 to 5E. Examples of environmentally-related parameters include a location (e.g., absolute in terms of geometric coordinates via GPS, or approximate coordinates based on triangulation of radio signals, etc.), and perceptible aspects of an environment, such as audio aspects (e.g., spoken words detectable to determine certain activities related to nutrition intake, exercise, etc.) or visual aspects. Examples of environmentally-related parameters also include data representing vibrations or motion that a wearable device is experiencing (e.g., the user is traveling in a car), locations of identified friends or users of other wearable computing devices in communication with each other, locations of destinations or originations, locations of places to avoid (e.g., a food court in a mall) or to migrate toward (e.g., another user that is participating in a similar activity), numbers of people on a jogging route (e.g., to ensure an optimal running route), atmospheric pressures, whether the wearable device is submerged in water, and any other parameter that defines or describes an environment of interest. Other environmentally-related parameters include data representing health and wellness characteristics of a location (e.g., general health or characteristics of people visiting a location), such as a stadium, restaurant, or a home, or of a region (e.g., general health or characteristics of people living in a region, such as rates of alcoholism, obesity, etc. of a city, county or state). Such data can be used to influence score calculations and/or recommendations. The above-described examples are not intended to be limiting. Environmental manager 1537 is configured to also generate trend data relating to locations and other activities a user is engaged to predict a future activity (e.g., a dance class) that is possible based on past visits to a location (e.g., a gym).

Social manager 1538 is configured to receive data representing parameters relating to social interactions and proximities to others relative to a user (or other persons of interest). In some examples, social-related parameters can be acquired or derived by any of the sensors or sensor functions described in, for example, FIGS. 3 to 5E, including mobile phones and computing devices. Social-related parameters describe characteristics, factors or attributes of, for example, a social network of a user, and can be formed from sensor data or derived based on computations. Examples of social-related parameters include data representing family and friends, and, optionally, aspects of their health and wellness, and data representing other users of wearable devices, and, optionally, aspects of their health and wellness, too. For example, friends 1, 4 and 7 can be identified from their health and wellness profiles, overall scores or targets scores to be active friends. Examples of other social-related parameters include data representing proximities to other wearable devices and information describing interactions or future interactions with others. For example, social-related parameters can include data derived from phone calls (e.g., decoded audio and speech into text, caller ID information, date, time, etc.), emails, texts, and other communications in which a user is arranging an activity with other persons. Social-related parameters can also include data from or exchanged with various networking web sites in which users exchange information between one or more levels of permissions (e.g., usually based on friendships or as acquaintances). General health/wellness manager 1536 can use this information to generate recommendations on whether to associate with active persons rather than inactive persons and to predict types of activities a user is engaged in base on, at least in part, the information derived from communications and interactions with others. Also, social manager 1538 is configured to generate recommendations to induce users to socialize with others with similar goals or to reinforce favorable habits (e.g., telling a person next to the user a good reasons to drink water). The above-described examples are not intended to be limiting.

Conversion module 1520 includes a score generator 1522 and an emphasis generator 1524, according to some examples. The functionality and/or structure can be equivalent to similarly-named elements described herein. Score generator 1522 can include an activity-sleep-nutrition ("A/S/N") score generator 1540 configured to calculate one or more scores based on activity, sleep, nutrition-intake or any other aspect of health and wellness for a user, and a context score generator 1540 configured to calculate one or more scores based on the environment and/or social interactions (or proximities) between a user and other people. In some examples, context score generator 1540 generates a context score that indicates a context in which a user is disposed or in which a user is performing an activity. The context score can be used to influence a score to provide motivation and inducements to a user to meet one or more health and wellness objectives, responsive to environmental and social factors.

Figure 15B:
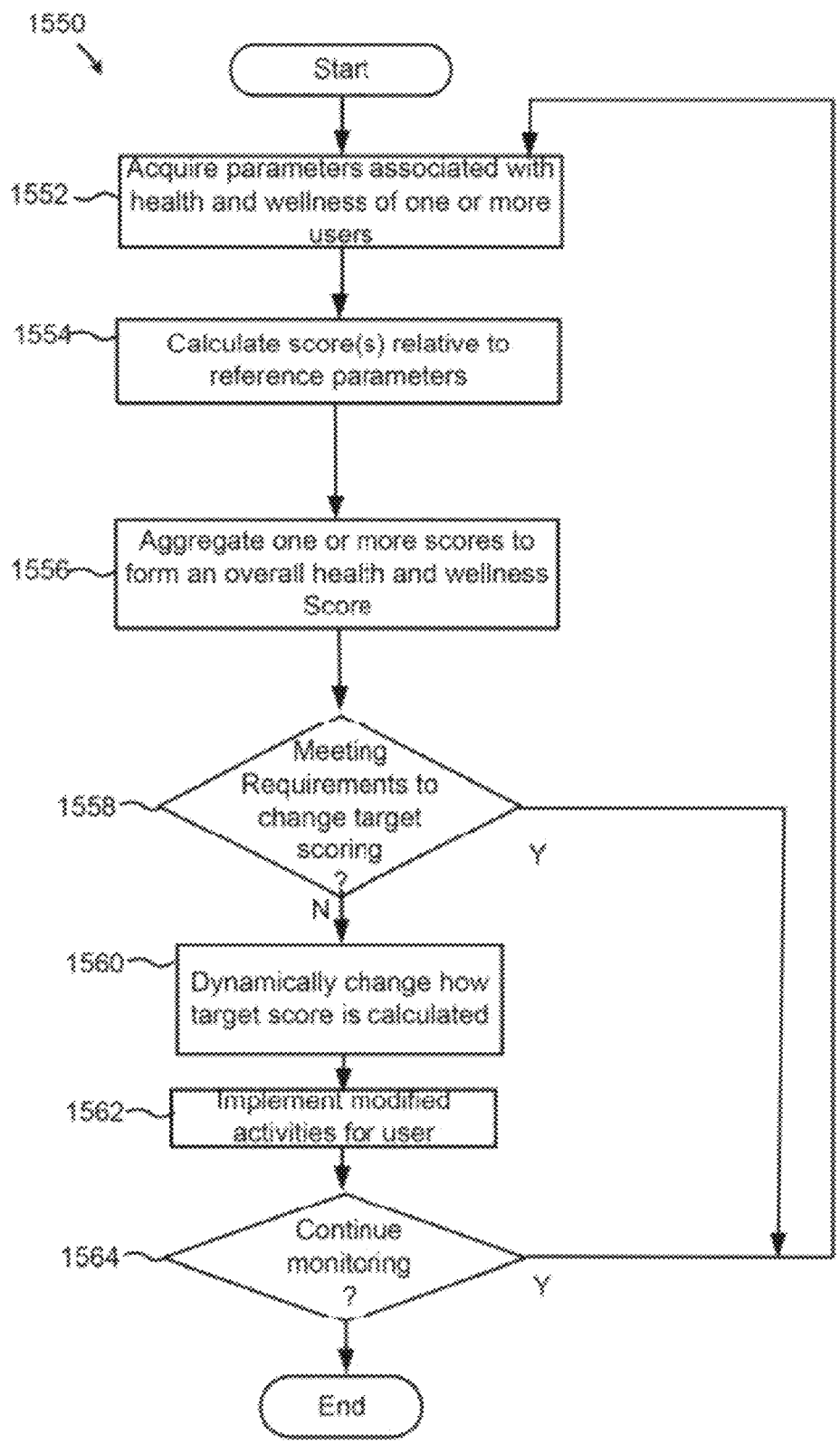
FIG. 15B depicts an example of a flow to modify a target score to enhance a general health and wellness of a user, according to some examples.

FIG. 15B depicts an example of a flow to modify a target score to enhance a general health and wellness of a user, according to some examples. At 1552, parameters describing any aspect of health and wellness is captured (i.e., acquired), and one or more scores are calculated at 1554 (e.g., a score can represent a user's ability to attain a targeted goal for one aspect of health and wellness, such as sleep, nutrition, etc.). At 1556, the one or more scores are aggregated to form an overall health and wellness score, which can be compared against a target score indicative of an optimal state or conditions of health and wellness for a user. At 1558, once requirements are met to change the methods of calculating a target score, the new target score is dynamically changed at 1560 based on the user's progress or continued progress. In particular, a determination is adjusted upon which to modify the target score, the determination being based on, for example, a calculation expressing activities in which a user is to engage to meet its health goals. In some cases, the requirements to change the calculations of a target score are based on the user consistently attaining a certain level or overall score. The new target score calculations ensure the user is motivated or induced to continue to improve his or her health at least until the target scoring is again modified. At 1562, modified activities are implemented for the user. That is, the types and amounts of an activity can be "leveled up," so that user is challenged further. The flow continues monitoring at 1564.

Figure 16A:
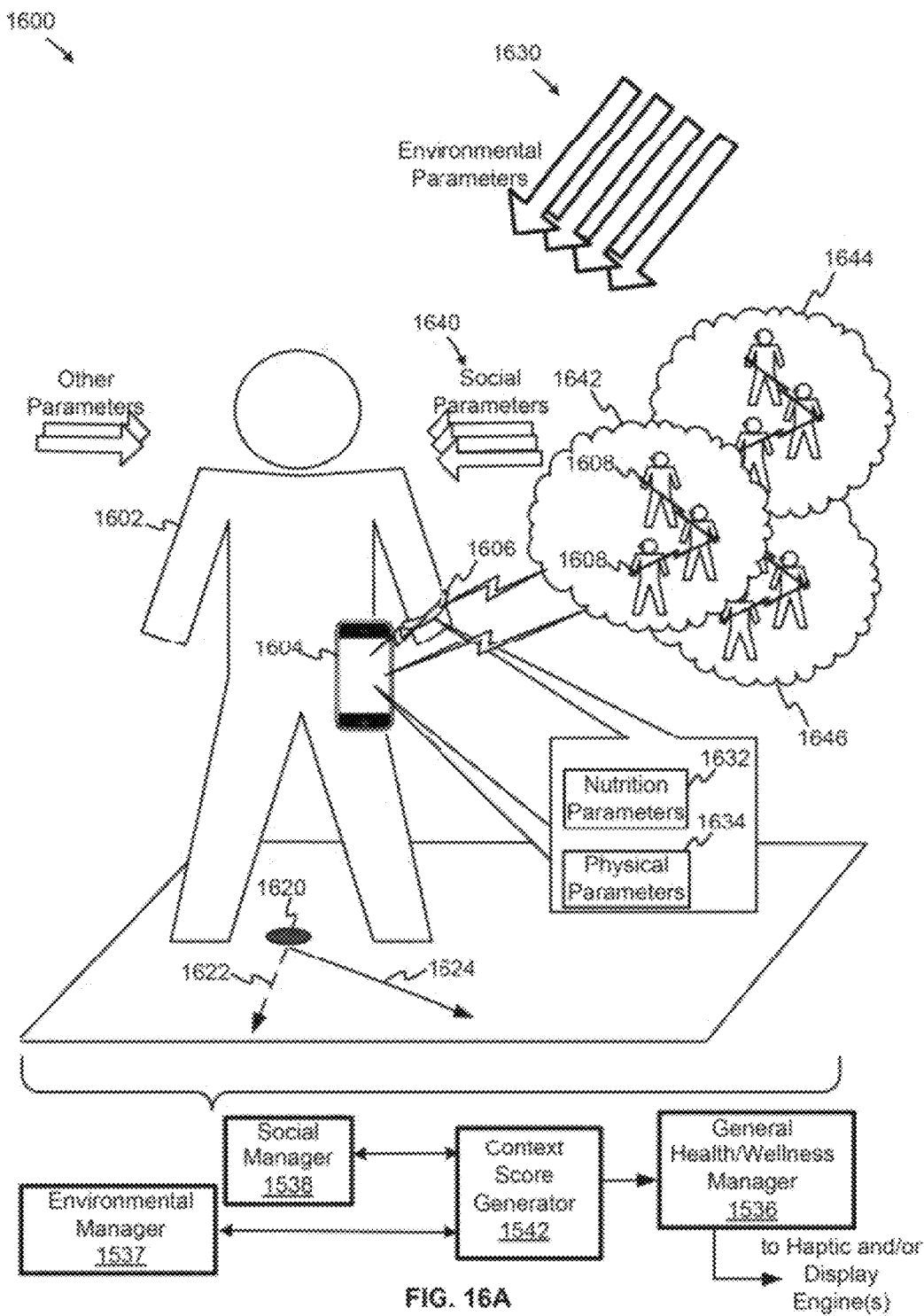
FIG. 16A depicts examples of a social manager and an environmental manager configured to generate a context score, according to some examples.

FIG. 16A depicts examples of a social manager and an environmental manager configured to generate a context score, according to some examples. Diagram 1600 shows a user 1602 at a location 1620 subject to its environment from which environmental parameters 1630 (e.g., location, temperature, noise levels, atmospheric pressure, talking or speech levels, etc.) can be acquired. Further, social parameters 1640 can be acquired. Examples of social parameters 1640 include a number of people wearing wearable devices 1608 contemporaneously, in proximity to the user, and/or engaged in similar activities or movements. User 1602 (or accompanying devices) can be interacting in a manner with others to receive and/or exchange social parameters 1640 from a social network of friends 1642 have a certain level of authorization or permissions to interact with user 1602 (and/or mobile devices 1604 and wearable device 1606). Persons described as friends may or may not include wearable devices 1608 as part of a social network based on networked wearable devices. In some cases, mobile devices 1604 and/or wearable device 1606 are configured to communicate with a larger subset of persons (e.g., a universe of users using wearable devices 1608 in networks 1644 and 1646). In some cases, nutrition parameters 1632 and/or physical parameters 1634 of user 1602 (and other authorized users), or an overall score based on those and others parameters, can be exchanged one or more social networks 1642, 1644, and 1646.

Diagram 1600 also shows social manager 1538 and an environmental manager 1537 configured to exchange data with context score generator 1542. For example, social manager 1538 and environmental manager 1537 can transmit to context score generator 1542 values of acquired environmental parameters 1630 and values of acquired social parameters 1640. Social manager 1538 and/or environmental manager 1537, as well as general health/wellness manager 1536, can be configured to facilitate social networks and the functionalities and/or structures are described in FIGS. 12A to 12F.

Context score generator 1542 generates a context score that is indicative of the degree of impact caused by either an aspect of the environment or social interactions, or both, in relation to user 1602. For example, a context score can be negatively impacted if user 1602 lives or spends time in regions of high rates of obesity, or with a group of people that tend to be sedentary, or at bars and nightclubs. However, the context score can be positively influenced by spending time at or near areas of relatively high occurrences of physical activities (e.g., spending time on a basketball court) or having a network of active friends. The context score is provided to general health and wellness manager 1536 to optionally influence an overall score (e.g., including sleep, nutrition and activity scores) relative to a target score. Responsive to a context score, general health and wellness manager 1536 can generate recommendations. For example, general health and wellness manager 1536 can determine that a user is at a specific location and can recommend one or more activities associated with that location or a structure at that location. If user 1602 is at a stadium, general health and wellness manager 1536 can generate recommendations to climb a number of stairs associated with the stadium structure, or can suggest a glass of water rather than a beer with a hot dog. If user 1602 is at a shopping mall, mobile devices 1604 and/or wearable device 1606 can project a path 1622 that passes a food court and recommend altering course onto another path 1624 to avoid the food court or to connect socially with another user sharing, for example, similar health and wellness profiles (i.e., goals). Therefore, general health and wellness manager 1536 can generate recommendations based on acquired parameters received by any sleep manager, activity manager, nutrition manager, environmental manager, social manager, or any number of generic managers to determine an overall score relative to an overall target score and can propose actions that affect one aspect of health, and wellness (e.g., sleeping) based on one or more other aspects of health and wellness (e.g., environment, nutrition, etc.).

In some embodiments, wearable device 1606 can generate messages encoded in vibratory messaging. For example, two long vibratory pulses can indicate that user 1602 ought to turn right and three short vibratory pulses can indicate that a user 1602 turn left. This vibratory messaging scheme can assist navigation of user 1602 to avoid detrimental locations, such as a food court, or can assist user to select a less populous running route based on data originating from a server that describes a number of pedestrians and cyclists based on locations of other wearable devices 1606 or cell phone locations (e.g., base on triangulation, GPS, or other means). The vibratory energy can increase as the user 1602 comes closer to a point at which to turn and decreases once the user passes that point.

Figure 16B:
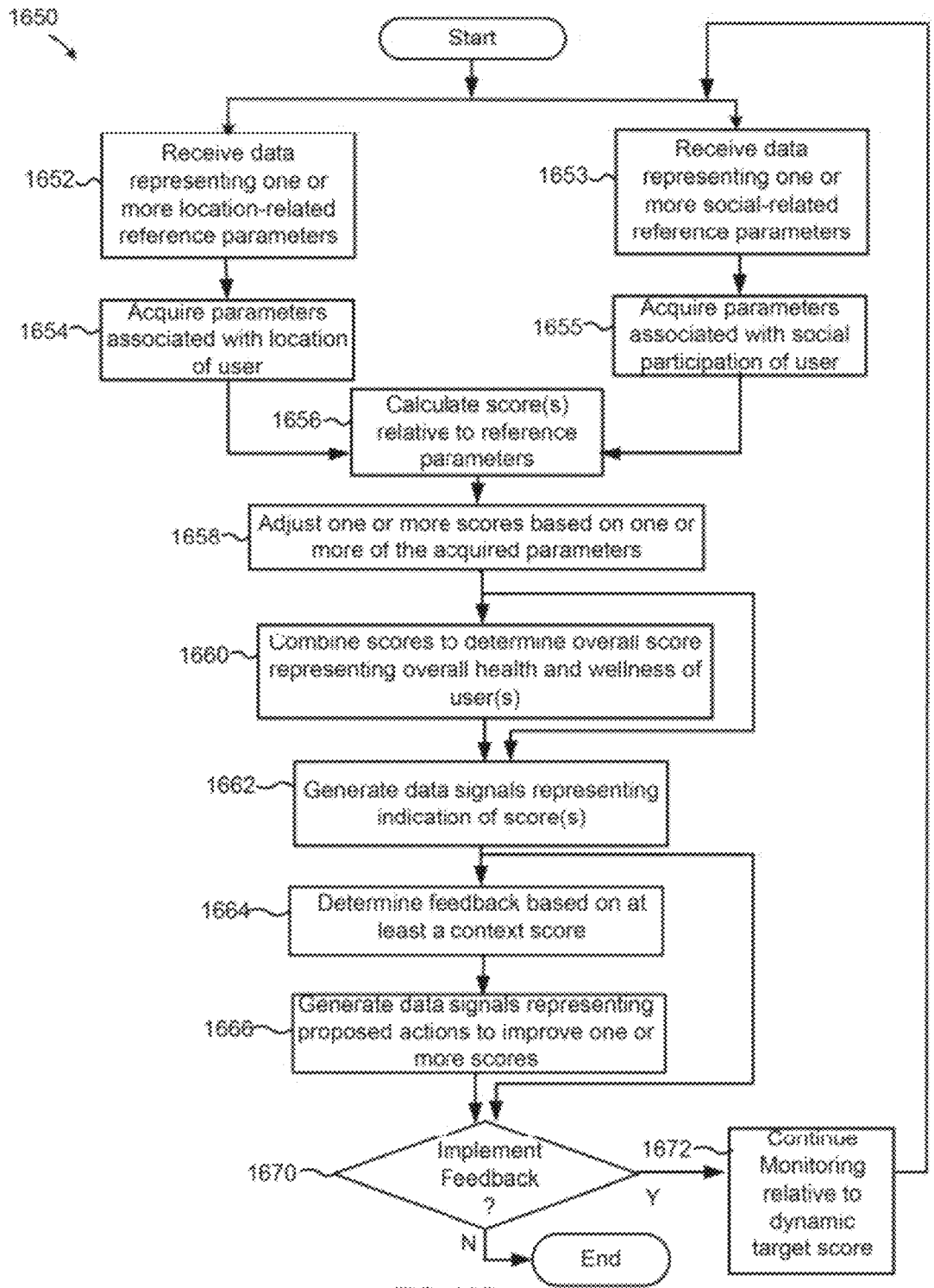
FIG. 16B is an example of a flow diagram to determine recommendations based on a context score to manage health and wellness, according to some examples.

FIG. 16B is an example flow diagram 1650 to determine recommendations based on a context score to manage health and wellness, according to some examples. At 1652, data representing one or more location-related reference parameters are received. For example, the one or more location-related reference parameters can include data representing what structures exist at the location and what activities typically occur there. At 1654, acquired parameters associated with the location of a user are obtained. Optionally, data representing one or more social-related reference parameters are received at 1653. For example, the one or more social-related reference parameters can include data representing the degree to which one or more friends, colleagues or people are active or participate in similar activities. At 1655, acquired parameters associated with the social participation of a user are obtained. At 1656, one or more scores are calculated relative to reference parameters. For example, positive values may be used in calculations when a user is interacting with active people, and negative values may be used when a user spends more than a certain amount of time at a bar or sitting at a location in front of a television. Scores can be adjusted optionally at 1658 to emphasize or deemphasize either positive actions or detrimental actions of a user. At 1660, scores are combined to determine an overall score that represents the overall heath and wellness of one or more users. That is, an overall score can be based on a single user or a group of users, whereby those in the group can be linked together to induce encouragement in achieving health and wellness goals. At 1662, data signals representing one or more scores are generated to present to a user, for example, via visual means, such as a display, or haptic means, such as vibratory energy. Feedback can be determined at 1664 based on context score, and one or more proposals incorporating the feedback can be embodied in data signals at 1666 to propose actions for improving one or more scores. A determination whether to implement the feedback is made at 1670. If it is, then flow 1650 continues to monitor acquired parameters and calculating scores to determine, if applicable, to dynamically change the target score to reflect the user's improvements and to further incentivize or motivate the user.

Figure 16C:
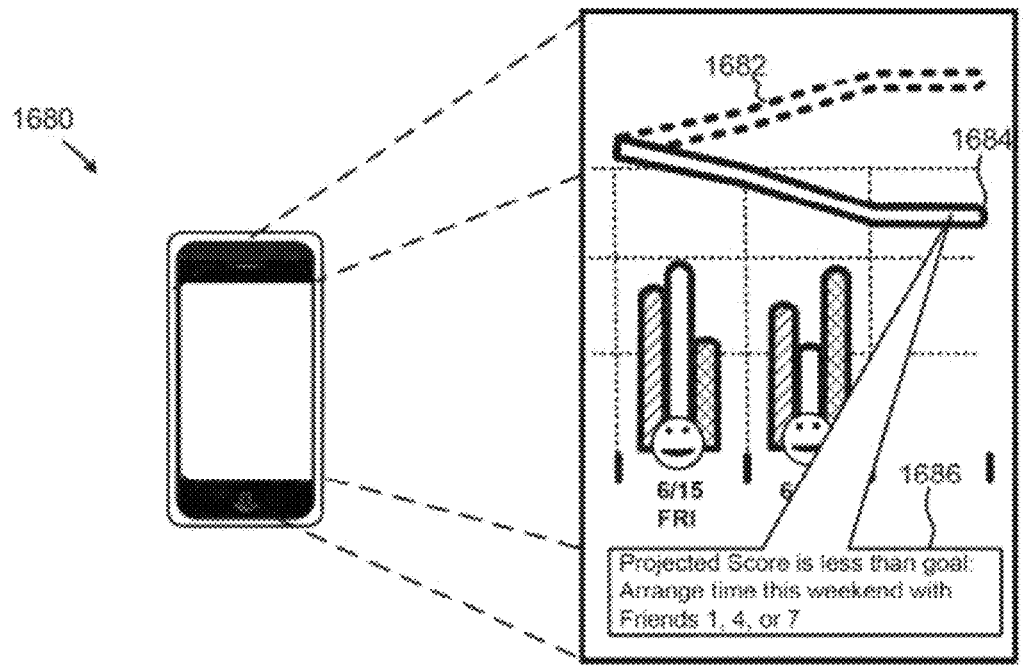
FIGS. 16C and 16D depict examples of displays including feedback based on environmental or social parameters, according to some examples.
Figure 16D:
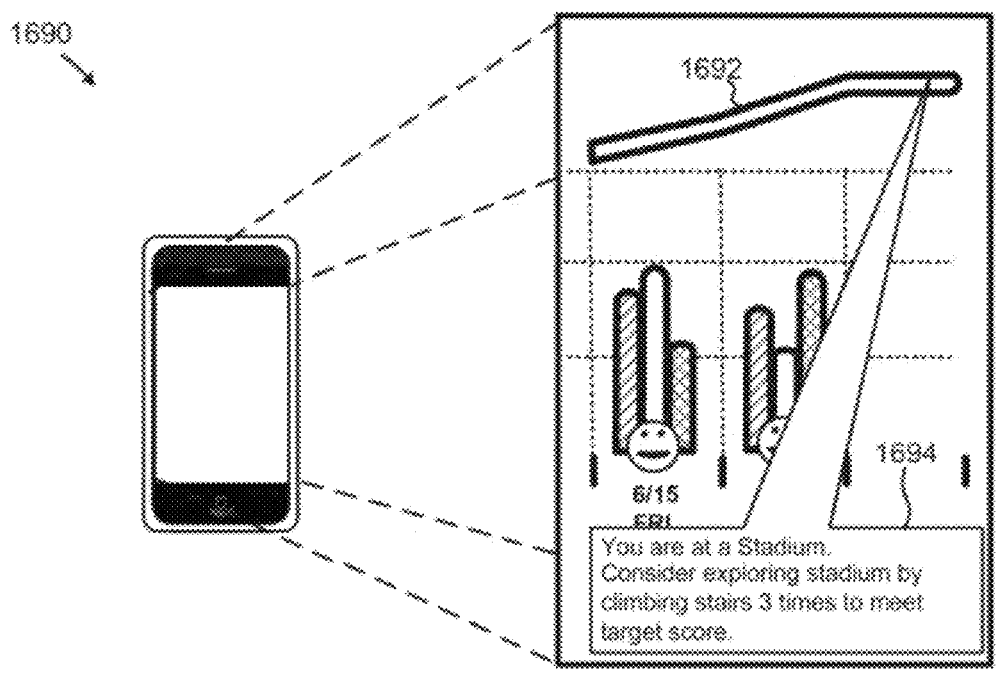

FIGS. 16C and 16D depict examples of displays including feedback based on environmental or social parameters, according to some examples. In FIG. 16C, a display 1680 of a mobile device can depict a target score 1682 and a recommendation 1686 based on social parameters to encourage the user to alter score 1684 to meet target score 1682. In FIG. 16D, a display 1690 of a mobile device can depict a target score 1692 and a recommendation 1694 based on environmental parameters to encourage the user to achieve target score 1692. Note displays are not limited to displays 1680 and 1690 and can be disposed on a wearable device and can convey information via different media other than visual (e.g., auditory, perceptible by touch, etc.).

Figure 17A:
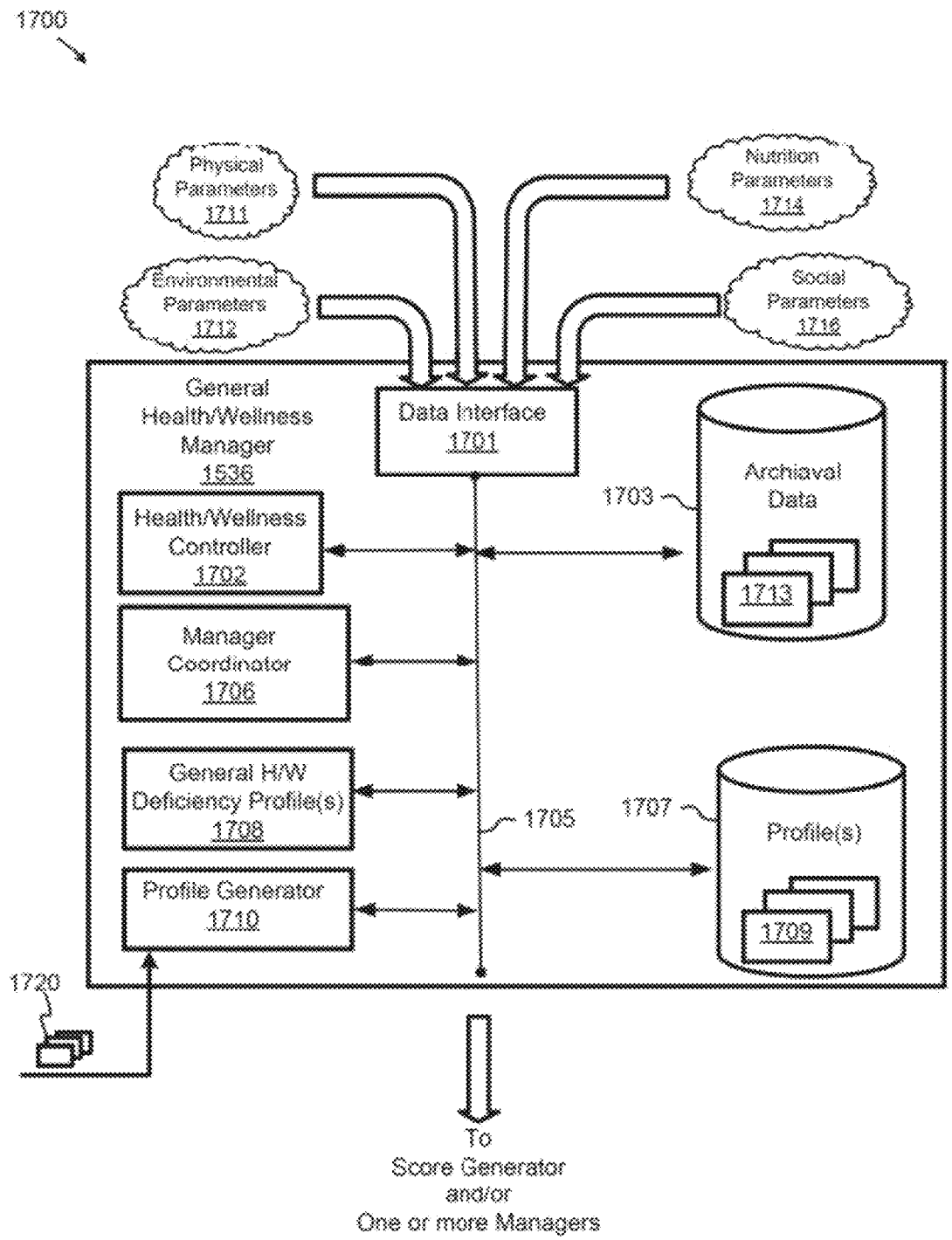
FIG. 17A depicts an example of a general health and wellness manager, according to some examples.

FIG. 17A depicts an example of a general health and wellness manager, according to some examples. Diagram 1700 depicts general health and Wellness 1536 including one or more of the following: a data interface 1701, a health and wellness evaluator 1702, a manager coordinator 1706, a repository 1703 configured to store data representing trend or archival data files 1713, a repository 1707 configured to store data representing one or more profiles 1709, and a profile generator 1710. A bus 1705 couples each of the elements for purposes of communication. Profile generator 1710 can generate one or more profiles representative of a user's patterns of various activities associated with certain aspects of health and wellness based on trend analysis (e.g., empirically over time and various cycles of meals, sleep, time at certain locations, social interactions, and the like. A profile for a user can be input or entered via data 1720 to establish an initial over health and wellness profile based on one or more aspects thereof. Profile generator 1710 can generate data representing a subset of acquired parameters to establish a baseline profile against which a user's progress can be measured in modifying behavior when working toward a goal (e.g., overall target score) that is consistent with a healthy lifestyle. For example, the profile generated by profile generator 1710 can represent a daily average of activities affecting various aspects of health and wellness over one or more days during which acquired parameters were used to determine the trends for a user. Or, the profile generated by profile generator 1710 can represent a current interval of time (e.g., a specific day) in which an aspect of a user's health and wellness is monitored, and optionally modified to conform the user's behavior to a set of behaviors associated with a target score, which can be determined by a profile 1709.

Data interface 1701 is configured to receive data representing parameters, such as physical parameters 1711, environmental parameters 1712, and nutrition parameters 1714. Such parameters can originate at any type of sensor, such as those described herein, or can be derived (e.g., computationally), or can be input as data extracted, for example, from a networked database. Examples of physical parameters 1711 include a sleep start time, a sleep end time, a duration of light sleep (and/or a total duration of light sleep between the start and sleep end times), a duration of deep sleep (and/or a total duration of deep sleep between the start and sleep end times), a heart rate, a body temperature, and the like. Examples of environmental parameters 1712 include an amount of light, a level of sound energy, an ambient temperature, a location of a user, a location of another user, and the like. Environmental parameters, as well as any other parameter, can be archived in archived data files 1713 so that trends can be established to determine, for example, the locations at which a user tends to participate in positive activities (i.e., in terms of achieving a target score). This information can be used to generate recommendations to induce a user toward achieving a target score. Parameters also can include nutrient-related parameters that causes physiological manifestations in, for example, types of gases, such as $CO_2$ expelled from the lungs or skin, as well as steps, minutes of activity/motion, minutes of inactivity/no motion, intensity of activity, aerobic minutes, aerobic intensity, calories burned, training sessions, length, of training sessions, intensity of training sessions, calories burned during training session(s), type of activities, duration of each type of activity, intensity of each type of activity, calories burned during each type of activity, instantaneous body temperature, average body temperature, instantaneous skin galvanization, average skin galvanization, instantaneous heart rate, average heart rate, instantaneous perspiration, average perspiration, instantaneous blood sugar level, average blood sugar level, instantaneous respiration rate, average respiration rate, and the like.

Examples of nutrition parameters 1714 include types of consumable materials and their nutrient compositions for specific unit amounts or volume. As used herein, the term "consumable material" refers to any material consumed as either food or drink and has at least one or more nutrients from which to provide a user. A consumable material can be medicine or any other substance that enters the body (e.g., orally or by any other means, such as through the skin or is inhaled). A "consumable material component" is a component of a meal, such as a side salad, French fries, or a main entrée, that, when combined with other meal components, form a meal. Each of the consumable material components can have equivalent nutrients, such as sodium, that can be isolated, measured, monitored and reported as an aggregate amount of the specific nutrient for the meal (i.e., over all the parts of the meal containing that nutrient). In some embodiments, nutrition parameters 1714 can be stored as nutrition parameter data 1713. Types of consumable materials include unprocessed foods and drink, such as fruits, vegetables, unprocessed meats, water, etc., and processed foods and drink, such as restaurant meals, processed and packaged foods, etc. Nutrition parameters 1714 can include descriptors specifying amounts of the nutrients, such as units (e.g., real numbers representing units of measure, such as IUs, mg, g, ml, cups, etc.), and types of nutrients. Types of nutrients can include carbohydrates (of a various subtypes, including fiber), fats, minerals, proteins, vitamins, water, and any combination or variation thereof. Data representing nutrition parameters can be acquired (e.g., as acquired parameters) by way of input by a user. A social parameter includes data representing a social interaction between a user and another person via any form of communication, such as face-to-face, phone, email, text, amounts of time spent with a person, and the like. Social parameters can be archived in archived data files 1713 so that trends can be established to determine, for example, the people with which a user tends to participate in positive activities (i.e., in terms of achieving a target score). This information can be used to generate recommendations to induce a user toward achieving a target score. Any other characteristics of social interactions, including proximity to other persons (or the proximities of wearable devices relative to each other) and data derived from social networking web sites and other databases are also included in social parameters 1716. As used herein, the term "acquired parameter" refers to one or more parameters that are obtained for purposes of analyzing nutritional intake (e.g., nutrition parameters describing nutrition of food or drink that is consumed or to be consumed). Data representing an acquired parameter can include an amount (e.g., units) of a nutrient and a type of the nutrient. In some embodiments, an acquired parameter is associated with data originating from a wearable computing device. In some embodiments, nutrition parameters 1714 can be retrieved from repository 1703 or over a network from a remote database. For example, a restaurant or food producer may provide access to nutrition data in a remote database that is accessible by customers for purposes of evaluating nutrition for health and wellness. In at least some examples, nutrition parameters 1714 can be determined via image capture with image recognition logic and/or user input. An example of the use of image recognition logic is shown in FIG. 17B.

Health and wellness evaluator 1702 is configured to acquire data representing acquired parameters describing the various aspects of health and wellness of a user, including, but not limited to, nutrition-related characteristics, sleep-related characteristics, movement-related characteristics, environmental characteristics, social-related characteristics, among others. In particular, health and wellness evaluator 1702 is configured to determine characteristics of an activity, state or condition for a user. Health and wellness evaluator 1702 is further configured to identify the a specific activity and type of activity (e.g., type of sleep, movement, nutritional intake, etc.) and generate data representing the units and types of the activities for specific aspects of health and wellness. In some examples, health and wellness evaluator 1702 is configured to control manager coordinator 1706, which, in turn, is configured to facilitate, assist with or control operations of various managers, as well as interactions between the managers. The managers can operate cooperatively to tune or modify the interrelationships between multiple behaviors or activities of a user to maximize various aspects of health and wellness. For example, manager coordinator 1706 can cause generation of recommendations to improve one or more scores of the same or different aspects of health and wellness. Exemplary operation of manager coordinator 1706 is described by way of several examples of tuning the interrelationships between multiple behaviors and activities of a user, as described in FIGS. 18A to 18D.

In some embodiments, health and wellness evaluator 1702 also is configured to compare a user's profile (i.e., trend data representing aspects of health and wellness of a user) against data representing one or more health and wellness deficiency profiles 1708 to determine whether a deficiency exists (e.g., an irregular eating schedule, a lack of proper hydration, whether a nutrient deficit exists, whether a user spends extraordinary time in the ice cream isle of a supermarket, etc.). As described above, manager coordinator 1706 is configured to provide recommendations to modify the user's behavior to optimize one or more scores, including an overall score, thereby optimizing the various user activities to facilitate improved health and wellness. Health and wellness evaluator 1702 can generate notifications and alerts (e.g., graphical, haptic, audio, or otherwise perceptible to a user) to induce a user to modify user behavior, or environmental, social, nutritional, and/or physical parameters to improve a user's health. For example, a wearable device can vibrate to notify a user that a meal ought to be consumed at a certain time, or a certain movement ought to be performed. In some examples, health and wellness evaluator 1702 is configured to cause generation of a graphical representation on an interface to induce modification of an acquired parameter, or to cause generation of a haptic-related signal for providing vibratory feedback to induce modification of the acquired parameter.

Figure 17B:
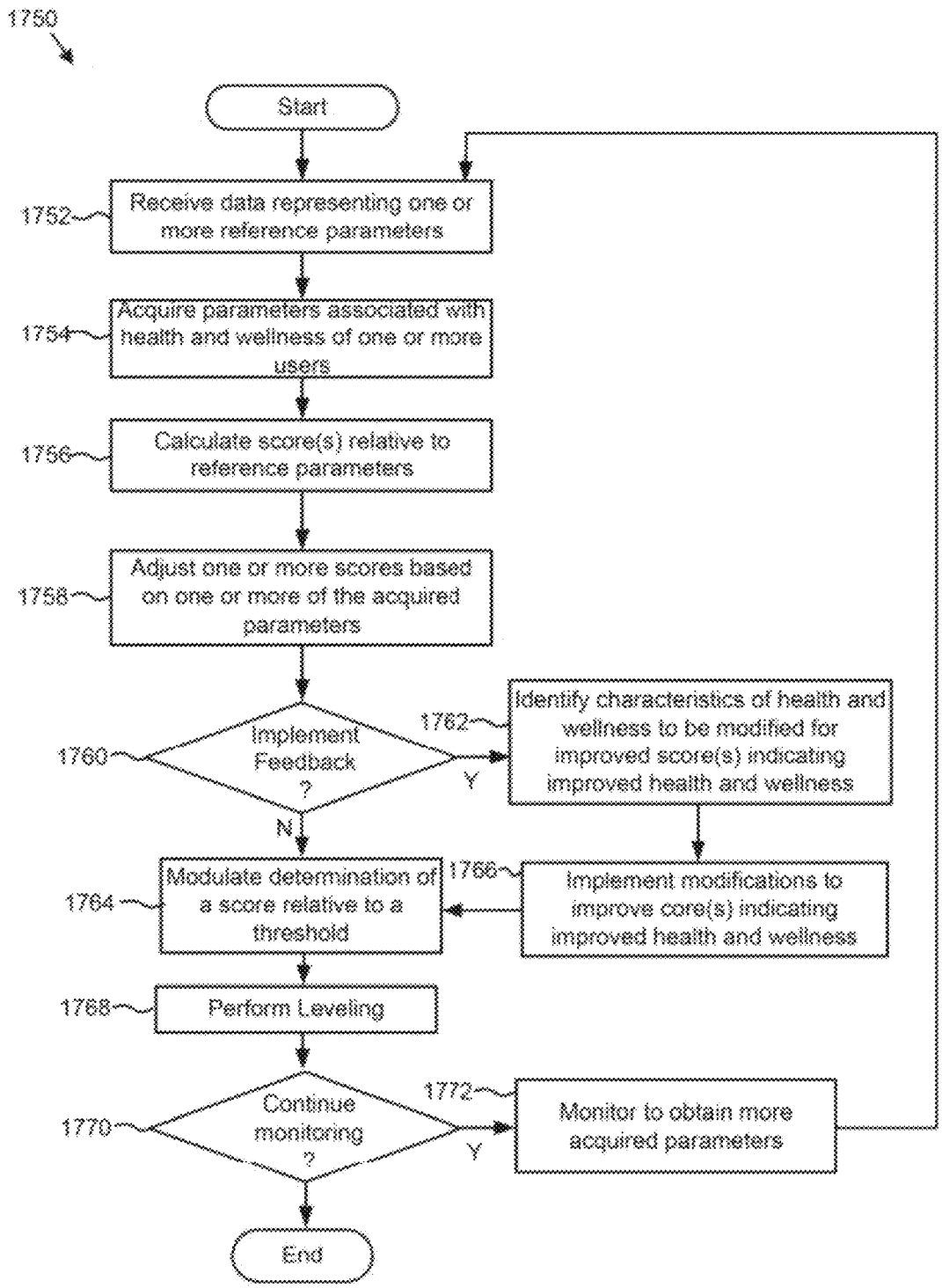
FIG. 17B is an example flow diagram for a technique of managing overall health and wellness using, for example, wearable devices that include sensors, according to some examples.

FIG. 17B is an example flow diagram for a technique of managing overall health and wellness using, for example, wearable devices that include sensors, according to some examples. At 1752, data representing one or more baseline parameters is received. The baseline parameters can include any health-related characteristics that define parameters upon which a target score is established. Further, the target score can be established based on one or more health-related activities. For instance, the baseline parameters can be set forth in a data arrangement constituting a profile 1709 of FIG. 17B. In some cases, the values of the baseline parameters are such that if the user attains or fulfills the goals of optimizing one or more aspects of health and wellness, the target score having a value of 100. At 1754, parameters are acquired that describe a state or characteristics of a user's activity. Examples of acquired parameters can include—via derivation or measurement—a heart rate, a duration of sleep, a location, a duration of wakefulness, a sleep start time, a sleep end time, a body temperature, an ambient temperature, an amount of light, an amount of sound energy, a unit and type of one or more consumable materials (e.g., food and/or drink), an indication of participating in an activity with other users, etc.

Scores are calculated at 1756 relative to or associated with baseline parameters, which can be associated with a reference value. For example, data representing values (e.g., points) for one or more subsets of acquired parameters (e.g., data via measurement, sensor, derivation, etc.) are determined based on reference values, such as a total number of points, for parameters set forth in the profile. For example, a user may set as its goal to consume 45 milligrams of vitamin C per day (per World Health Organization standards). At breakfast, the user consumes a meal and receives about 22 milligrams. A profile includes data that equates 45 milligrams as 20 points (i.e., a target score for this nutrient). In this case, 20 points is a reference value (i.e., the baseline parameter). As 22 milligrams, which represents an acquired parameter (e.g., units of: 22 mg, and type of: vitamin C nutrient), is approximately half of the goal, the user receives 10 points as the value. Scores can be calculated at a first processor based on data representing the values, whereby the score representing an attained portion of the one or more health-related activities. That is, a score can be determined as an "overall score" to include one or more of nutrition scores, sleep scores, activity scores, context scores or any other score, and the like. The overall score is indicative of an ability of a user to achieve a targeted level of health and wellness and can represent the user's progress, for example, on a daily basis in meeting a target score. The overall score can be express as a percentage of the target score, such as 71% with 100 points set as the target score.

At 1758, at least one score can be adjusted toward or away from the target score. For example, if the user is agrees to spend time with active friends, then the user is awarded positive points to encourage socializing with people more likely to assist the user in reaching its health and wellness goals. But if a user spends a certain amount of time at a bar or in the dessert isle of a supermarket, then points are deducted from its overall score to encourage the user to avoid tempting locations. At 1760, a decision is made as to whether to implement feedback. If so, flow 1750 moves to 1762, at which characteristics of health and wellness are identified for modification to urge the user to improve scores, which, in turn, represents improved health. At 1766, the modifications are implemented.

At 1764, the determination of a score can be modified relative to a threshold. For example, when the overall score exceeds the target score, the rate at which the overall score can be reduced as a function of the difference between the overall score and the target score. That is, it gets more difficult to accrue points for the overall score when exceeding the target score. For example, for overall scores between 100 and 110, it is 50% harder to obtain overall score points (e.g., 25% fewer points are rewarded), for overall scores between 111 and 125, it is 75% harder to obtain overall score points, and for overall scores above 126 it is 100% harder. At 1768, a classification for a user can be either leveled up or down. For example, a subset of overall scores can be determined and the classification associated with a user can be changed based on the subset of overall scores. The classification can be changed by leveling up to a first health and wellness profile if the subset of overall scores is associated with a first range, or the classification can be changed by leveling down to a second health and wellness profile if the subset of overall scores is associated with a second range. The first range of activity scores are nearer to the target score than the second range of activity scores. To illustrate, if the overall score is 95% of the target score (e.g., for a duration), the user is either leveled up or provided the opportunity to level up to implement, for example, a new value of a parameter of a different health and wellness profile. But if the sleep score is 70% or less of the target score, the user is given the option to level down (e.g., to a less ambitious or rigorous health and wellness profile). In this manner, the target score is dynamically altered just beyond the current limitations of the user to induce or otherwise motivate the user to work harder and strive to attain the new target score, and, ultimately, a healthy lifestyle. At 1770, flow 1750 determines whether to continue monitoring and moves to 1772 to do so. At 1772, other parameters are acquired and further monitoring is performed. Note that more or less blocks, elements, actions or steps of flow 1750 can be implemented, and note further that flow 1750 is not intended to be limiting.

Figure 18A:
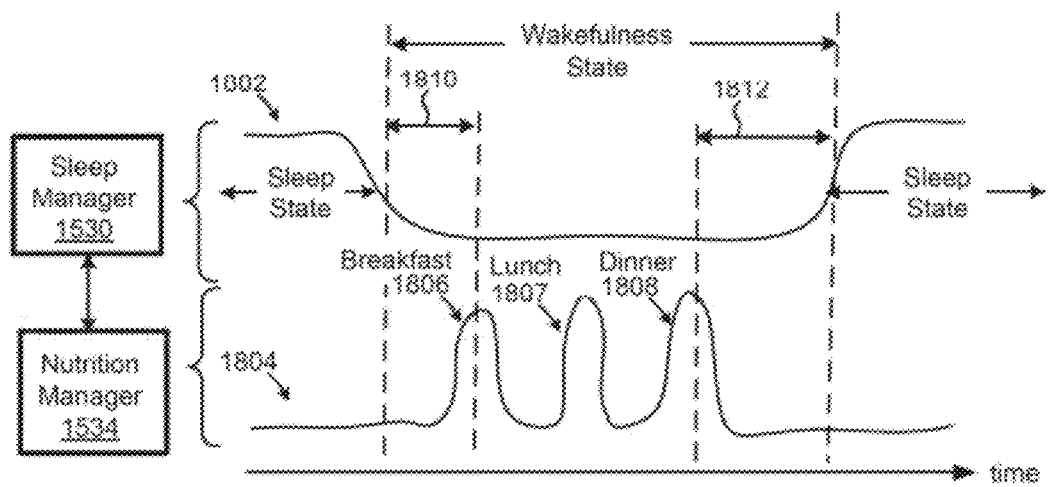
FIGS. 18A to 18D depict interrelationships between different aspects of health and wellness and different managers cooperating to optimize the same, according to various examples.

FIGS. 18A to 18D depict interrelationships between different aspects of health and wellness and different managers cooperating to optimize the same, according to various examples. FIG. 18A depicts data 1802 representing sleep and data 1804 representing nutrition-intake activity relative to time, whereby the data can represent instantaneous (e.g., in real or near real time) sleep data and nutrition data, or data 1802 and 1804 can represent archived or trend data, or projected activity occurring typically at different times during a day. Sleep manager 1530 and nutrition manager 1534 cooperate to modify one aspect of health and wellness, such as nutrition, to optimize another. For example, sleep manager 1530 can determine instantaneous or predicted states of wakefulness and sleep for a user, and nutrition manager 1534 can determine or predict nutrition intake as breakfast 1806, lunch 1807, and dinner 1808. In some cases, either manager coordinator 1706 or health and wellness evaluator 1702, or both, can control sleep manager 1530 and nutrition manager 1534. In operation, manager coordinator 1706 or health and wellness evaluator 1702 can be configured to propose a time or duration 1810 in which a user is recommended to have breakfast 1806 after waking up. Positive or no points can be awarded if this meal occurs during interval 1810, and negative points can be applied if the user fails to eat breakfast. Further, manager coordinator 1706 or health and wellness evaluator 1702 can be configured to recommend to a user to have dinner no later than an amount of time 1812 before bedtime. Positive points can be awarded if dinner 1808 occurs before time 1812 or include a meal conducive to enhance sleep, such as foods with tryptophan. Negative points may be applied if caffeine or other stimulants are consumed during time 1812.

Figure 18B:
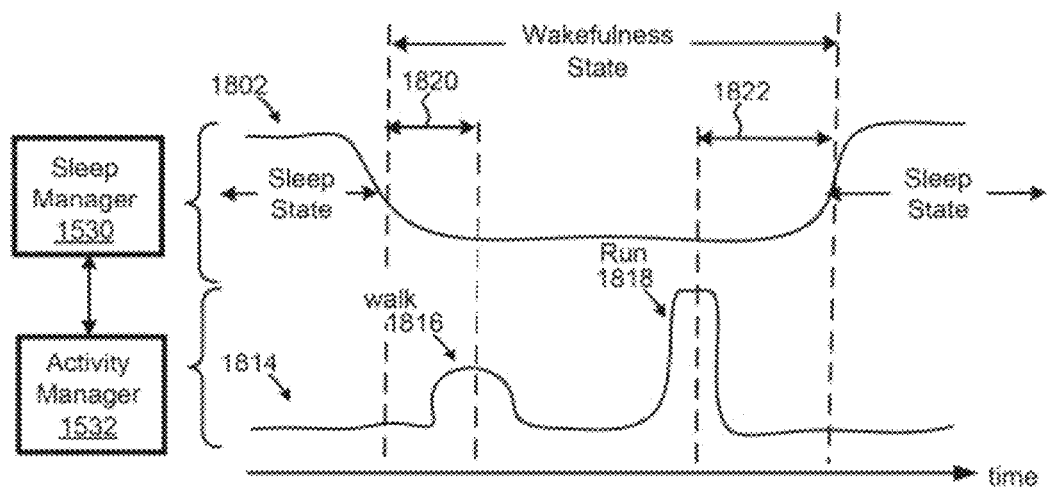

FIG. 18B depicts data 1802 representing sleep and data 1814 representing activity relative to time, whereby the data can represent instantaneous (e.g., in real or near real time) sleep data and activity data, or data 1802 and 1804 can represent archived or trend data, or projected activity occurring typically at different times during a day. Sleep manager 1530 and activity manager 1532 cooperate to modify one aspect of health and wellness, such as activity, to optimize another aspect, such as sleep. For example, sleep manager 1530 can determine instantaneous or predicted states of wakefulness and sleep for a user, and activity manager 1532 can determine or predict times at which user engages in walking 1816 and running 1818. In operation, manager coordinator 1706 or health and wellness evaluator 1702 can be configured to propose a time or duration 1820 in which a user is recommended to take a walk after waking up to take advantage of the most energetic part of the user's day or circadian rhythm. Positive or no points can be awarded if this activity is performed within time 1820. Further, manager coordinator 1706 or health and wellness evaluator 1702 can be configured to recommend to engage in exercise no later than an amount of time 1822 before bedtime. Positive points can be awarded if the user runs 1818 before time 1822. Negative points may be applied if the user runs 1818 during time 1812, as sleep likely is to be affected by exercising so close to sleep time.

Figure 18C:
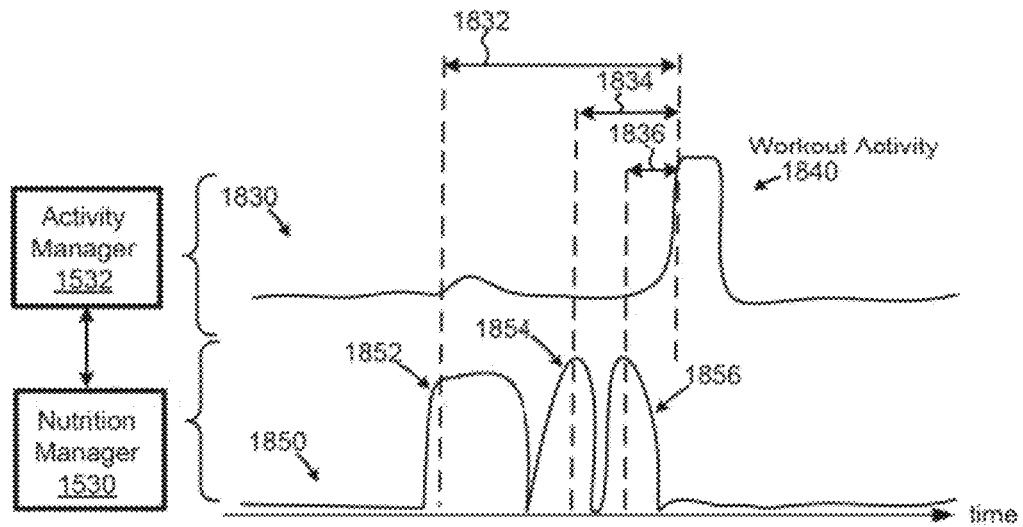

FIG. 18C depicts data 1830 representing activity and data 1850 representing nutrition relative to time, whereby the data can represent instantaneous (e.g., in real or near real time) activity data and nutrition data, or data 1830 and 1850 can represent archived or trend data, or projected activity occurring typically at different times during a day. Activity manager 1532 and nutrition manager 1530 cooperate to modify one aspect of health and wellness, such as activity, to optimize another aspect, such as sleep. For example, activity manager 1530 can determine instantaneous or predicted states of movement for a user, such as a workout activity 1840 (e.g., a marathon), and nutrition manager 1532 can be used to recommend times at which user consumes different foods or drink prior to working out. In operation, manager coordinator 1706 or health and wellness evaluator 1702 can be configured to propose a time or duration 1832 in which a user is recommended to consume fresh fruit, bagels, energy bars, pasta, and other like types of food 1852 (e.g., 3 to 5 hours before a competition). But during the time or duration 1834, the user is advised to consume fresh fruits, bagels, water, and like consumables 1854 (e.g., 2 to 3 hours before the competition), whereas the user is advised to consume specific fruits, such as watermelon and oranges, limited amounts of sport drink and like consumables 1856 during time or duration 1836 (e.g., 1 hour or less before competition). In various embodiments, activity manager 1532 and nutrition manager 1530 can cooperate to improve the overall health and wellness of a user based on the interplay between movement and nutrition. As such, the above-described is but one example. Positive can be awarded specific foods are consumed at the appropriate times.

Figure 18D:
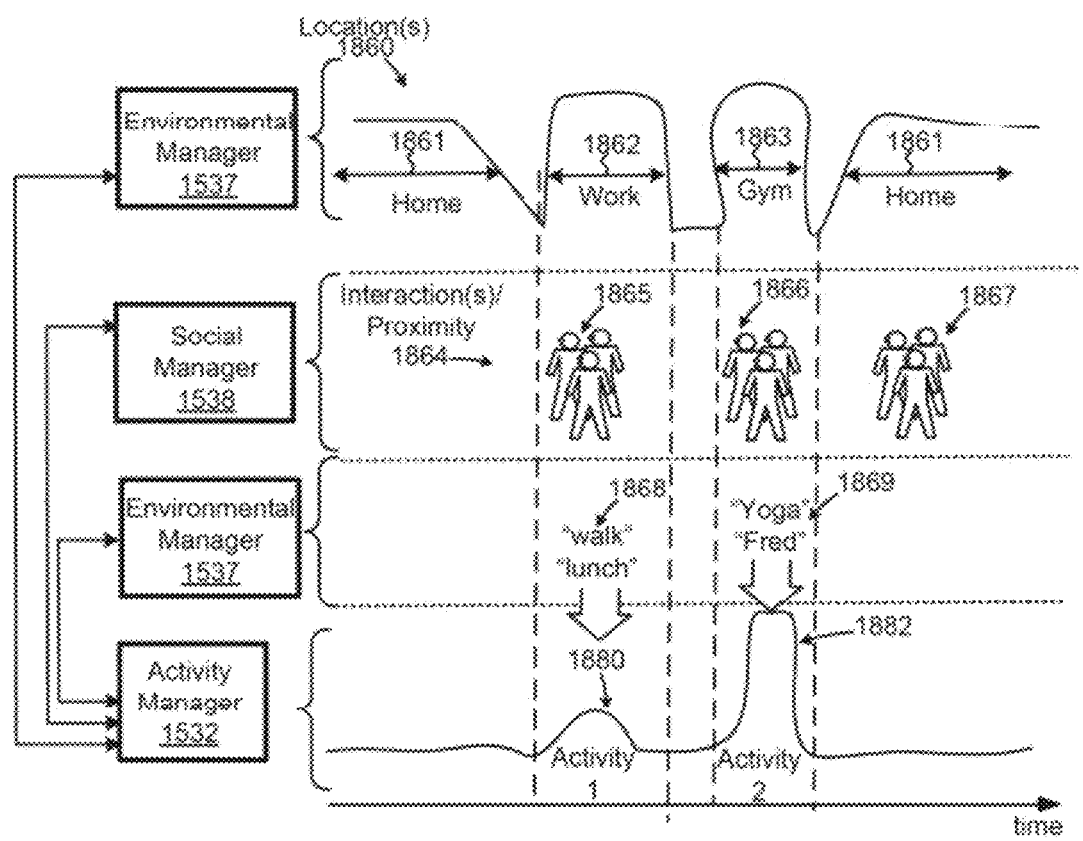

FIG. 18D depicts data 1860 representing location, data 1864 representing social interactions or proximity relative to time, data 1868 and 1869 representing environmental parameters including audio, and data 1880 and 1881 representing movement relative to time. The data shown can represent instantaneous activity data, social data, environmental data and activity data, or any of the data can represent archived or trend data, or projected activity occurring typically at different times during a day. In the example shown, environmental manager 1537, social manager 1538, and environmental manager 1537 are configured to assist activity manager 1532 in determining the type of activity a user is engaged. As shown, environmental manager 1537 can determine locations of a user at different times of the times, such as at home 1861, at work 1862, and at a gym 1863. Social manager 1538 is configured to determine that user associated with colleagues 1865 during a first time period, with other persons 1866 during a second time period, and family 1867 later on in the day. Environmental manager 1537 is configured to detect voiced words 1868, such as "walk" and "lunch," and further to detect voiced works 1869, such as "yoga" and "Fred." During the first time period, activity manager 1532 detects motion, and uses information that the person is at work, is associating with colleagues and is in an environment in which speech is detected to conclude that the user is likely walking with colleagues to lunch. As such, activity ("1") 1880 is determined to be walking. During the second time period, activity manager 1532 detects another type of motion, and uses information that the person is at a gym, is associating with other persons (e.g., wearing similar wearable devices and participating in similar motions) and is in an environment in which speech is detected to conclude that the user is likely participating in a yoga class. As such, activity ("2") 1882 is determined to be yoga. Note that the above-described examples are not intended to be limiting, but rather to provide examples of the various functionalities and/or structures that can be used to manage a user's overall health and wellness by optimizing one aspect of health and wellness to improve another, and to use acquired parameters (e.g., location, social interactions/proximities, etc.) to determine an activity in which a user is participating. An ordinarily skilled artisan ought to appreciate that many different implementations disclosed herein that can be modified to address any aspect of managing user health by motivating the user to challenge oneself to meet its health goals.

Although the foregoing examples have been described in some detail for purposes of clarity of understanding, the above-described inventive techniques are not limited to the details provided. There are many alternative ways of implementing the above-described invention techniques. The disclosed examples are illustrative and not restrictive.

What is claimed:

1. A method comprising:
   receiving data representing a profile defining parameters upon which a target score is established based on one or more health-related activities;
   acquiring data representing one or more subsets of acquired parameters based on one or more sensors disposed in a wearable computing device;
   determining data representing values for the one or more subsets of the acquired parameters based on reference values for the parameters set forth in the profile;
   calculating at a first processor a score based on data representing the values, the score representing an attained portion of the one or more health-related activities;
   causing presentation of a representation of the score relative to the target score; and
   adjusting a determination upon which to modify the target score,
   wherein the target score is indicative of one or more standards against which to compare one or more groups of the values aggregated to form the score.

2. The method of claim 1, wherein the score is indicative of an ability of a user to achieve a targeted level of health and wellness associated with the target score.

3. The method of claim 1, wherein the first processor is disposed in the wearable computing device.

4. The method of claim 1, wherein the one or more subsets of acquired parameters comprises:
   data representing one or more of
       a first subset of acquired parameters associated with sleep-related activities,
       a second subset of acquired parameters associated with nutrition-related activities, and
       a third subset of acquired parameters associated with movement-related activities.

5. The method of claim 4, wherein calculating the score based on the data representing the values comprises:
   aggregating one or more of a sleep score, a nutrition score and an activity score.

6. The method of claim 1, wherein the one or more subsets of acquired parameters comprises:
   data representing one or more of
       a fourth subset of acquired parameters associated with location-related activities, and
       a fifth subset of acquired parameters associated with social-related activities.

7. The method of claim 6, wherein calculating the score based on the data representing the values comprises:
   generating a context score based on the fourth and fifth subsets of acquired parameters; and
   aggregating the score and the context score to form the target score.

8. The method of claim 1, further comprising:
   adjusting the score for one or more of the values to form an adjusted score; and
   using the adjusted score to form an overall score.

9. The method of claim 8, further comprising:
   determining a context score based on either one or more location-related parameters or one or more social-related parameters; and
   forming the adjusted score using the context score.

10. The method of claim 1, further comprising:
    determining a magnitude of a difference between the score and the target score;
    predicting a subset of the acquired parameters to reduce the difference between the score and the target score; and
    generating data representing a recommendation to present to a user to engage in engage in a health-related activity.

11. The method of claim 10, wherein generating the data representing the recommendation comprises:
    generating data representing a suggestion to interact socially with a subset of people who are associated with activity scores indicative of active users; and
    causing presentation of the suggestion to contact interact with the subset of people to reduce the difference between the score and the target score.

12. The method of claim 10, wherein generating the data representing the recommendation comprises:
    generating data representing a suggestion to interact physically with a structure associated with a location of the user; and
    causing presentation of the suggestion to physically interact with the structure to reduce the difference between the score and the target score.

13. The method of claim 1, wherein acquiring data representing the acquired parameters comprises:
    obtaining for an acquired parameter data representing a type of parameter and units of the acquired parameter.

14. The method of claim 13, wherein receiving data representing the profile comprises:
    obtaining data representing a value per unit of a parameter and a reference value representing a target number of units of the parameter,
    wherein the parameter corresponds to the acquired parameter.

15. The method of claim 1, further comprising:
    causing generation of a graphical representation on an interface to induce modification of the values for at least one subset of the acquired parameters or
    causing generation of a haptic signal for providing vibratory feedback to induce modification of the values for at least one subset of the acquired parameters.

16. The method of claim 1, further comprising:
    determining trend data representing one or more calculated scores, the trend data being stored in a memory;
    identifying at least one acquired parameter as deviating by a threshold amount from a corresponding parameter defined by the profile;
    recommending modification of the at least one acquired parameter to reduce the threshold amount; and detecting whether the at least one acquired parameter is modified.

17. The method of claim 1, further comprising:
detecting the score exceeds the target score; and
reducing a rate at which the score as a function of the difference between the score and the target score.

18. The method of claim 1, further comprising:
determining a subset of scores;
changing a classification associated with a user based on the subset of scores,
wherein changing the classification including leveling up to a first classification or leveling down to a second classification.

19. A device comprising:
a first interface configured to receive data representing acquired parameters from one or more sensors, at least one sensor being disposed in a wearable computing device;
an aggregation engine comprising:
  a repository configured to store data representing a profile defining parameters upon which a target score is established; and
  one or more managers including one or more processors, at least one manager being configured to receive data representing a subset of the acquired parameters and further configured to determine data representing values for the subset of the acquired parameters, the values representing a point value relative to reference values for the parameters set forth in the profile;
a score generator configured to:
  calculate a score based on data representing the values; and
  adjust the score based on threshold amounts for one or more of the values to form an adjusted score;
a general health and wellness module configured to facilitate modification of a value of an acquired parameter associated with a state of a user to change the target score; and
a status manager configured to cause presentation of a representation of the target score, wherein the score is indicative of relative proximity to the target score.

* * * * *